United States Patent
Bottini et al.

(10) Patent No.: US 11,331,388 B1
(45) Date of Patent: May 17, 2022

(54) PTP4A1 AS A THERAPEUTIC TARGET FOR FIBROTIC DISEASES AND DISORDERS INCLUDING SYSTEMIC SCLEROSIS

(71) Applicant: LA JOLLA INSTITUTE FOR ALLERGY AND IMMUNOLOGY, La Jolla, CO (US)

(72) Inventors: Nunzio Bottini, San Diego, CA (US); Cristiano Sacchetti, San Diego, CA (US); Stephanie M. Stanford, La Jolla, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 0 days.

(21) Appl. No.: 15/257,587

(22) Filed: Sep. 6, 2016

Related U.S. Application Data

(60) Provisional application No. 62/214,070, filed on Sep. 3, 2015.

(51) Int. Cl.
| | | |
|---|---|---|
| *C07K 16/40* | (2006.01) | |
| *A61K 38/46* | (2006.01) | |
| *C12N 15/113* | (2010.01) | |
| *C12N 15/86* | (2006.01) | |
| *C12Q 1/6883* | (2018.01) | |
| *A61K 45/06* | (2006.01) | |
| *G01N 33/68* | (2006.01) | |
| *A01K 67/027* | (2006.01) | |

(52) U.S. Cl.
CPC ............ *A61K 45/06* (2013.01); *A61K 38/465* (2013.01); *C07K 16/40* (2013.01); *C12N 15/1137* (2013.01); *C12N 15/86* (2013.01); *C12Y 301/03048* (2013.01); *A01K 67/0276* (2013.01); *A01K 2217/15* (2013.01); *A01K 2267/0331* (2013.01); *C07K 2317/76* (2013.01); *C12N 2310/3233* (2013.01); *C12N 2710/10043* (2013.01); *C12N 2740/15043* (2013.01); *C12Q 1/6883* (2013.01); *C12Q 2600/158* (2013.01); *G01N 33/6893* (2013.01); *G01N 2333/916* (2013.01); *G01N 2800/24* (2013.01)

(58) Field of Classification Search
CPC .............. C12N 15/113; C12N 15/1017; C12N 2310/11; C12N 15/8218
See application file for complete search history.

(56) References Cited

U.S. PATENT DOCUMENTS

| 2007/0026398 A1* | 2/2007 | Farnsworth | C12Q 1/42 435/6.16 |
|---|---|---|---|
| 2011/0206657 A1* | 8/2011 | Zeng | C07K 16/18 424/130.1 |

OTHER PUBLICATIONS

Integrated DNA Technologies. Designing Antisense Oligonucleotides, published 2005 and 2011. Available at https://sfvideo.blob.core.windows.net/sitefinity/docs/default-source/technical-report/designing-asos.pdf?sfvrsn=f94b3407_9.*
Sacchetti, C., et al., PTP4A1 promotes TGFβ signaling and fibrosis in systemic sclerosis, Nature Communications, 2017, 8(1060):1-14; DOI: 10.1038/S41467-017-01168-1.
Lagana et al., "Synthetic RNAs for gene regulation: design principles and computational tools", Frontiers in Bioengineering and Biotechnology, Dec. 11, 2014, pp. 1-7.
Horwich et al., "Design and Delivery of Antisense Oligonucleotides to Block microRNA Function in Cultured Drosophila and Human Cells", Nat Protoc., Oct. 3, 2008, pp. 1537-1549, vol. 3(10).
Aartsma-Rus et al., "Guidelines for Antisense Oligonucleotide Design and Insight Into Splice-modulating Mechanisms", The American Society of Gene Therapy, Sep. 23, 2008, pp. 548-553.
Morcos et al., "Vivo-Morpholinos: A non-peptide transporter delivers Morpholinos into a wide array of mouse tissues", BioTechniques, Dec. 2008, pp. 613-623, vol. 45(6).
Desmet et al., "Human Splicing Finder: an online bioinformatics tool to predict splicing signals", Nucleic Acids Research, Apr. 1, 2009, pp. 1-14, vol. 37(9).

* cited by examiner

*Primary Examiner* — Vanessa L. Ford
*Assistant Examiner* — Sandra Dillahunt
(74) *Attorney, Agent, or Firm* — Pillsbury Winthrop Shaw Pittman LLP

(57) ABSTRACT

Methods of treating fibrotic diseases and disorders including Systemic sclerosis (SSc) are provided. Methods include, for example, administering to a subject an effective amount of an antagonist/inhibitor of PTP4A1 protein expression or activity to treat a fibrotic disease or disorder such as SSc, or an associated pathology such as organ or skin fibrosis.

15 Claims, 27 Drawing Sheets
Specification includes a Sequence Listing.

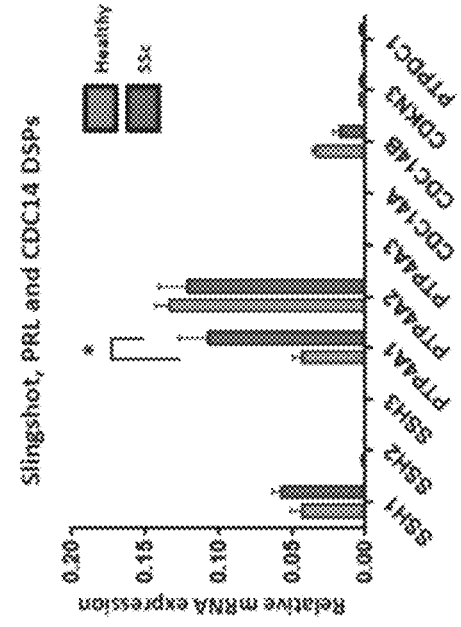
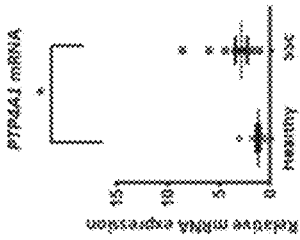
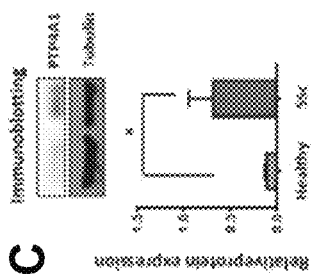
FIG. 2A
FIG. 2B
FIG. 2C

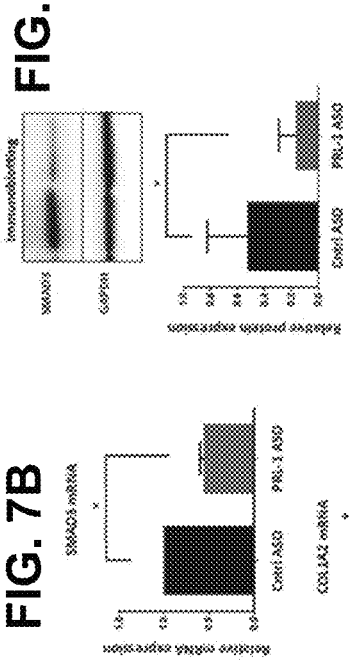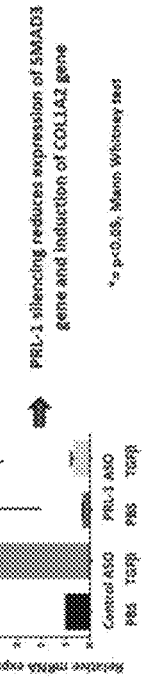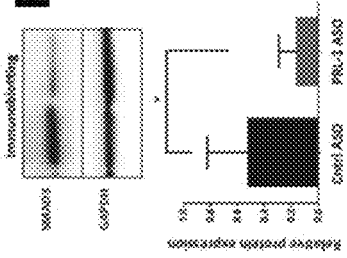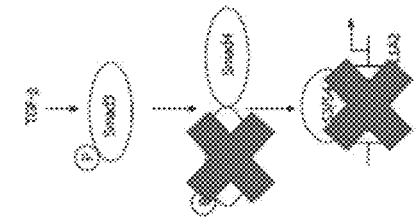

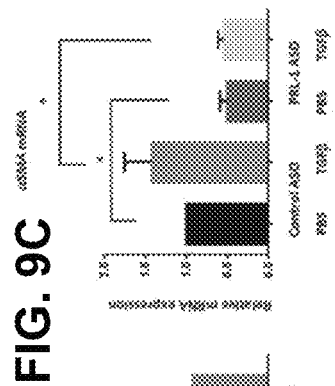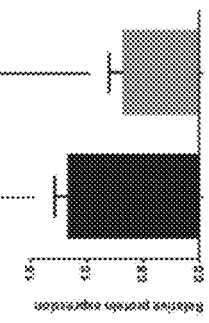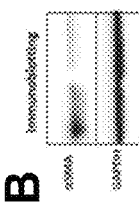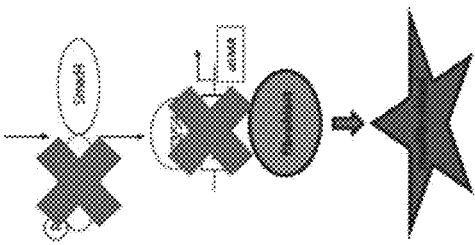
FIG. 9A  FIG. 9B  FIG. 9C
Attenuation of the αSMA pro-fibrotic pathway in human dermal fibroblasts subjected to knock-down of PRL-1
PRL-1 silencing reduces transcription of αSMA gene

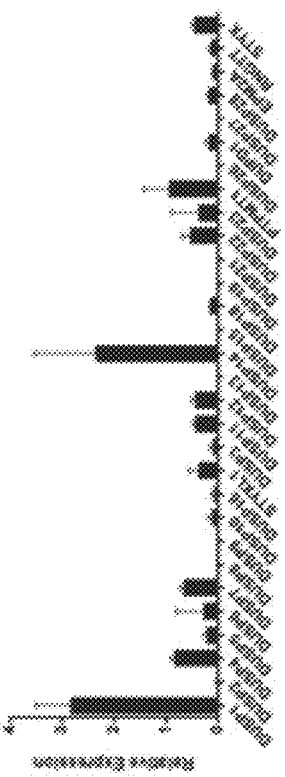
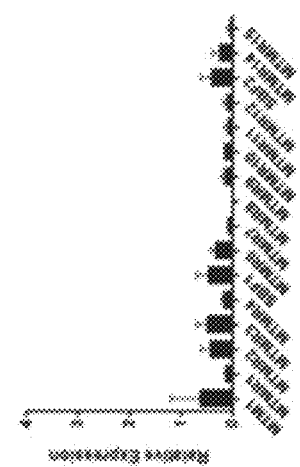
FIG. 14A
FIG. 14B Myotubularin DSPs
FIG. 14C Class II, III, IV and novel PTPs
FIG. 14D Slingshot, PRL, CDC14 and PTEN DSPs
FIG. 14E Transmembrane PTPs
FIG. 14F Non-Receptor PTPs

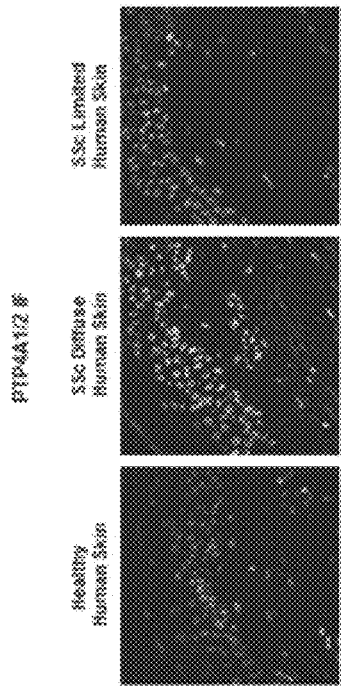
FIG. 15A
FIG. 15B
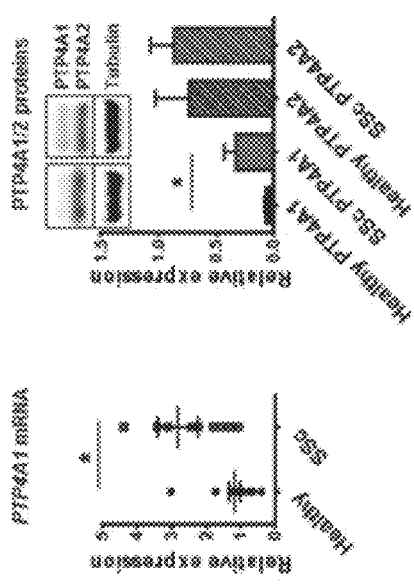
FIG. 15D
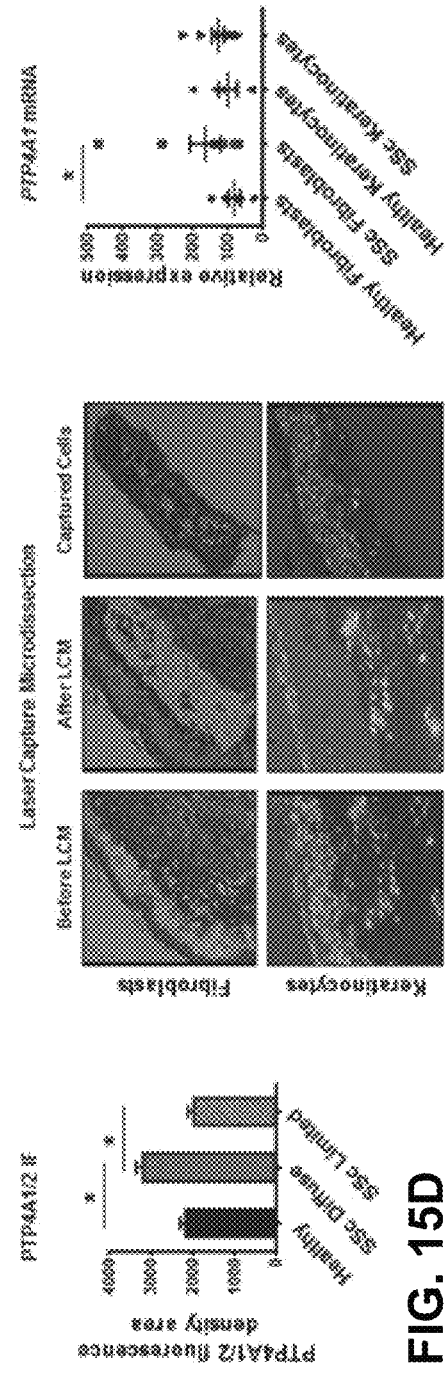
FIG. 15C
FIG. 15E

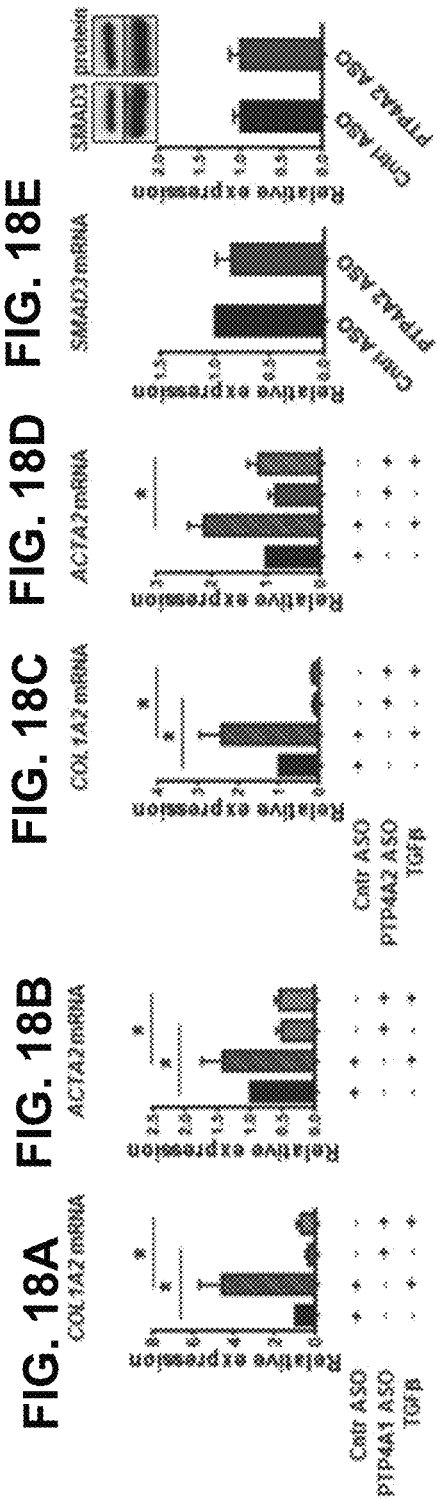
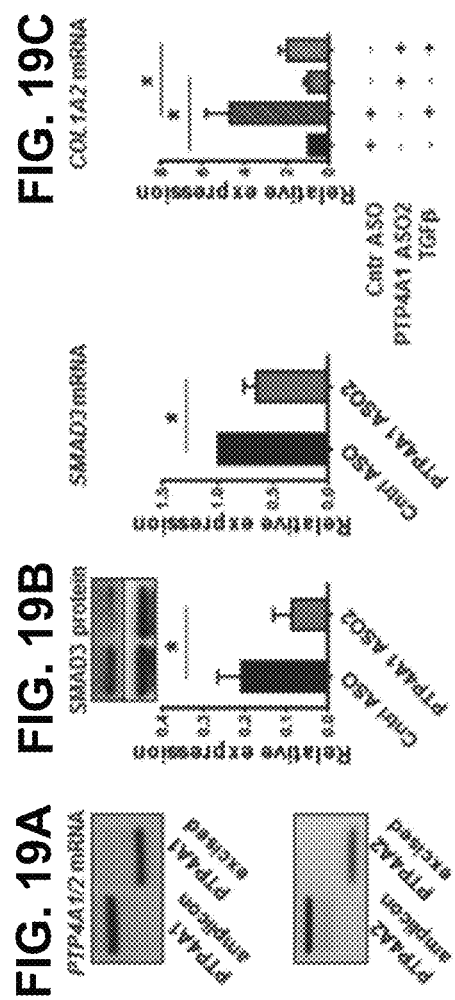

FIG. 20A PTP4A1 mRNA

FIG. 20B SMAD3 mRNA

FIG. 20C COL1A2 mRNA

FIG. 20D ACTA2 mRNA

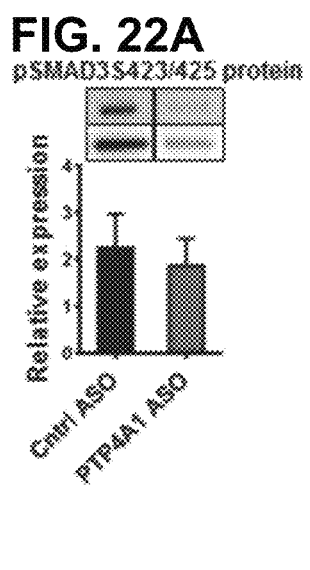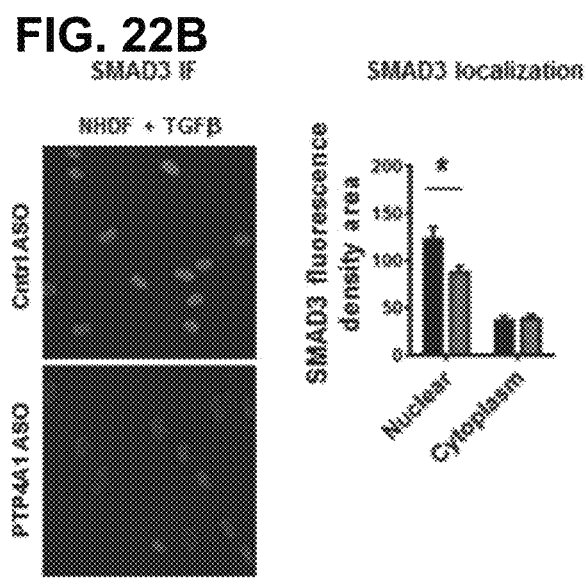
FIG. 22A
FIG. 22B

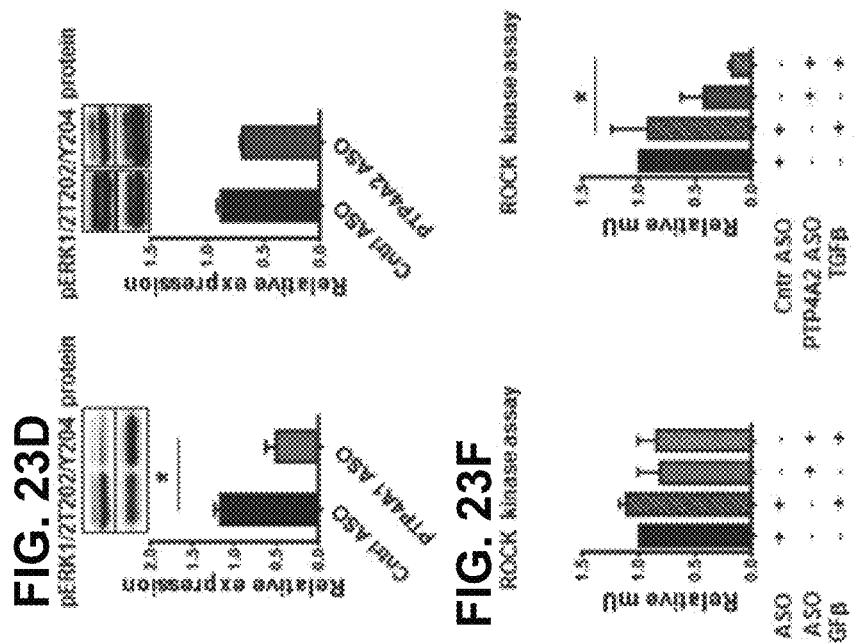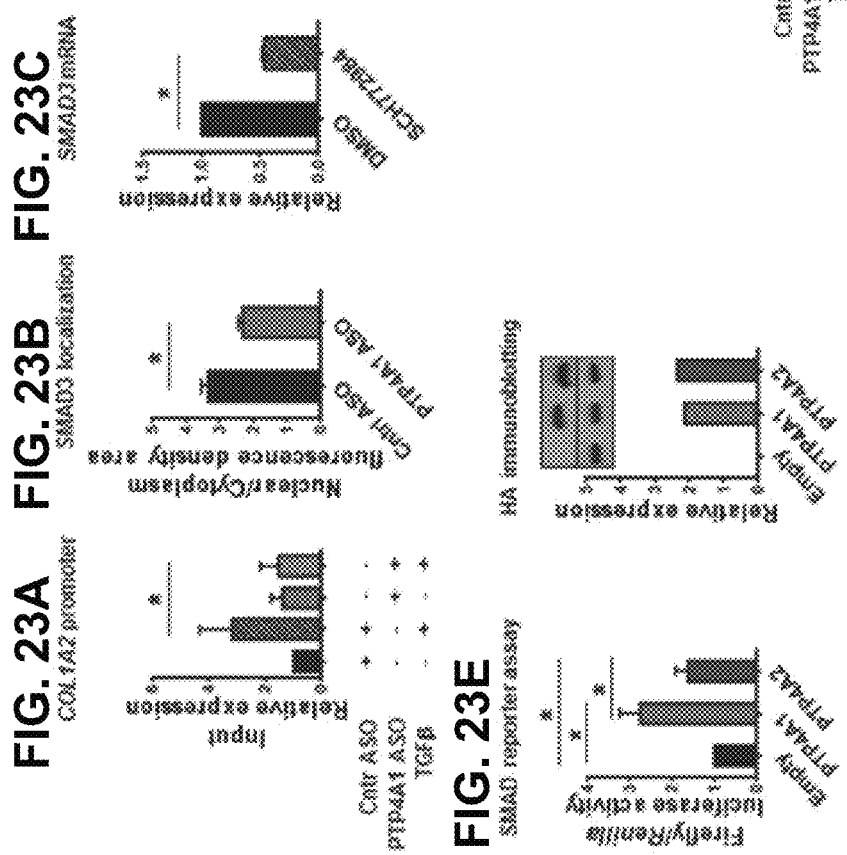

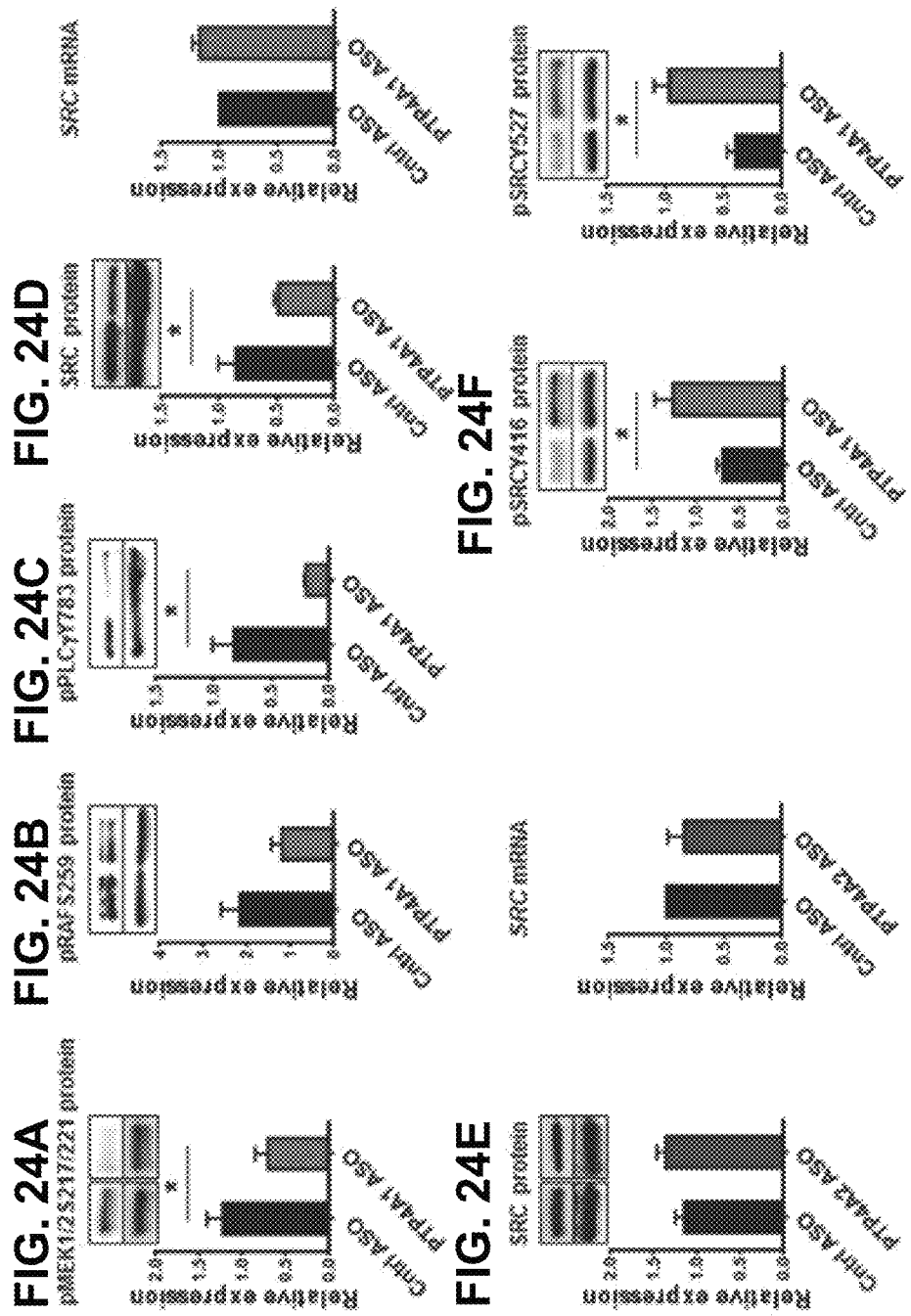

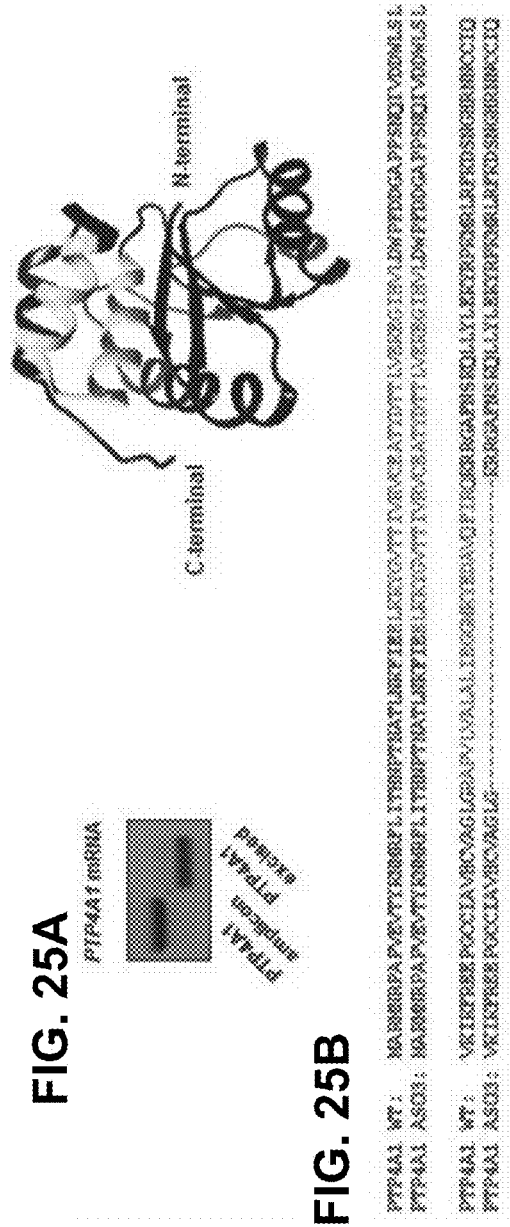

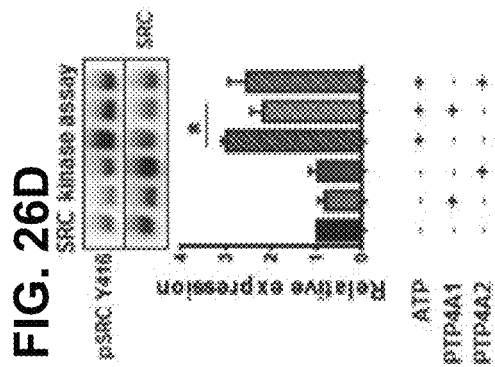
FIG. 26A
FIG. 26B
FIG. 26C
FIG. 26D
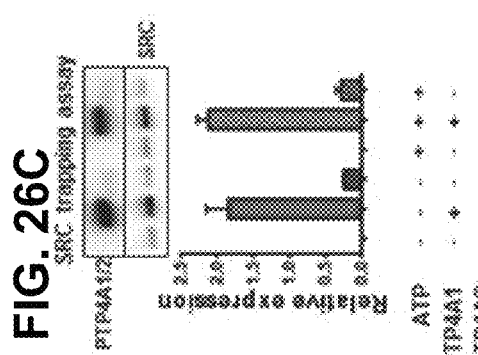
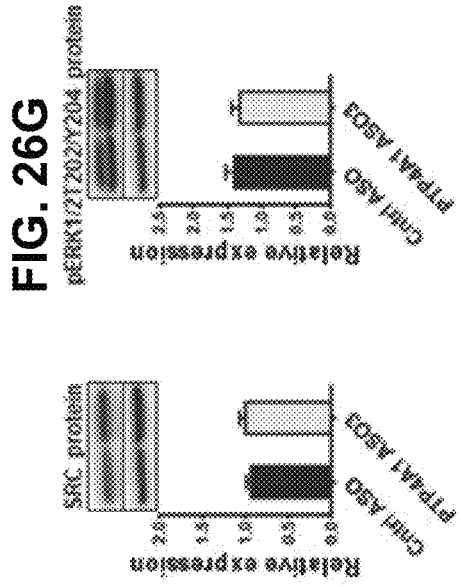
FIG. 26E
FIG. 26F
FIG. 26G
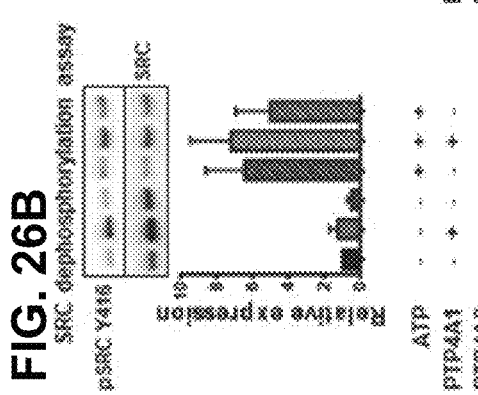
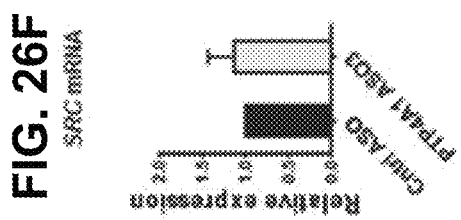
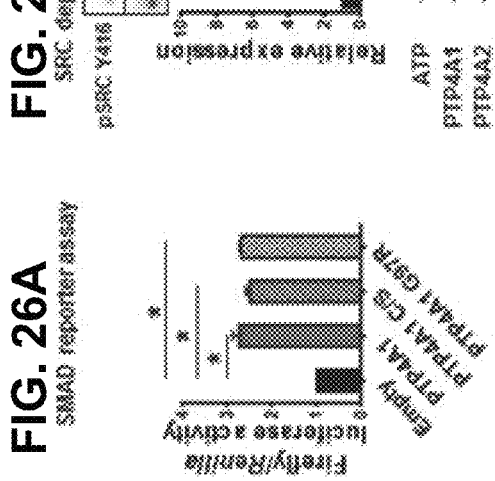
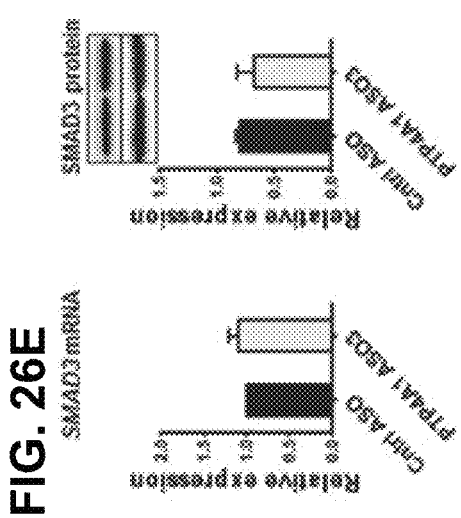

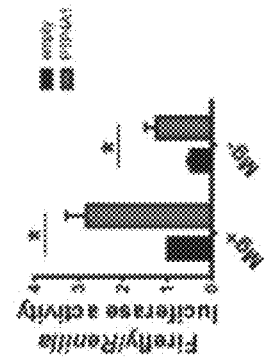
FIG. 29A
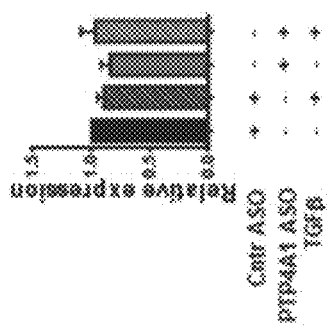
FIG. 29B
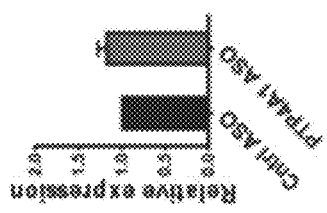
FIG. 29D
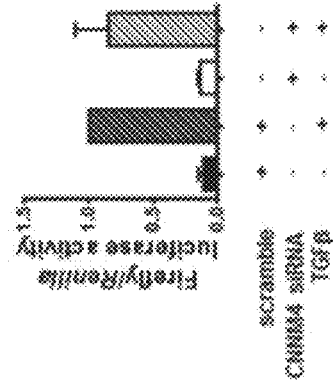
FIG. 29C
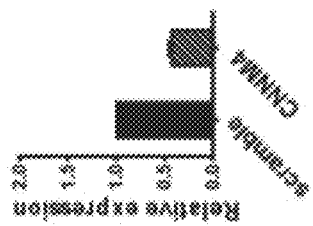
FIG. 29E
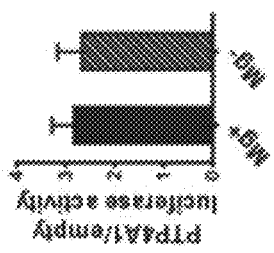

PTP4A1 AS A THERAPEUTIC TARGET FOR FIBROTIC DISEASES AND DISORDERS INCLUDING SYSTEMIC SCLEROSIS

RELATED APPLICATIONS

This patent application claims the benefit of U.S. Provisional Patent Application No. 62/214,070 filed on Sep. 3, 2015. The entire content of the foregoing application is incorporated herein by reference, including all text, tables and drawings.

SEQUENCE LISTING

The application contains a Sequence Listing which has been submitted electronically in ASCII format and is incorporated by reference herein in its entirety. Said ASCII copy, created on Nov. 4, 2016, is named LIAI0448514_ST25.txt and is 8,043 bytes in size.

INTRODUCTION

Systemic sclerosis (SSc) is a multi-system autoimmune connective tissue disorder that leads to fibrosis of the skin and internal organs, resulting in significant patient morbidity and mortality. The fibroblast is considered a key target cell type for possible therapies aimed at modifying excessive deposition of extracellular matrix in affected organs. Several studies have assessed the role of protein tyrosine kinases (PTKs) in the pathophysiology of SSc fibroblasts and fibrosis. However the role of protein tyrosine phosphatases (PTPs), a family of enzymes that naturally balance the action of PTKs in signal transduction, in fibrosis remains mostly unexplored.

SUMMARY

Provided herein, in certain aspects, are methods of modulating protein tyrosine phosphatase 4A1 (PTP4A1) expression or activity. In one embodiment, a method includes contact or administration of an agent which modulates expression or activity of protein tyrosine phosphatase 4A1 (PTP4A1), in vitro (e.g., in a cell line or culture), ex vivo or in vivo.

The invention also provides methods of modulating the pathology of systemic sclerosis. In one embodiment, a method includes contact or administration of an effective amount of an antagonist of protein tyrosine phosphatase 4A1 (PTP4A1) sufficient to modulate pathology of systemic sclerosis.

The invention further provides methods of treating a fibrotic disease or disorder in a subject. In one embodiment, a method includes administering an effective amount of an antagonist of protein tyrosine phosphatase 4A1 (PTP4A1) to a subject sufficient to treat the fibrotic disease or disorder.

The invention additionally provides methods of treating systemic sclerosis in a subject. In one embodiment, a method includes contact or administration of an effective amount of an antagonist of protein tyrosine phosphatase 4A1 (PTP4A1) to a subject sufficient to treat systemic sclerosis.

In various embodiments, a method includes decreasing, reducing, suppressing, inhibiting, limiting or controlling expression or activity of PTP4A1.

In various aspects, an antagonist of protein tyrosine phosphatase 4A1 (PTP4A1) is contacted or administered in vitro (e.g., in a cell line or culture), ex vivo or in vivo, for example, to a subject sufficient to treat systemic sclerosis. In particular aspects, contact or administration is to the skin or lungs of a subject. In more particular aspects, a method includes contacting or administering a sufficient amount of protein tyrosine phosphatase 4A1 (PTP4A1) antagonist to a subject in need thereof to reduce or inhibit skin or lung fibrosis, or another fibrotic disease or disorder, in the subject.

PTP4A1 inhibitors include, for example, molecules that bind to PTP4A1 and inhibit or decrease PTP4A1 expression, function or activity. PTP4A1 inhibitors also include, for example, molecules that bind to PTP4A1 targets or receptors and that inhibit or decrease PTP4A1 target or receptor expression, function or activity.

Particular non-limiting examples include a small molecule that binds to the PTP4A1 protein or a PTP4A1 target or receptor; an antibody or antibody fragment that binds to the PTP4A1 protein or a PTP4A1 target or receptor; a dominant negative protein that binds to the PTP4A1 protein or a PTP4A1 target or receptor; or an inhibitory nucleic acid (e.g., RNAi, micro-RNA (miRNA), siRNA, shRNA, trans-splicing RNA, antisense RNA, aptamers or triplex forming RNA that binds to PTP4A1 nucleic acid or protein) that decreases, reduces, suppresses, inhibits, limits or controls expression or activity of PTP4A1 or a PTP4A1 target or receptor.

Contact, administration or delivery of PTP4A1 antagonists/inhibitors can be with micelles or liposomes. Such micelles and liposomes can comprise polymers that are able to facilitate entry of PTP4A1 antagonists/inhibitors into a target cell, for example. Contact, administration or delivery of PTP4A1 antagonists/inhibitors can also be with a vector such as a viral vector that infects a cell (e.g., a fibroblast or dermal cell), such as a human cell. Representative vectors include lentiviral and adeno-associated viral (AAV) vectors.

Invention methods include contact, administration or delivery, in vitro, ex vivo or in vivo (e.g., to a subject in need of treatment). Invention methods also include routes of contact or administration of a PTP4A1 antagonist (inhibitor) locally, regionally and systemically. In a particular embodiment, a PTP4A1 antagonist (inhibitor) is administered topically to achieve delivery to skin or dermis (e.g., to surface of skin), or systemically to achieve delivery system wide or to an afflicted internal organ or tissue (e.g., in the lungs). In further particular embodiments, contact, administration or delivery is to arms, legs, torso, back, hands, feet, neck, face or head of the subject. In additional particular embodiments, contact, administration or delivery is to liver or pulmonary (respiratory) system.

In various embodiments, a fibrotic disease or disorder, such as Systemic sclerosis (SSc), or pathology or any symptom thereof, is reduced, decreased, inhibited, delayed, halted, or prevented in the subject, locally, or regionally in an area (region) of the subject. In particular aspects, a symptom is reduced, decreased, inhibited, delayed, halted, or prevented in skin and lungs. In another aspect, a method reduces, decreases, inhibits, delays, halts, or prevents fibrotic disease or disorder in an organ or tissue such as skin or lung fibrosis, or any symptom thereof. In yet another embodiment, contact or administration in vivo is to a subject that has previously experienced a fibrotic disease or disorder, such as Systemic sclerosis (SSc), or pathology, or any symptom thereof, or is in need of inhibited or reduced fibrotic disease or disorder, such as Systemic sclerosis (SSc), or pathology or any symptom thereof.

In accordance with the invention, there are also provided, methods of inhibiting, reducing or decreasing progression, severity, frequency, duration or probability of one or more symptoms caused by or associated with a fibrotic disease or disorder, such as Systemic sclerosis (SSc), or pathology or any symptom thereof. In various embodiments, a method includes administering to a subject an amount of a PTP4A1 antagonist (inhibitor) sufficient to inhibit, reduce or decrease progression, severity, frequency, duration or probability of a fibrotic disease or disorder, such as Systemic sclerosis (SSc), or pathology or any symptom thereof.

In various embodiments, a method decreases, reduces, suppresses, inhibits, limits or controls pathology of systemic sclerosis or the fibrotic disease or disorder. In various embodiments, a method decreases, reduces, suppresses, inhibits, limits or controls in a subject an undesirable or adverse symptom of systemic sclerosis or the fibrotic disease or disorder.

In various aspects, non-limiting symptoms of a fibrotic disease or disorder such as Systemic sclerosis (SSc) include organ and/or skin fibrosis, skin thickening (thickening of the epidermis or dermis), hardening or tightening of patches of skin, skin tenderness, temperature (heat/cold) sensitivity, cutaneous pruritus, whitening of hands on exposure to cold, pain in affected digits, difficulty in swallowing foods or liquids, gastro-esophageal reflux, nausea, vomiting, weight loss, abdominal cramps, blotting diarrhea, fecal incontinence, shortness of breath on exertion, palpitations without characteristic pain in thoracic cavity, nonproductive cough, atypical chest pain, fatigue, dyspnea, hypertension, joint pain, limitation of movement, joint swelling, muscle pain, acute kidney failure, inflammatory myopathy or weakness. Further symptoms, include, for example, abnormalities of the nail capillary bed (determined clinically or through capillaroscopy), restrictive changes at pulmonary function tests, abnormal computerized tomography findings suggestive of interstitial lung disease, abnormal echocardiography or heart catheterization findings indicating presence of pulmonary artery hypertension, abnormal swallowing and gastric motility tests indicating reduced esophageal and/or gastric motility, thickening and/or induration of the dermis and the connective tissue of the lungs, stomach and intestine. Still further symptoms of a fibrotic disease or disorder such as Systemic sclerosis (SSc) include, include, for example, excessive or aberrant deposition of extracellular matrix.

Symptoms of a fibrotic disease or disorder can affect cells, tissues and/or organs. Exemplary tissues and/or organs include skin and nails, and internal organs and tissues such as gastro-intestinal tract (esophagus, stomach, small or large intestine), skeletal muscle/joints, kidney, liver and pulmonary (respiratory) system such as lungs, larynx, trachea, alveoli, bronchi, bronchioles and diaphragm.

Invention treatment methods include providing a given subject with an objective or subjective improvement of the disorder or disease, a symptom caused by or associated with the disorder or disease, or the probability or susceptibility of a subject to the condition or a symptom caused by or associated with the disorder or disease. In various embodiments, treatment reduces, decreases, inhibits, delays, eliminates or prevents the probability, susceptibility, severity, frequency, or duration of one or more symptoms caused by or associated with the disorder or disease, e.g., a fibrotic disease or disorder, such as Systemic sclerosis (SSc). In a particular aspect, a method reduces the probability, severity, frequency, duration or delays, halts, or prevents organ or skin fibrosis. In additional aspects, treatment improves or increases skin elasticity. In further aspects, a treatment improves, reduces or inhibits skin thickening, tightening or hardening, of epidermis or dermis.

Candidate subjects for methods of the invention include mammals, such as humans. Candidate subjects for methods of the invention also include subjects that are in need of treatment, e.g., any subject that may benefit from a treatment. Candidate subjects for methods of the invention therefore include subjects that have or are at risk of having a fibrotic disease or disorder, such as Systemic sclerosis (SSc).

Methods of the invention can be practiced by administration or contact with any dose amount, frequency, delivery route or timing of a PTP4A1 antagonist (inhibitor). In a particular embodiment, a subject is administered or contacted with a PTP4A1 antagonist (inhibitor) one, two, three, four or more times hourly, daily, bi-weekly, weekly, monthly or annually. In additional embodiments, an amount administered is about 0.00001 mg/kg, to about 10,000 mg/kg, about 0.0001 mg/kg, to about 1000 mg/kg, about 0.001 mg/kg, to about 100 mg/kg, about 0.01 mg/kg, to about 10 mg/kg, about 0.1 mg/kg, to about 1 mg/kg body weight, one, two, three, four, or more times per hour, day, bi-weekly, week, month or annually. In further embodiments, the amount administered is less than about 0.00001 mg/kg, one, two, three, four, or more times per hour, day, bi-weekly, week, month, bi-monthly, or annually. In particular aspects, the amount is administered substantially contemporaneously with, or within about 1-60 minutes, hours, or days of the onset of a fibrotic disease or disorder, such as Systemic sclerosis (SSc), or a symptom caused by or associated with a fibrotic disease or disorder, such as Systemic sclerosis (SSc).

Methods of the invention can be practiced in conjunction with one or more other treatment protocols or therapeutic regimens. In a particular embodiment, a method includes contacting or administering a second agent or drug to the subject prior to, with or following contact or administration of a PTP4A1 antagonist (inhibitor). In particular aspects, a second agent or drug includes an anti-organ fibrosis, anti-skin fibrosis, anti-inflammatory, or an immune-suppressant drug or agent.

Invention compositions can be formulated as appropriate for practice of the methods. In one embodiment, a composition includes a PTP4A1 antagonist (inhibitor) and a pharmaceutically acceptable carrier. In a particular aspect, the carrier is a physiologically acceptable gas, liquid, dry powder or an aerosol. In an additional particular aspect, the carrier is a capable of contact with skin or dermis, or traversing skin or dermis. In a further particular aspect, the carrier is lipophilic or non-lipophilic.

In accordance with the invention, there are further provided animal models of human systemic sclerosis, wherein the model has reduced or inactive expression of endogenous gene encoding protein tyrosine phosphatase 4A1, or has a disrupted or knocked-out endogenous gene encoding protein tyrosine phosphatase 4A1. Such models include those generated by genetic modification of stem cells. Suitable models include rodents, such as a rat or mouse.

In accordance with the invention, there are additionally provided methods of measuring expression or activity of PTP4A1. In one embodiment, a method includes contacting a sample from a subject with a reagent that binds to PTP4A1 nucleic acid or protein and determining the amount of PTP4A1 nucleic acid or protein in the sample.

In accordance with the invention, there are moreover provided methods of identifying a subject at risk of having or having systemic sclerosis. In one embodiment, a method includes measuring expression or activity of PTP4A1, wherein elevated PTP4A1 expression or activity compared to control PTP4A1 expression or activity identifies the subject as at risk of having or having systemic sclerosis.

Still further provided are methods of monitoring a subject treated for systemic sclerosis. In one embodiment, a method includes measuring expression or activity of PTP4A1 before treatment; measuring expression or activity of PTP4A1 after treatment; and comparing PTP4A1 expression or activity before and after treatment. A reduction of expression or activity of PTP4A1 after treatment compared to before treatment indicates improvement of systemic sclerosis; or the same or an increase in PTP4A1 expression or activity after treatment compared to before treatment indicates no improvement or worsening of systemic sclerosis.

Still additionally provided are methods of systemic sclerosis prognosis in a subject. In one embodiment, a method includes measuring expression or activity of PTP4A1 prior to or after an initial or subsequent systemic sclerosis treatment; measuring expression or activity of PTP4A1 after an initial or a further systemic sclerosis treatment; and comparing PTP4A1 expression or activity following the initial or the further systemic sclerosis treatment to PTP4A1 expression or activity prior to or after the initial or the subsequent systemic sclerosis treatment. A reduction of expression or activity of PTP4A1 following the initial or the further systemic sclerosis treatment compared to PTP4A1 expression or activity prior to or after the initial or the subsequent systemic sclerosis treatment indicates improved systemic sclerosis prognosis.

Such methods and method steps can be performed after an initial systemic sclerosis treatment, such as a first treatment, and again after a subsequent systemic sclerosis treatment such as a second, third, fourth, fifth, sixth, seventh, eighth, ninth, tenth or further treatment. Such methods and method steps can be performed a plurality of times prior to treatment, during treatment or after treatment, over a period of time.

Such methods and method steps typically measure expression or activity of PTP4A1 in a sample from a subject. Reagents can be used including, but not limited to a detectable reagent such as a detectable nucleic acid that binds to PTP4A1 nucleic acid or detectable protein (e.g., an antibody) that binds to PTP4A1 protein.

DESCRIPTIONS OF DRAWINGS

FIG. 1 shows mRNA expression profile of all the PTPs (109 genes) in 4 primary dermal fibroblast lines from patients with diffuse SSc compared to 5 primary dermal fibroblast lines from healthy subjects.

FIGS. 2A-2C show that after analysis of a second cohort of 6 SSc fibroblast lines and 5 healthy fibroblast lines, only PTP4A1 showed a significant different expression level from SSc and healthy patients with Mann Whitney test (FIG. 2A). This result was confirmed with a third cohort of patients and healthy subjects (FIG. 2B). PTP4A1 also showed a significantly increased protein level in SSc fibroblasts compared with healthy patients using Mann Whitney test (FIG. 2C).

Figures 6A, 6B, 6C:
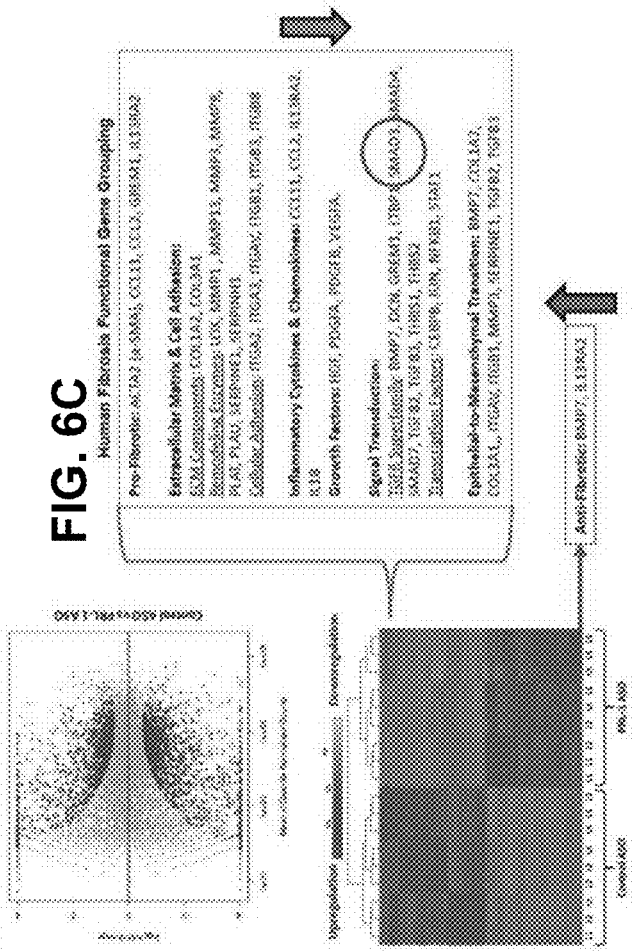

FIGS. 6A-6C show whole transcriptome analysis by Next Generation Sequencing performed on 3 lines of normal human dermal fibroblasts subjected to knockdown of the PTP4A1 gene with cell permeable morpholino oligonucleotides. Results analyzed using the Deseq software. (FIG. 6A) differential expression of all genes in cells treated with anti PTP4A1 morpholino vs control morpholino. In red are highlighted the genes with a statistical increased (upper part of the figure) or decreased (lower part of the figure) expression. (FIG. 6B) gene upregulation (in red) and downregulation (in green) with a heat map graphical representation. Knockdown of PTP4A1 gene induced a dramatic inhibition of the expression of numerous genes that are implicated in fibrosis, including collagens (COL1A2, COL3A1), ACTA2 and SMAD3 (FIG. 6C).

FIGS. 7A-7D. FIG. 7A shows how PTP4A1 interrupts the canonical SMAD3-dependent TGFbeta pathway. The SMAD3 gene was downregulated with PTP4A1 knockdown in TGFbeta1-untreated cells (FIG. 7B). FIG. 7C shows mean±SEM of densitometric scan relative expression plus representative immunoblots of SMAD3 protein (upper bands) and GAPDH protein (lower bands) used as control in TGFbeta1-untreated cells. FIG. 7D shows reduced COL1A2 gene expression in presence of anti-PTP4A1 morpholino in TGFbeta1-treated or untreated cells. *, $p<0.05$, Mann-Whitney test.

Figure 8:
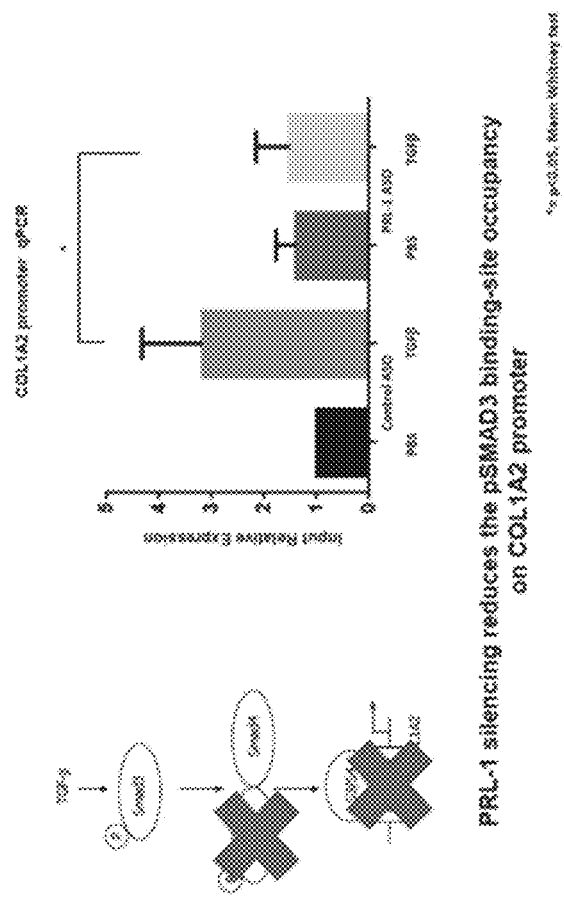

FIG. 8 shows that PTP4A1 knockdown reduces the amount of SMAD3 that binds the promoter of COL1A2 gene.

FIGS. 9A-9C. FIG. 9A shows how PTP4A1 interrupts the transformation of fibroblasts in myofibroblasts, which are cells involved in the inflammatory response to injury. FIG. 9B shows mean±SEM of densitometric scan relative expression plus representative immunoblots of alphaSMA protein (upper bands) and GAPDH protein (lower bands) used as control in TGFbeta1-untreated cells. FIG. 9C shows reduced ACTA2 gene expression in in presence of anti-PTP4A1 morpholino in TGFbeta1-treated or untreated cells. *, $p<0.05$, Mann-Whitney test.

Figure 10:
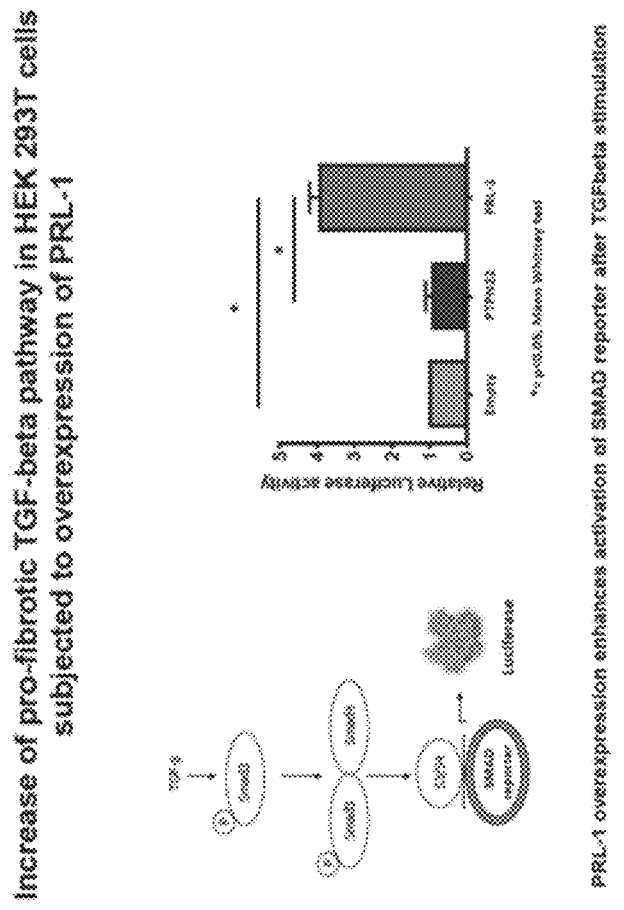

FIG. 10 shows that PTP4A1 over-expression enhances activation of SMAD reporter after TGFbeta stimulation. Graph shows mean±SEM of relative ratio of Firefly/*Renilla* luciferase signal of cells transfected with empty, PTP4A1 WT and a PTPN22 vectors in 3 independent experiments. Overexpression of PTP4A1 in HEK 293T cells led to enhancement of TGFbeta-induced activation of a SMAD-sensitive reporter. Empty vector and PTPN22 overexpression didn't induce the reporter activation. * $p<0.05$, Mann-Whitney test.

Figure 11:
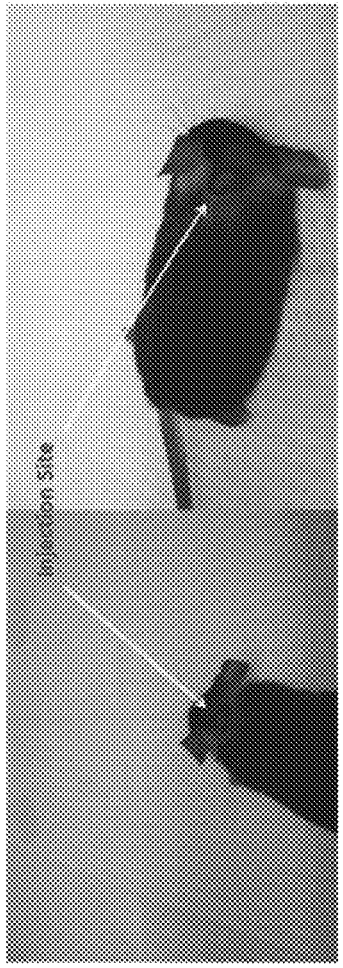

FIG. 11 shows that Dermal sclerosis induced by Bleomycin closely resembles systemic sclerosis both histologically and biochemically.

Figure 12:
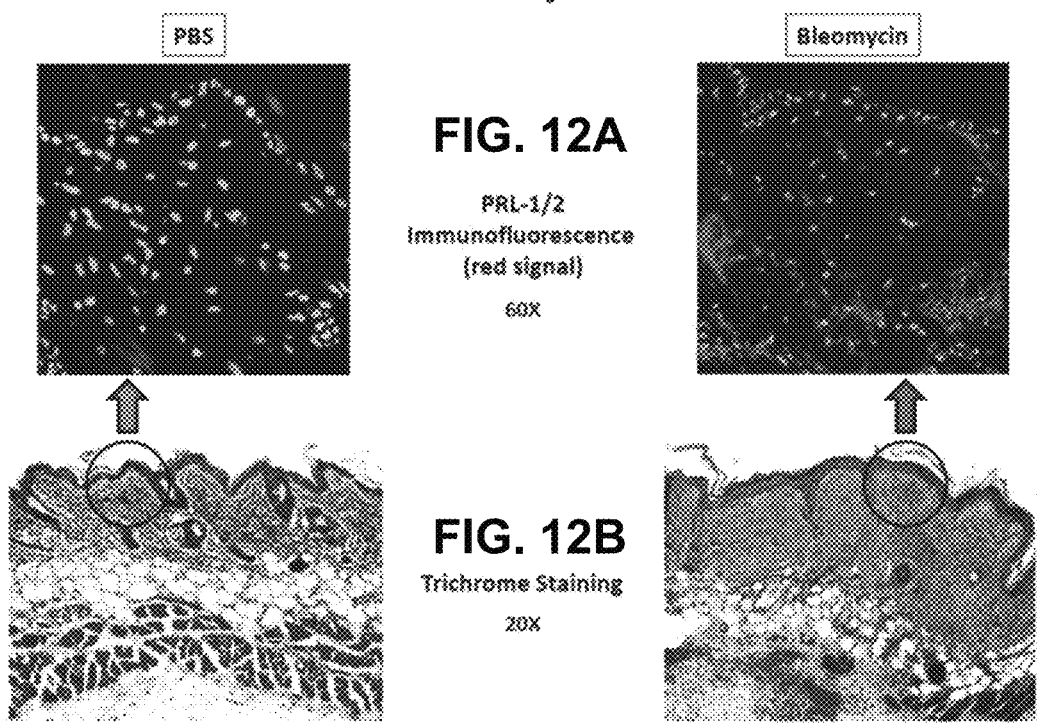

FIGS. 12A-12B show studies with a mouse Dermal sclerosis model. FIG. 12A shows PTP4A1/2 immunofluorescence (red signal) in skin sections of mice treated with PBS or bleomycin. Hoechst nuclear staining (blue signal). Images show overexpression of PTP4A1 and PTP4A2 (the Ab used is cross-reactive) in the model. FIG. 12B shows Masson's trichrome staining of skin slides of bleomycin-treated WT, PTP4A1 KO or PTP4A1 KO/PTP4A2 mice. The blue layer is the dermal collagen, increased in the model.

Figure 13:
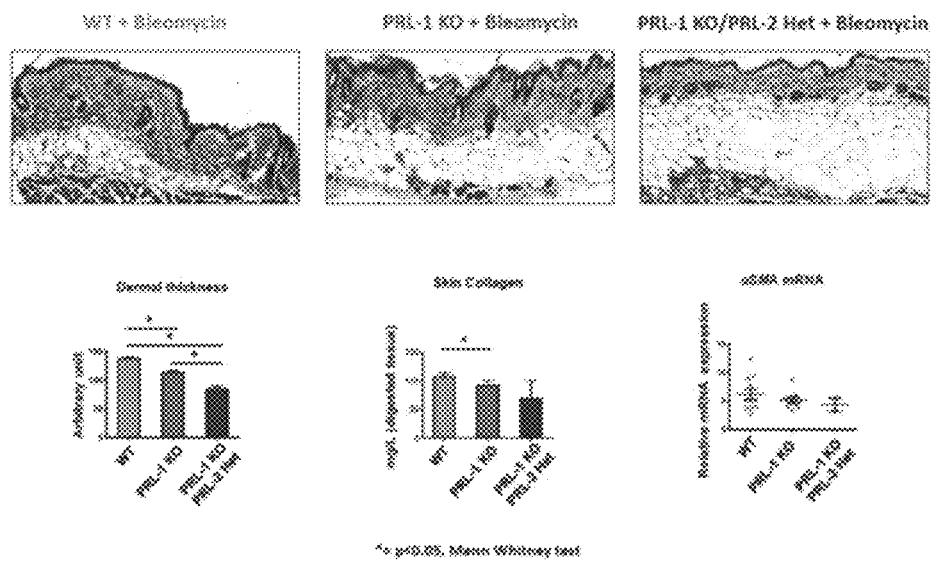

FIG. 13 shows studies with a Dermal sclerosis model in PTP4A1 knockout and PTP4A1 Knockout/PTP4A1 Het mice. Global KO of PTP4A1 led to a mild but significant protection from experimental skin fibrosis induced by injections of bleomycin. Mean±SEM shown. *, p<0.05, Mann-Whitney test.

FIGS. 14A-14F shows PTPs expression in dermal fibroblasts. FIG. 14 shows relative mRNA expression of all 109 PTP genes (FIG. 14A, Classical and atypical DSPs; FIG. 14B, Myotubularin DSPs; FIG. 14C, Class II, III, IV and novel PTPs; FIG. 14D, Slingshot, PRL CD14 and PTEN DSPs; FIG. 14E, Transmembrane PTPs; & FIG. 14F, Non-Receptor PTPs) as measured by qPCR in 4 SSc human dermal fibroblast lines. The * symbol indicates p<=0.05, Mann-Whitney test plus the ratio compared to mRNA relative expression of 5 healthy human dermal fibroblast lines.

FIGS. 15A-15E shows PTP4A1 is overexpressed in SSc dermal fibroblasts. FIG. 15A shows PTP4A1 expression as measured by qPCR in 14 healthy and SSc dermal fibroblast lines. FIG. 15B shows immunoblots for PTP4A1 and PTP4A2 in lysates of 5 healthy and 4 SSc dermal fibroblast lines. The graph shows mean±SEM of densitometric scan relative expressions plus representative immunoblots of PTP4A1/2 (upper bands) and alpha Tubulin (lower bands) in healthy and SSc patients. FIG. 15C shows PTP4A1/2 immunofluorescence (red signal) in skin sections of healthy or SSc Diffuse or Limited donors with Hoechst nuclear staining (blue signal). FIG. 15D shows a graph of mean±SEM of PTP4A1/2 fluorescence densitometric area scan in 6 healthy, 14 SSc diffuse, or 6 SSc limited donors. FIG. 15E, left panel shows dermal fibroblasts and keratinocytes excised from healthy or SSc skin paraffin-embedded samples by LCM after Hoechst nuclear staining (blue signal). FIG. 15E, right panels show PTP4A1 mRNA expression measured in excised fibroblasts or keratinocytes by qPCR in 6 healthy and 9 diffuse SSc donors. * indicates p<=0.05, Mann-Whitney test.

Figures 16A, 16B, 16C, 16D, 16E:
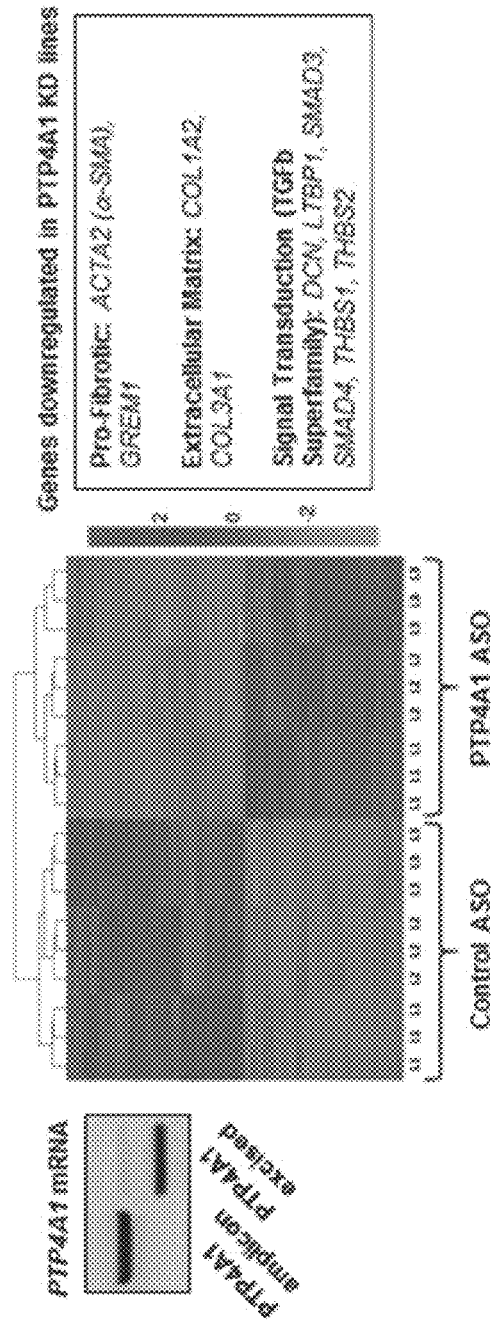

FIGS. 16A-16E shows silencing of PTP4A1 in NHDF causes downregulation of pro-fibrotic and TGFβ genes. FIG. 16A shows an image of an agarose gel with RT-PCR of PTP4A1 mRNA from NHDF treated with control ASO (left lane) or with PTP4A1 ASO (right lane). FIG. 16B shows a Heat Map of gene expression levels of 3 different lines (L 1-3) of NHDF treated with control ASO or PTP4A 1 ASO. Next Generation Sequencing (NGS) was performed in triplicate for each NHDF line. FIG. 16C shows a list of human fibrotic functional genes downregulated in PTP4A1 KD NHDF after DESeq analysis. FIGS. 16D-E, left graphs, shows mean±SEM of SMAD3 mRNA relative expression (FIG. 16D, left panel) and ACTA2 mRNA relative expression (FIG. 16E, left panel) measured by qPCR in 6 different lines of NHDF treated with control ASO or PTP4A1 ASO. FIGS. 16D-E, right graphs, show mean±SEM of densitometric scans of relative protein expression plus representative immunoblots of SMAD3 (FIG. 16D, upper insert, top bands), αSMA (FIG. 16E, upper insert, top bands) and GAPDH (FIGS. 16E and D, right panel, upper inserts, lower bands) in 6 different lines of NHDF treated with control ASO or PTP4A1 ASO. * indicates p<=0.05, Mann-Whitney test.

Figure 17:
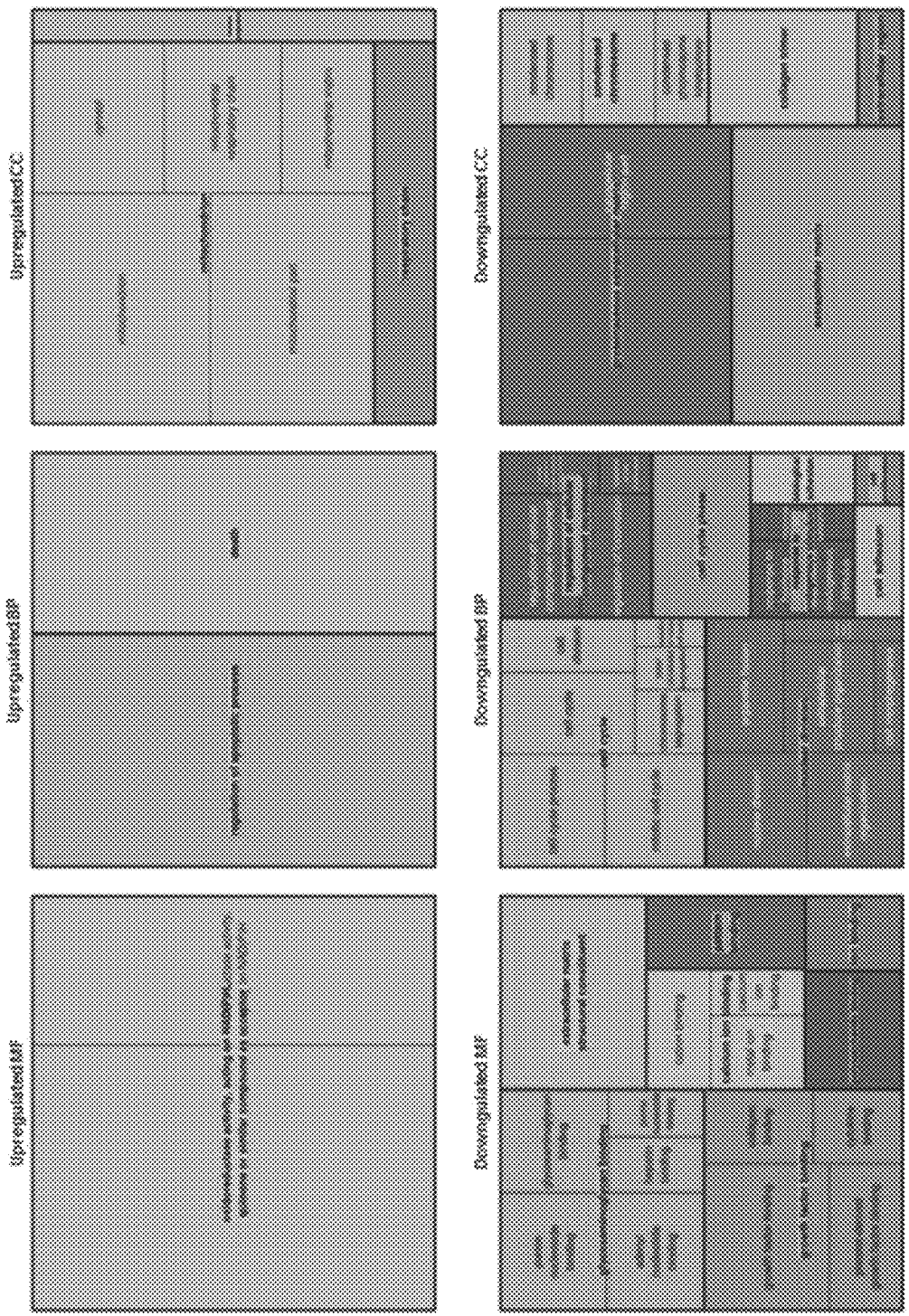

FIG. 17 shows molecular functions (MF), biological processes (BP), and cellular compartments (CC) analysis in PTP4A1 silenced NHDF. NGS data were analyzed with GO-Elite software. FIG. 17 images show pathway/GO term enrichment analysis for molecular functions (left upper and left lower panels), biological processes (middle upper and middle lower panels) and cellular compartments (right upper and right lower panels) in 3 different lines of NHDF treated with PTP4A1 ASO compared with the same lines treated with control ASO. Upper panels show pathways upregulated and lower panels show pathways downregulated in PTP4A1 silenced NHDF.

FIGS. 18A-18E shows PTP4A1 and PTP4A2 silencing in NHDF inhibits TGFβ pro-fibrotic signaling. FIGS. 18A-B graphs show mean±SEM mRNA relative expression of COL1A2 (FIG. 18A) and ACTA2 (FIG. 18B) measured by qPCR in 6 different lines of NHDF treated with control ASO or PTP4A1 ASO and then stimulated with TGFβ1. FIGS. 18C-D graphs show mean±SEM of COL1A2 (FIG. 18C) and ACTA2 (FIG. 18D) mRNA relative expression measured by qPCR in 3 different lines of NHDF treated with control ASO or PTP4A2 ASO and then stimulated with TGFβ1. FIG. 18E, left panel graph shows mean±SEM of SMAD3 mRNA relative expression measured by qPCR in 3 different lines of NHDF treated with control ASO or PTP4A2 ASO. FIG. 18E, right panel graph shows mean±SEM of densitometric scan relative expression plus representative immunoblots of SMAD3 (upper bands) and GAPDH (lower bands) in 3 different lines of NHDF treated with control ASO or PTP4A2 ASO. * indicates p<=0.05, Mann-Whitney test.

FIGS. 19A-19C shows NHDF silenced with a different PTP4A1 ASO (2) confirm the down regulation of TGFβ pro-fibrotic pathway. FIG. 19A images show agarose gels with RT-PCR of PTP4A1 (upper gel) and PTP4A2 (lower gel) mRNA from NHDF treated with control ASO (left lanes), PTP4A1 ASO2 or PTP4A2 ASO (right lanes). FIG. 19B left graph shows mean±SEM of densitometric scan relative expression plus representative immunoblots of SMAD3 (upper bands) and GAPDH (lower bands) in 6 different lines of NHDF treated with control ASO or PTP4A1 AS02. FIG. 19B, right graph shows mean±SEM of SMAD3 mRNA relative expression measured by qPCR in 6 different lines of NHDF treated with control ASO or PTP4A1 AS02. FIG. 19C graph shows mean±SEM of COL1A2 mRNA relative expression measured by qPCR in 6 different lines of NHDF treated with control ASO or PTP4A1 AS02 and then stimulated with TGFβ1. * indicates p<=0.05, Mann-Whitney test.

FIGS. 20A-20D shows PTP4A1 silencing inhibits TGFβ pro-fibrotic signaling in normal human lung fibroblasts (NHLF). FIG. 20A image shows agarose gel with RT-PCR of PTP4A1 mRNA from NHLF treated 7 days with control ASO (left lane) or with anti-PTP4A1 ASO (right lane). FIG. 20B graph shows mean±SEM of SMAD3 mRNA relative expression measured by qPCR in 3 different lines of NHLF treated for 7 days with control ASO or anti-PTP4A1 ASO. FIGS. 20C-D graphs show mean±SEM of COL1A2 and ACTA2 mRNA relative expression measured by qPCR in 3 different lines of NHLF treated for 7 days with control ASO or anti-PTP4A1 ASO and then stimulated for 24 h with 20 ng/ml TGFβ1. * indicates p<=0.05, Mann-Whitney test.

Figure 21A:
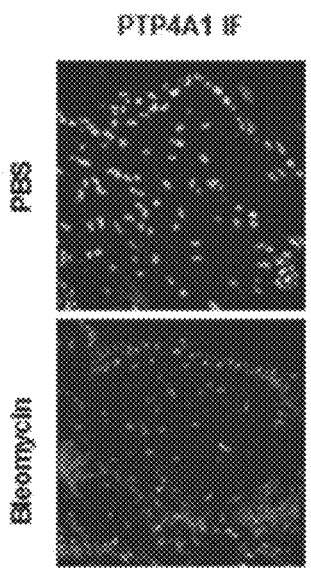
Figure 21B:
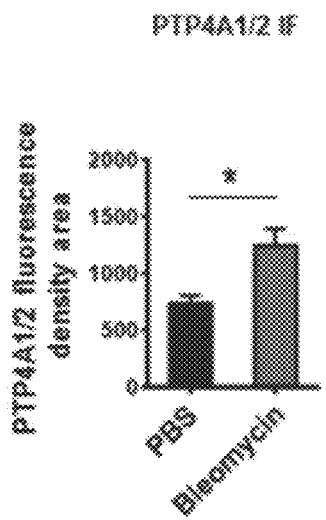
Figure 21C:
Figure 21D:
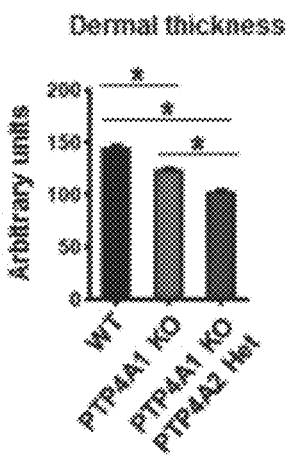
Figure 21E:
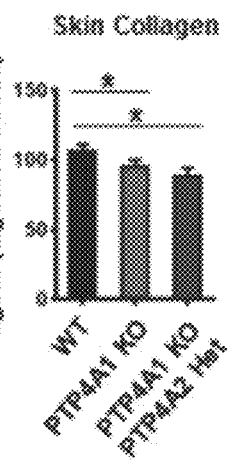
Figure 21F:
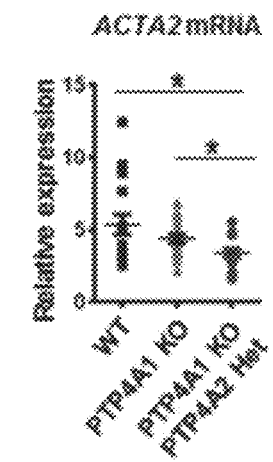

FIGS. 21A-21F shows PTP41/2 silencing reduces fibrosis in in vivo Bleomycin model. FIG. 21A shows PTP4A1/2 immunofluorescence (red signal) in skin sections of B6 mice subcutaneous injected every other day with PBS or 50 micrograms bleomycin for 2 weeks. Hoechst nuclear staining (blue signal). FIG. 21B graph shows mean±SEM of PTP4A1/2 fluorescence densitometric area scan. FIG. 21C Masson's trichrome staining of skin slides of bleomycin-treated 16 WT, 16 PTP4A1 KO or 14 PTP4A1 KO/PTP4A2 Het mice. FIGS. 21D-F graphs show mean±SEM of dermal thickness, skin collagen concentration and ACTA2 mRNA relative expression in skin samples. *, p<=0.05, Mann-Whitney test.

FIGS. 22A-22B shows PTP4A1 influences SMAD3 localization. FIG. 22A graph shows mean±SEM of densitometric scan relative expression plus representative immunoblots of pSMAD3 S423/425 (upper bands) and SMAD3 (lower bands) in 6 different lines of NHDF treated with control ASO or PTP4A1 ASO and then stimulated with TGFβ1. FIG. 22B left panels show SMAD3 immunofluorescence (red signal) in NHDF treated with control ASO or PTP4A1 ASO and then stimulated with TGFβ1. Hoechst staining was used to visualize nuclei (blue signal). FIG. 22B right panel shows mean±SEM of SMAD3 nuclear or cytoplasmatic fluorescence densitometric area scan in 3 control ASO or 3 PTP4A1 ASO treated NHDF lines stimulated with TGFβ1. * indicates $p<=0.05$, Mann Whitney test.

FIGS. 23A-23F shows PTP4A1 influences TGFβ profibrotic signaling through SMAD3. FIG. 23A graph shows COL1A2 promoter relative expression in 6 different lines of NHDF treated with control ASO or PTP4A1 ASO and then stimulated with TGFβ1. pSMAD3 antibody was used to perform the ChIP. FIG. 23B graphs show mean±SEM of ratio between SMAD3 nuclear or cytoplasmatic fluorescence densitometric area scan in 3 control ASO or PTP4A1 ASO treated NHDF lines stimulated with TGFβ1. FIG. 23C graph shows mean±SEM of SMAD3 mRNA relative expression measured by qPCR in triplicate in 1 line of NHDF treated with 50 microM DMSO or SCH772984 ERK inhibitor. FIG. 23D graphs show mean±SEM of densitometric scan relative expression plus representative immunoblots of pERK1/2 T202/Y204 (upper bands) and ERK2 (lower bands) in 3 different lines of NHDF treated with control ASO, PTP4A1 ASO (left graph) or PTP4A2 ASO (right graph). FIG. 23E, left graph shows mean±SEM of relative ratio of Firefly/*Renilla* luciferase signal of HEK 293T cells co-transfected with human PTP4A1 WT or PTP4A2 WT-encoding HA-tag pCDNA4 vectors together with a firefly luciferase SMAD reporter and a control luciferase *Renilla* vector. Cells were stimulated with TGFβ1. Graph is representative of 6 independent experiments. FIG. 23E, right graph shows densitometric scan relative expression plus representative immunoblots of HA-tagged PTP4A1/2 (upper bands) and GAPDH (lower bands) in HEK 293T cells co-transfected with human PTP4A1 WT or PTP4A2 WT-encoding HA-tag pCDNA4. FIG. 23F graph shows ROCK kinase activity in 3 different lines of NHDF treated with control ASO, PTP4A1 (left graph), or PTP4A2 ASO (right graph) and then stimulated with TGFβ1. * indicates $p<=0.05$, Mann-Whitney test.

FIGS. 24A-24F shows PTP4A1 promotes SMAD3 expression and nuclear localization in NHDF by enhancing SRC half-life. FIGS. 24A-C graphs show mean±SEM of densitometric scan relative expression plus representative immunoblots of pMEK1/2 S217/221, pMEK1/2 S217/221 or pPLCgY783 (upper bands) and MEK1/2 or GAPDH (lower bands) in 3 different lines of NHDF treated with control ASO, PTP4A1 ASO. FIGS. 24D-E, left graphs show mean±SEM of densitometric scan relative expression plus representative immunoblots of SRC (upper bands) and GAPDH (lower bands) in 6 or 3 different lines of NHDF treated with control ASO, PTP4A1 ASO or PTP4A2 ASO. FIGS. 24D-E, right graphs show mean±SEM of SRC mRNA relative expression measured by qPCR in 6 or 3 different lines of NHDF treated with control ASO, PTP4A1 ASO, or PTP4A2 ASO. FIG. 24F graphs show mean±SEM of densitometric scan relative expression plus representative immunoblots of pSRC Y416 (left graph, upper bands) or Y527 (right graph, upper bands) and SRC (lower bands) in 3 different lines of NHDF treated with control ASO, PTP4A1 ASO. * indicates $p<=0.05$, Mann-Whitney test.

FIG. 25 shows phosphatase dead PTP4A1 ASO (3) product. FIG. 25A image shows, on the left, agarose gel with RT-PCR of PTP4A1 mRNA from NHDF treated with control ASO (left lanes) or PTP4A1 ASO3 (right lanes) and, on the right, the 3D structure of PTP4A1 from PDB database. In yellow is shown the region where PTP4A1 AS03 eliminates exon 4, between residues G109 and K136. FIG. 25B shows PTP4A1 WT (SEQ ID NO:1) and PTP4A1 ASO3 (SEQ ID NO:7) complete amino acid sequences. Exon 1, 3 and 5 are represented in black and exons 2 and 4 in blue.

FIGS. 26A-26G shows PTP4A1 enhances SRC half-life in NHDF through inhibition of basal autophosphorylation. FIG. 26A graph shows mean±SEM of relative ratio of Firefly/*Renilla* luciferase signal of HEK 293T cells co-transfected with human PTP4A1 WT, PTP4A1 C104S phosphatase dead or PTP4A1 G97R lacking of trimerization-encoding HA-tag pCDNA4 vector together with a firefly luciferase SMAD reporter and a control luciferase *Renilla* vector. Cells were stimulated with TGFβ1. Graph is representative of 3 independent experiments. FIGS. 26B-D graphs show mean±SEM of densitometric scan relative expression plus representative immunoblots of pSRC Y416 (upper bands) and SRC (lower bands) in 3 different in vitro Src kinase assay followed by incubation with or in presence of PTP4A1 or PTP4A2. FIG. 26C graph shows mean±SEM of densitometric scan relative expression plus representative immunoblots of PTP4A1/2 (upper bands) and SRC (lower bands) in 2 different in vitro Src trapping assay in presence of PTP4A1 or PTP4A2. FIGS. 26E, 26F and 26G graphs show mean±SEM of SMAD3 or SRC mRNA relative expression measured by qPCR or densitometric scan relative expression plus representative immunoblots of SMAD3, SRC, pERK1/2 T202/Y204 (upper bands) and GAPOH (lower bands) in 3 different lines of NHDF treated with control ASO or PTP4A1. * indicates $p<=0.05$, Mann-Whitney test.

Figure 27A:
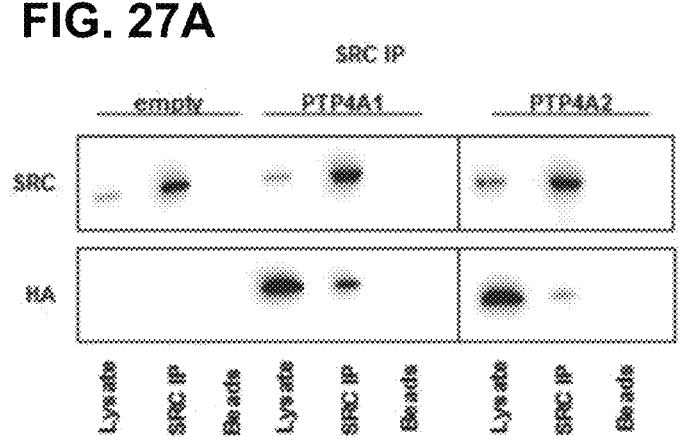
Figure 27B:
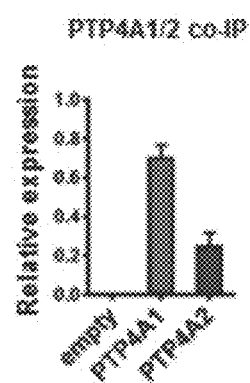

FIGS. 27A-27B shows PTP4A1 co-precipitates with SRC in HEK 293T cells. FIG. 27A shows an immunoblot of SRC (upper bands) and HA (lower bands) in HEK 293T cells co-transfected with empty, PTP4A1 C104S or PTP4A2 C101S HA-tag pCDNA4 vectors. Lysates were immunoprecipitated (IP) with anti-SRC antibody on protein G beads. FIG. 27B graph shows mean±SD of densitometric scan relative expression of HA co-IP in HEK 293T cells cotransfected with empty, PTP4A1 C104S or PTP4A2 C101S HA-tag pCDNA4 vectors. Graph is representative of 2 independent experiments.

Figure 28:
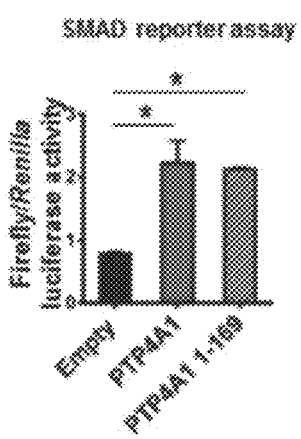

FIG. 28 shows PTP4A1 mutant does not influence SMAD signaling pathway. FIG. 28 graph shows mean±SEM of relative ratio of Firefly/*Renilla* luciferase signal of HEK 293T cells co-transfected with human PTP4A1 WT or PTP4A1 1-169 lacking of membrane association-encoding HA-tag pCDNA4 vector together with a firefly luciferase SMAD reporter and a control luciferase *Renilla* vector. Cells were stimulated with TGFβ1 24 h. * indicates $p<0.05$, Mann-Whitney test of 3 biological replicates.

FIGS. 29A-29E shows magnesium does not influence the TGFβ-SMAD3 signaling. FIG. 29A graph shows mean±SEM of SMAD3 mRNA relative expression measured by qPCR in 3 different lines of NHDF treated with control ASO or PTP4A 1 ASO and incubated in Mg starved media. FIG. 29B graphs show mean±SEM of SMAD3 mRNA relative expression measured by qPCR in 3 different lines of NHDF treated with control ASO or PTP4A1 ASO, incubated in Mg starved media and then stimulated with TGFβ1. FIG. 29C graph shows mean±SEM of relative ratio of Firefly/*Renilla* luciferase signal of HEK 293T cells co-transfected with human PTP4A1 WT-encoding HA-tag pCDNA4 vector together with a firefly luciferase SMAD reporter and a control luciferase *Renilla* vector. Cells were incubated in normal or Mg starved media and stimulated with TGFβ1. Graph is representative of 3 independent experiments. FIG. 29D graph shows mean±SEM ratio of PTP4A1/empty Firefly/*Renilla* luciferase signal. FIG. 29E, left graph shows mean±SD of CNNM4 mRNA relative expression measured by qPCR in HEK293T cells treated with scramble or anti-CNNM4 siRNA. FIG. 29E, right graph shows mean±SD of relative ratio of Firefly/*Renilla* luciferase signal of HEK 293T cells co-transfected with human scramble or anti-CNNM4 siRNA together with a firefly luciferase SMAD reporter and a control luciferase *Renilla* vector. Cells were stimulated with TGFβ1. Graphs are representative of 2 independent experiments. * indicates p<0.05, Mann-Whitney test.

DETAILED DESCRIPTION

As disclosed herein, mRNA expression profile of all the PTPs (109 genes) in primary dermal fibroblasts from SSc patients were analyzed and compared to healthy subjects. Whole transcriptome analysis by Next Generation Sequencing (NGS) was performed on normal human dermal fibroblasts (NHDF) subjected to silencing of the PTP4A1 gene. In NHDF the effects of PTP4A1 silencing on TGFbeta1 stimulated COL 1A2 and ACTA2 gene expression and on SMAD3 and alphaSMA protein level was investigated by qPCR and immunoblot, respectively. Luciferase assays were performed using a SMAD reporter in HEK 293T cell and in vivo studies were carried out in mice using a bleomycin-induced fibrosis model.

The PTP4A1 gene was found overexpressed in 14 SSc dermal fibroblast lines compared to 14 lines from healthy subjects (Mann-Whitney test, p<0.05). NGS of normal dermal fibroblasts showed that silencing of PTP4A1 correlated with reduced expression of human pro-fibrotic genes and in particular of SMAD3, which indicates a potential role of PTP4A1 in the TGFbeta-dependent pro-fibrotic pathway. NGS data for SMAD3 and other pro-fibrotic genes were confirmed at the protein level by immunoblotting. Co-transfection of HEK293T with a human PTP4A1-encoding pCDNA4 vector together with a luciferase SMAD reporter showed that PTP4A1 enhances activation of SMAD signaling after TGFbeta1 stimulation (Mann-Whitney test, p<0.05). In vivo studies showed that knockout of PTP4A1 significantly attenuates bleomycin-induced fibrosis model in mice.

The foregoing results indicate that PTP4A1, a PTP overexpressed in SSc dermal fibroblasts, plays a role in the pathogenesis of SSc by promoting pro-fibrotic TGFbeta/SMAD3 signaling. Inhibiting, suppressing, reducing or blocking PTP4A1 expression or activity can be used, for example, to inhibit or suppress pathology of fibrotic diseases and disorders such as organ or skin fibrosis in SSc.

The invention therefore provides methods of modulating protein tyrosine phosphatase 4A1 (PTP4A1) expression or activity. The invention also provides methods of modulating a pathology of systemic sclerosis. The invention further provides methods of treating systemic sclerosis in a subject. In various embodiments, a method includes contact or administration of an effective amount of modulator of protein tyrosine phosphatase 4A1 (PTP4A1) to a subject sufficient to modulate protein tyrosine phosphatase 4A1 (PTP4A1) expression or activity; to modulate a pathology of systemic sclerosis; and to treat systemic sclerosis. In particular embodiments, a method includes contacting or administering a sufficient amount of an antagonist or an inhibitor of PTP4A1 to a subject to reduce or inhibit a fibrotic disease or disorder, such as organ or skin fibrosis.

As disclosed herein, methods and uses include modulating PTP4A1 protein or nucleic acid function, activity or expression. Methods and uses can be performed in vivo, such as in a subject, in vitro, ex vivo, in a cell, in solution, in solid phase or in silica. In one embodiment, a method or use includes contacting an agent, such as an antagonist of PTP4A1 protein or nucleic acid sufficient to modulate PTP4A1 protein or nucleic acid function, activity or expression.

As used herein, the term "modulate," means an alteration of or effect on the term modified. For example, the term modulate can be used in various contexts to refer to an alteration of or effect on an activity, a function, or expression of a polypeptide, gene or signaling pathway, or a physiological condition or response of an organism. Methods and uses include modulating one or more functions, activities or expression of PTP4A1 protein or nucleic acid, in solid phase, in a cell, in vitro, ex vivo or in vivo.

Where the term "modulate" is used to modify the term "protein" this means that the referenced protein activity, function, or expression is altered or affected (e.g., decreased, reduced, inhibited, suppressed, limited, controlled or prevented, etc.). Detecting an alteration or an effect on protein activity, function or expression, can be determined as set forth herein using assays, such as cell based, in vitro or in vivo assays.

A modulator that is an "antagonist or inhibitor of PTP4A1" means an agent (molecule) that directly or indirectly inhibits, reduces, decreases, suppresses, limits, controls or prevents expression, activity or function of PTP4A1. Antagonists/inhibitors therefore include agents (molecules) that bind to PTP4A1 as well as agents (molecules) that bind to a PTP4A1 receptor or target. Antagonists/inhibitors also include agents (molecules) that bind to PTP4A1 protein or nucleic acid sequences, as well as agents (molecules) that bind to PTP4A1 receptor or target protein or nucleic acid sequences.

A non-limiting representative example of human PTP4A1 sequence (SEQ ID NO:1) as a target for an antagonist/inhibitor is as set forth below:

```
MARMNRPAPVEVTYKNMRFLITHNPTNATLNKFIEELKKYGVTTIVRVC

EATYDTTLVEKEGIEVLDWPFDDGAPPSNQIVDDWLSLVKIKFREEPGC

CIAVHCVAGLGRAPVLVALALIEGGMKYEDAVQFIRQKRRGAFNSKQLL

YLEKYRPKMRLRFKDSNGHRNNCCIQ
```

In certain embodiments, a PTP4A1 protein comprises a full length PTP4A1 protein. In certain embodiments, a PTP4A1 protein comprises a partial PTP4A1 protein sequence. In some embodiments, a PTP4A1 protein may retain the full functionality of an endogenous PTP4A1 protein. In certain embodiments, a PTP4A1 protein may comprise partial functionality of an endogenous PTP4A1 protein sequence. In some embodiments a PTP4A1 protein or polypeptide comprises between about 15 and 250 amino acids in length, between about 15 and 173 amino acids in length, between about 15 and 100 amino acids in length, between about 15 and 50 amino acids in length, between about 15 and 30 amino acids in length, between about 50 and 250 amino acids in length or between about 165 to about 180 amino acids in length. In some embodiments a PTP4A1 protein or polypeptide consists of a polypeptide about 173 amino acids in length.

In certain embodiments, a PTP4A1 protein is a human PTP4A1 protein or a homologue thereof. In some embodiments a PTP4A1 polypeptide comprises a polypeptide amino acid sequence having at least 60% identity, at least 70% identity, at least 80% identity, at least 85% identity, at least 90% identity, at least 95% identity, or 100% identity to the PTP4A1 amino acid sequence of SEQ ID NO:1. A homologue of a human PTP4A1 protein can be a PTP4A1 protein homologue found in any species of mammal. In some embodiments a homologue of a human PTP4A1 protein is an endogenous or wild-type PTP4A1 protein found in a rodent, dog, cat, pig, cow, horse, or the like.

The term "percent identical" refers to sequence identity between two amino acid sequences. Identity can be determined by comparing a position in each two sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. An alignment program that permits gaps in the sequence can be utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

A non-limiting representative example of human PTP4A1 nucleic acid as a target for an antagonist/inhibitor is a cDNA as set forth below (SEQ ID NO: 2)
ATGGCTCGAATGAACCGCCCAGCTCCTGTGGAAGTCACATACAAGAACA

TGAGATTTCTTATTACACACAATCCAACCAATGCGACCTTAAACAAATT

TATAGAGGAACTTAAGAAGTATGGAGTTACCACAATAGTAAGAGTATGT

GAAGCAACTTATGACACTACTCTTGTGGAGAAAGAAGGTATCCATGTTC

TTGATTGGCCTTTTGATGATGGTGCACCACCATCCAACCAGATTGTTGA

TGACTGGTTAAGTCTTGTGAAAATTAAGTTTCGTGAAGAACCTGGTTGT

TGTATTGCTGTTCATTGCGTTGCAGGCCTTGGGAGAGCTCCAGTACTTG

TTGCCCTAGCATTAATTGAAGGTGGAATGAAATACGAAGATGCAGTACA

ATTCATAAGACAAAAGCGGCGTGGAGCTTTTAACAGCAAGCAACTTCTG

TATTTGGAGAAGTATCGTCCTAAAATGCGGCTGCGTTTCAAAGATTCCA

ACGGTCATAGAAACAACTGTTGCATTCAATAA, or an mRNA corresponding thereto.

In certain embodiments, a PTP4A1 protein is a PTP4A1 protein encoded by the cDNA of SEQ ID NO:2, or a PTP4A1 protein encoded by a cDNA nucleic acid sequence having at least 60% identity, at least 70% identity, at least 80% identity, at least 85% identity, at least 90% identity, at least 95% identity, or 100% identity to the PTP4A1 nucleic acid sequence of SEQ ID NO:2.

The term "contact" and grammatical variations thereof means a physical or functional interaction between one entity and one or more other entities. In the methods and uses herein, contact can occur in solution, in solid phase, in vitro, ex vivo or in vivo (i.e., in a subject).

An example of physical contact is a direct or indirect binding, such as between a PTP4A1 antagonist and a target gene or protein (e.g., PTP4A1). The term "bind" or "binding" used in reference to an interaction between two entities means that there is a physical interaction at the molecular level.

A functional interaction need not require physical binding. An example of a functional interaction is where an intermediate facilitates or mediates a change in activity of one entity by another entity, such as a signaling pathway where molecules within the pathway functionally interact but need not physically contact each other.

An antagonist/inhibitor that binds to PTP4A1 (PTP4A1 protein or nucleic acid), means that the antagonist/inhibitor has affinity for PTP4A1 protein or nucleic acid. "Specific binding" is where the binding is selective between the two referenced molecules. Thus, specific binding of an antagonist/inhibitor for PTP4A1 is that which is selective for PTP4A1.

Typically, specific binding can be distinguished from non-specific when the dissociation constant ($K_D$) is less than about $1 \times 10^{-5}$M or less than about $1 \times 10^{-6}$M or $1 \times 10^{-7}$ M. Selective binding can be distinguished from non-selective binding using assays known in the art (e.g., nucleic acid hybridization, immunoprecipitation, ELISA, Western blotting, functional/activity/expression assays) with appropriate controls.

As used herein, the terms "peptide," "polypeptide" and "protein" are used interchangeably and refer to two or more amino acids covalently linked by an amide bond or non-amide equivalent. Polypeptides include full length native polypeptide, and "modified" forms such as subsequences, variant sequences, fusion/chimeric sequences and dominant-negative sequences.

Peptides include L- and D-isomers, and combinations thereof. Peptides can include modifications typically associated with post-translational processing of proteins, for example, cyclization (e.g., disulfide or amide bond), phosphorylation, glycosylation, carboxylation, ubiquitination, myristylation, acetylation (N-terminal), amidation (C-terminal), or lipidation. Polypeptides described herein further include compounds having amino acid structural and functional analogues, for example, peptidomimetics having synthetic or non-natural amino acids or amino acid analogues, so long as the mimetic has one or more functions or activities of a native polypeptide set forth herein. Non-natural and non-amide chemical bonds, and other coupling means can also be included, for example, glutaraldehyde, N-hydroxysuccinimide esters, bifunctional maleimides, or N, N'-dicyclohexylcarbodiimide (DCC). Non-amide bonds can include, for example, ketomethylene aminomethylene, olefin, ether, thioether and the like (see, e.g., Spatola (1983) in *Chemistry and Biochemistry of Amino Acids, Peptides and Proteins*, Vol. 7, pp 267-357, "Peptide and Backbone Modifications," Marcel Decker, NY).

A subsequence or fragment of polypeptide includes or consists of one or more amino acids less than full length polypeptide. The term "subsequence" or "fragment" means a portion of the full length molecule. A subsequence of a polypeptide sequence has one or more one or more internal or terminal amino acid deletions from either amino or carboxy-termini). Subsequences therefore can be any length up to the full length native molecule, provided said length is at least one amino acid less than full length native molecule.

Subsequences can vary in size, for example, from a polypeptide as small as an epitope capable of binding an antibody or binding/activating T cells (i.e., about five to about eight amino acids) up to a polypeptide that is one amino acid less than the entire length of a reference polypeptide. Non-limiting exemplary subsequences less than full length include, for example, a subsequence from about 5 to 10, 10 to 20, 20 to 30, 30 to 50, 50 to 100, 100 to 150, 150 to 200, 200 to 250, 250 to 300, 300 to 400, or 400 to 500, amino acids in length.

Polypeptides and subsequences may also include or consist of one or more amino acid additions or deletions, wherein the subsequence does not comprise full length sequence. Accordingly, total subsequence lengths can be greater than the length of full length native/wild type polypeptide, for example, where a subsequence is fused or forms a chimera with another heterologous polypeptide.

The terms "polynucleotide" and "nucleic acid" are used interchangeably to refer to all forms of nucleic acid, oligonucleotides, primers, and probes, including deoxyribonucleic acid (DNA) and ribonucleic acid (RNA). Polynucleotides include genomic DNA, cDNA and antisense DNA, and spliced or unspliced mRNA, rRNA, tRNA and antisense RNA (e.g., RNAi, siRNA, miRNA). Polynucleotides include naturally occurring, synthetic, and intentionally altered or modified polynucleotides as well as analogues and derivatives. Alterations can result in increased stability due to resistance to nuclease digestion, for example. Polynucleotides can be double, single or triplex, linear or circular, and can be of any length.

Polynucleotides include sequences that are degenerate as a result of the genetic code. There are 20 natural amino acids, most of which are specified by more than one codon.

Polynucleotide sequences include sequences having 15-20, 20-30, 30-40, 40-50, 50-75, 75-100, 100-150, 150-200, or more contiguous nucleotides. In additional aspects, the polynucleotide sequence includes a sequence having 200 or more, 250 or more, 300 or more, 400 or more, 500 or more, up to the full length coding sequence.

Polynucleotide sequences include complementary sequences such as antisense. Such sequences may optionally be encoded by a nucleic acid and such a nucleic acid may be operatively linked to an expression control element for expression of the encoded antisense in cells in vitro or in vivo.

Polynucleotides can be obtained using various standard cloning and chemical synthesis techniques. Purity of polynucleotides can be determined through sequencing, gel electrophoresis and the like. For example, nucleic acids can be isolated using hybridization as set forth herein or computer-based database screening techniques known in the art. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Exemplary PTP4A1 antagonists/inhibitors include, for example, small molecules such as an organic compound (e.g., drugs) less than about 1 kDa, less than about 500 Da, less than about 400 Da, less than about 300 Da, less than about 200 Da, or less than about 100 Da in molecular weight. Small molecules can therefore be from about 10-25 Da, 25-50 Da, 50-100 Da, 100-200 Da, 200-300 Da, 300-400 Da, 400-500 Da, 500-600 Da, 600-750 Da or 750-1,000 Da in molecular weight.

Additional antagonists/inhibitors include sequences such as PTP4A1 polypeptide and nucleic acid subsequences/fragments. Subsequences and fragments refer to polypeptides and nucleic acids having one or more fewer amino acids/nucleotides in comparison to a reference (e.g., native or wild-type PTP4A1) polypeptide/nucleic acid sequence. A subsequence that binds to PTP4A1 protein or nucleic acid, or a PTP4A1 target protein or nucleic acid can retain at least a part of its binding activity. A non-limiting example is a dominant negative PTP4A1 protein (e.g., subsequence) or an inhibitory nucleic acid that binds to PTP4A1 nucleic acid sequence (e.g., genomic, pre-mRNA or mRNA PTP4A1 sequence).

Further antagonists/inhibitors include sequences such as PTP4A1 chimeras/fusions. A "chimera" or "fusion," when used in reference to a sequence means that the sequence contains one or more portions that are based upon, derived from, or obtained or isolated from, two or more different proteins or nucleic acids, i.e. are heterologous with respect to each other. That is, for example, a portion of the sequence may be based upon or from one particular protein or nucleic acid (e.g., PTP4A1), and another portion of the sequence may be based upon or from a different protein or nucleic acid, e.g., distinct from PTP4A1. Thus, a fusion or chimeric sequence is a molecule in which different portions of the sequence are of different origins.

The term "heterologous," when used in reference to a sequence, means that the sequence is not normally contiguous with the other polypeptide or nucleic acid in its natural environment. Thus, a chimeric polypeptide means that a portion of the polypeptide does not exist fused with the other polypeptide. In other words, a chimeric sequence is a molecule that does not normally exist in nature, i.e., such a molecule is produced by the hand of man, e.g., artificially produced through recombinant DNA technology.

In certain embodiments, presented herein is an antibody, or binding fragment thereof, that specifically binds to a PTP4A1 protein, or a portion thereof. In some embodiments, an agent that modulates activity of PTP4A1 is an antibody or binding fragment thereof, that specifically binds to a PTP4A1 protein, or a portion thereof. In some embodiments, an agent that modulates a pathology of a fibrotic disease or disorder (e.g., systemic sclerosis) in a subject is an antibody, or binding fragment thereof, that specifically binds to a PTP4A1 protein, or a portion thereof. In some embodiments, an antagonist of a PTP4A1 protein is an antibody, or binding fragment thereof, that specifically binds to a PTP4A1 protein, or a portion thereof.

The term "specifically binds" refers to a binding agent binding to a target peptide in preference to binding other molecules or other peptides as determined using a suitable assay (e.g., an Elisa, Immunoblot, Flow cytometry, and the like). A specific binding interaction discriminates over non-specific binding interactions by about 2-fold or more, often about 10-fold or more, and sometimes about 50- or 100-fold or more, 500- or 1000-fold or more, 5,000- or 10,000-fold or more, 50,000- or 100,000-fold or more, or 500,000- or 1,000,000-fold or more.

Further antagonists/inhibitors include an antibody that binds to PTP4A1 or PTP4A1 antibody. An "antibody" means any monoclonal or polyclonal immunoglobulin molecule, such as IgM, IgG, IgA, IgE, IgD, and any subclass thereof, or any isotype thereof (e.g., lgG1, lgG2a, lgG2b or lgG3), which includes intact immunoglobulin molecules, two full length heavy chains linked by disulfide bonds to two full length light variable domains, $V_H$ and $V_L$, individually or in any combination, as well as subsequences, such as Fab, Fab', (Fab')$_2$, Fv, Fd, scFv and sdFv, unless otherwise expressly stated. An antibody can be a natural antibody, a polyclonal antibody, a monoclonal antibody, a recombinant antibody, a chimeric antibody, a bi-specific antibody, a CDR-grafted antibody, a humanized antibody, a human antibody, the like, or a combination thereof. Methods for generating chimeric and humanized antibodies are known (see, e.g., U.S. Pat. No. 5,530,101 (Queen, et al.), U.S. Pat. No. 5,707,622 (Fung, et al.) and U.S. Pat. Nos. 5,994,524 and 6,245,894 (Matsushima, et al.)) In some embodiments, an antibody, or binding fragment thereof, is a Fab, Fab', F(ab')2, Fv fragment, scFv, diabody, aptamer, synbody, camelid, DARPin, affibody, the like and/or combinations thereof.

"Monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced.

Antibodies include kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa and two lambda light chains. The primary difference between kappa and lambda light chains is in the sequences of the constant region.

Antibodies include mammalian, human, humanized, or primatized forms of heavy or light chain, $V_H$ and $V_L$, respectively, immunoglobulin (Ig) molecules. An exemplary PTP4A1 antibody is an antibody that binds to human PTP4A1.

Monoclonal antibodies are made by methods known in the art (Kohler et al., Nature, 256:495(1975); and Harlow and Lane, Using Antibodies: A Laboratory Manual, Cold Spring Harbor Laboratory, 1999). Briefly, monoclonal antibodies can be obtained by injecting a mouse, one or multiple times, with an antigen (e.g., PTP4A1, or a portion thereof), often combined with a suitable adjuvant. The polypeptide or peptide used to immunize an animal may be derived from translated DNA or chemically synthesized and conjugated to a carrier protein. Commonly used carriers which are chemically coupled to the immunizing peptide include, for example, keyhole limpet hemocyanin (KLH), thyroglobulin, bovine serum albumin (BSA), and tetanus toxoid. Antibody production is verified by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from hybridoma cultures. Monoclonal antibodies can be isolated and purified from hybridoma cultures by a variety of established techniques which include, for example, affinity chromatography with Protein-A Sepharose, size-exclusion chromatography, and ion-exchange chromatography (see e.g., Coligan et al., Current Protocols in Immunology sections 2.7.1-2.7.12 and sections 2.9.1-2.9.3; and Barnes et al., "Methods in Molecular Biology," 10:79-104, Humana Press (1992)).

Candidate anti-PTP4A1 antibodies can be tested and selected for specific binding and/or activity (e.g., antagonist activity) using a suitable assay. As a first screen, antibodies can be tested for specific binding to the antigen utilized to produce them, or against the entire PTP4A1 protein, or a portion thereof. As a second screen, candidates may, in certain embodiments, be tested for specific binding to an appropriate cell line that expresses a PTP4A1 protein. After selective binding is established, a candidate antibody that displays specific binding to a PTP4A1 protein may be tested for activity using a suitable assay, and candidate antibodies that possess a desired activity can readily be identified. Antibody activity can be tested in vitro, using a suitable cell type, or using an in vivo model. In some embodiments, antagonist activity of an anti-PTP4A1 antibody can be assessed by testing the ability of an antibody to inhibit a tyrosine phosphatase enzymatic activity of a PTP4A1 protein. In certain embodiments, antagonist activity of an anti-PTP4A1 antibody can be assessed in vivo by determining the ability of an anti-PTP4A1 antibody to decrease, reduce, suppress, inhibit, limit or control a pathology, or undesirable or adverse symptom of a fibrotic disease or disorder (e.g., a pathology, or undesirable or adverse symptom of systemic sclerosis). In some embodiments, antibody activity can be assessed by testing the ability of an antibody to inhibit any one of the functions of PTP4A1, or functions that are associated with PTP4A1, that are identified herein (e.g., see Examples 4-7). In certain embodiments, an antagonist antibody, or binding fragment thereof, that specifically binds to PTP4A1 can be tested for the ability to decrease, reduce, suppress, inhibit, limit or control a pathology, or undesirable or adverse symptom of a fibrotic disease or disorder using the mouse model of dermal sclerosis described herein (e.g., see Example 8).

In certain embodiments, an anti-PTP4A1 antibody that can be used for a method described herein is an antibody described in U.S. Patent Application Publication No. 2011/

0206657 (hereafter, the '657 application). For example, antibodies 269 and/or 223 which are described in the '657 application can be used for a method described herein.

For example, in certain embodiments, an antagonist anti-PTP4A1 antibody comprises the amino acid sequence of the heavy chain variable region of monoclonal antibody 269 as follows (SEQ ID NO: 3)
EFMKCSWVILFLFSVTAGVHSQVQFQQSGAELAKPGASVKMSCKASG

YTFTSYRMHWVKQRPGQGLEWIGYINPSTGYTEYNQKFKDKATLTAD

KSSSTAYMQLSSLTSEDSAVYYCSSYGNFGYWGQGTTLTVSSESQSF

PNVFPLVSLG

In certain embodiments, an antagonist anti-PTP4A1 antibody comprises the amino acid sequence of the light chain variable region of monoclonal antibody 269 as follows (SEQ ID NO: 4)
VYCSLVRVSLTCRASQDIGSSLNWLQQKADGTIKRLIYATSSLDSGVPK

RFSGSRSGSDYSLTISSLESEDFVDYYCLQYASSPWTFGGGTKLEIKRA

DAAPHWRSCRSRELWLHHLSSSSRHLMSS

In some embodiments, an antagonist anti-PTP4A1 antibody comprises the amino acid sequence of the heavy chain variable region of monoclonal antibody 223 as follows (SEQ ID NO: 5)
EFMEWSWVILFLLSIIAGVHCQVQLQQSGPELVKPGASVRISCKASGY

TFTSYYIHWVKQRPGQGLEWIGWIYPGNVNTEYNEKFRGKATLTADKS

SSTAYMQLSSLTSEDSAVYFCASEERNYPWFAYWGQGTLVTVSAAKTT

PPPVYPLVPGSLG

In some embodiments, an antagonist anti-PTP4A1 antibody comprises the amino acid sequence of the light chain variable region of monoclonal antibody 223 as follows (SEQ ID NO: 6)
WEFMETDTLLLWVLLLWVPGSTGDIVLTQSPASLAVSLGQRATISCKA

SQSVEDDGENYMNWYQQKPGQSPKLLIYAASNLESGIPARFSGSGSGT

DFTLNIHPVEEEDAATYYCQQSNEDPFTFGSGTKLEIKRADAAPTVSI

FPPSSKLG

Additional non limiting examples of PTP4A1 antagonists/inhibitors include inhibitory nucleic acids (e.g., inhibitory RNA). Thus, in another embodiment, polynucleotides encoding PTP4A1 and subsequences of SEQ ID NO:2 as well as nucleic acid sequences complementary to the sequence or subsequence (e.g., complementary, antisense polynucleotides), are provided.

Inhibitory, antisense, siRNA (small interfering RNA), miRNA (micro RNA), shRNA (small hairpin RNA), RNAi and antisense oligonucleotides can modulate activity, function or expression of PTP4A1 and are therefore useful for modulating PTP4A1. Such inhibitory nucleic acids that interfere with PTP4A1 activity, function or expression can treat a pathology of a fibrotic disease or disorder, thereby reducing, inhibiting or alleviating one or more symptoms of a fibrotic disease or disorder and are therefore useful in the therapeutic and other methods of treatment as described herein.

Inhibitory nucleic acids can be a single-stranded sequence, or form a double- or triple-stranded sequence. In particular aspects, an inhibitory nucleic acid is a micro-RNA (miRNA), siRNA, shRNA, trans-splicing RNA, antisense RNA or triplex forming RNA.

Antisense includes single, double or triple stranded polynucleotides and peptide nucleic acids (PNAs) that bind RNA transcript or DNA (e.g., genomic DNA). Oligonucleotides derived from the transcription initiation site of a target gene, e.g., between positions −10 and +10 from the start site, are another particular example. Triplex forming antisense can bind to double strand DNA thereby inhibiting transcription of the gene. "RNAi" is the use of single or double stranded RNA sequences for inhibiting gene expression (see, e.g., Kennerdell et al., *Cell* 95:1017 (1998); and Fire et al., *Nature,* 391:806 (1998)). Double stranded RNA sequences from a target gene coding region may therefore be used to inhibit or prevent gene expression/transcription in accordance with the methods and uses of the invention. Antisense and RNAi can be produced based upon nucleic acids encoding PTP4A1. For example, a single or double stranded nucleic acid (e.g., RNA) can target PTP4A1 protein encoding gene.

A "siRNA" refers to a therapeutic molecule involved in the RNA interference process for a sequence-specific post-transcriptional gene silencing or gene knockdown. siRNAs have homology with the sequence of the cognate mRNA of the targeted gene. Small interfering RNAs (siRNAs) can be synthesized in vitro or generated by ribonuclease III cleavage from longer dsRNA and are the mediators of sequence-specific mRNA degradation. siRNA or other such nucleic acids of the invention can be chemically synthesized using appropriately protected ribonucleoside phosphoramidites and a conventional DNA/RNA synthesizer. The siRNA can be synthesized as two separate, complementary RNA molecules, or as a single RNA molecule with two complementary regions.

Specific siRNA constructs for inhibiting mRNA of a target gene (e.g., PTP4A1) may be between 15-50 nucleotides in length, and more typically about 20-30 nucleotides in length. Such nucleic acid molecules can be readily incorporated into various vectors for introduction into cells using conventional methods known to one of skill in the art. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Such inhibitory nucleic acids can be further contained within carriers or vectors suitable for passing through a cell membrane for cytoplasmic delivery, and can be modified so as to be nuclease resistant in order to enhance their stability or efficacy in the invention methods and compositions, for example. Such inhibitory nucleic acids can be readily incorporated into viral (e.g., AAV or lentiviral) vectors for introduction into cells using conventional methods known to those skilled in the art.

Additional polynucleotides include fragments of the above-described nucleic acid sequences that are at least 15 bases in length, which is of sufficient length to permit a selective hybridization to and/or amplification of a PTP4A1 nucleic acid. Polynucleotide fragments of at least 15 bases in length can be used to measure PTP4A1 expression, and be useful in accordance with the measurement, detection, diagnostic and prognostic methods. In addition, polynucleotide fragments can be used to screen for PTP4A1 related genes in other organisms, such as mammals, and are referred to herein as "probes."

Invention probes and agents additionally can have a "tag" or "label" or "detectable moiety" linked thereto that provides a means of isolation or identification, or a detection signal (e.g., radionuclides, fluorescent, chemi- or other luminescent moieties). If necessary, additional reagents can be used in combination with the detectable moieties to provide or enhance the detection signal. Such labels and detectable moieties also can be linked to invention PTP4A1 polypeptides, nucleic acids, antibodies, and modified forms disclosed herein.

Thus, in accordance with the invention there are provided isolated polynucleotides that selectively hybridize to the polynucleotides described herein. In one embodiment, an isolated polynucleotide sequence hybridizes under stringent conditions to a polynucleotide encoding full length or a subsequence of PTP4A1, e.g., encoding all or a subsequence of SEQ ID NO:1. In another embodiment, an isolated polynucleotide sequence hybridizes under stringent conditions to a polynucleotide encoding full length or a subsequence of PTP4A1 sequence set forth herein.

Hybridization refers to binding between complementary nucleic acid sequences (e.g., sense/antisense). As used herein, the term "selective hybridization" refers to hybridization under moderately stringent or highly stringent conditions, which can distinguish PTP4A1 related nucleotide sequences from unrelated sequences. Screening procedures which rely on hybridization allow isolation of related nucleic acid sequences, from any organism.

In nucleic acid hybridization reactions, conditions used in order to achieve a particular level of stringency will vary, depending on the nature of the nucleic acids being hybridized. For example, the length, degree of sequence complementarity, sequence composition (e.g., the GC v. AT content), and type (e.g., RNA v. DNA) of the hybridizing regions can be considered in selecting particular hybridization conditions. An additional consideration is whether one of the nucleic acids is immobilized, for example, on a filter. As is understood by those skilled in the art, the Tm (melting temperature) refers to the temperature at which the binding between two sequences is no longer stable. For two sequences to form a stable hybrid, the temperature of the reaction must be less than the Tm for the particular hybridization conditions. In general, the stability of a nucleic acid hybrid decreases as the sodium ion decreases and the temperature of the hybridization reaction increases.

Typically, wash conditions are adjusted so as to attain the desired degree of stringency. Thus, hybridization stringency can be determined, for example, by washing at a particular condition, e.g., at low stringency conditions or high stringency conditions, or by using each of the conditions, e.g., for 10-15 minutes each, in the order listed below, repeating any or all of the steps listed. Optimal conditions for selective hybridization will vary depending on the particular hybridization reaction involved.

A non-limiting example of a moderately stringent hybridization condition is as follows: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash). An example of a moderately-high stringent hybridization condition is as follows: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash); and 0.1×SSC/0.1% SDS at about 52° C. (moderately-high stringency wash). An example of high stringency hybridization conditions is as follows: 2×SSC/0.1% SDS at about room temperature (hybridization conditions); 0.5×SSC/0.1% SDS at about room temperature (low stringency wash); 0.5×SSC/0.1% SDS at about 42° C. (moderate stringency wash); and 0.1×SSC/0.1% SDS at about 65° C. (high stringency wash).

PTP4A1 polynucleotides can include an expression control element distinct from the endogenous PTP4A1 gene (e.g., a non-native element), or exclude a control element from the native PTP4A1 gene to control expression of an operatively linked PTP4A1 nucleic acid. Such polynucleotides containing an expression control element controlling expression of a nucleic acid can be modified or altered as set forth herein, so long as the modified or altered polynucleotide has one or more functions or activities.

For expression in cells, invention polynucleotides, if desired, may be inserted into a vector. Accordingly, compositions and methods further include polynucleotide sequences inserted into a vector.

The term "vector" refers to a plasmid, virus or other vehicle known in the art that can be manipulated by insertion or incorporation of a polynucleotide. Vectors can be used for genetic manipulation (i.e., "cloning vectors") or can be used to transcribe or translate the inserted polynucleotide (i.e., "expression vectors"). A vector generally contains at least an origin of replication for propagation in a cell and a promoter. Additional (heterologous) polynucleotide sequence sequences that can comprise a vector include expression control elements (e.g., a promoter, enhancer), introns, selectable markers (e.g., antibiotic resistance), polyadenylation signal. Control elements, including expression control elements, present within a vector are included to facilitate proper transcription and translation (e.g., splicing signal for introns, maintenance of the correct reading frame of the gene to permit in-frame translation of mRNA and, stop codons etc.).

A viral vector is derived from or based upon one or more nucleic acid elements that comprise a viral genome. Particular viral vectors include retroviral, lentivirus, pseudotyped lentivirus, adenoviral vectors, parvo-virus vectors, and adeno-associated virus (AAV) vectors.

In accordance with the invention, also provided are expression vectors that include inhibitory nucleic acids (e.g., inhibitory RNA) or polynucleotides encoding PTP4A1 and subsequences thereof, as well as nucleic acid sequences complementary to the sequence or subsequence (e.g., complementary, antisense polynucleotides), as set forth herein. In particular embodiments, an expression vector comprises a plasmid, or a viral vector (e.g., a retroviral vector, lentiviral vector, adeno-associated virus (AAV) vector, adenoviral vector, or parvo-virus vector.

A variant sequence (polypeptide or nucleic acid) can have a sequence with 50%, 60%, 70%, 75%, 80%, 85%, 90%, 95%, 96%, 97%, 98%, or more identity to a reference sequence. Variant sequences include naturally occurring alterations of sequence, due to intra-species polymorphisms or different species, as well as artificially produced alterations of sequence. Sequence homology between species is in the range of about 70-80%. An amino acid substitution is one example of a variant.

A "conservative substitution" is the replacement of one amino acid by a biologically, chemically or structurally similar residue. Biologically similar means that the substitution is compatible with an activity or function of the unsubstituted sequence. Structurally similar means that the amino acids have side chains with similar length, such as alanine, glycine and serine, or having similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

As used herein, the term "mimetic" refers to a synthetic chemical compound which has substantially the same structural and/or functional characteristics as the reference molecule. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy activity.

Peptide mimetics can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., a beta turn, gamma turn, beta sheet, alpha helix conformation, and the like. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide and Backbone Modifications," Marcel Decker, NY).

Peptides and peptidomimetics can be produced and isolated using a variety of methods known in the art. Full length peptides and fragments (subsequences) can be synthesized using chemical methods known in the art (see, e.g., Caruthers, Nucleic Acids Res. Symp. Ser. (1980) 215; Horn, Nucleic Acids Res. Symp. Ser. (1980) 225; and Banga, A. K., Therapeutic Peptides and Proteins, Formulation, Processing and Delivery Systems (1995) Technomic Publishing Co., Lancaster, Pa.). Peptide synthesis can be performed using various solid-phase techniques (see, e.g., Roberge, Science (1995) 269:202; Merrifield, Methods Enzymol. (1997) 289:3). Automated synthesis may be achieved, e.g., using a peptide synthesizer.

Individual synthetic residues and polypeptides incorporating mimetics can be synthesized using a variety of procedures and methodologies known in the art (see, e.g., Organic Syntheses Collective Volumes, Gilman, et al. (Eds) John Wiley & Sons, Inc., NY). Peptides and peptide mimetics can also be synthesized using combinatorial methodologies. Techniques for generating peptide and peptidomimetic libraries are known, and include, for example, multipin, tea bag, and split-couple-mix techniques (see, for example, al-Obeidi, Mol. Biotechnol. (1998) 9:205; Hruby, Curr. Opin. Chem. Biol. (1997) 1:114; Ostergaard, Mol. Divers. (1997) 3:17; and Ostresh, Methods Enzymol. (1996) 267: 220). Modified peptides can be further produced by chemical modification methods (see, e.g., Belousov, Nucleic Acids Res. (1997) 25:3440; Frenkel, Free Radic. Biol. Med. (1995) 19:373; and Blommers, Biochemistry (1994) 33:7886).

PTP4A1 antagonists/inhibitors include variants and derivatives that lack PTP4A1 activity or function or those that retain at least a part of an activity of the non-variant or non-derivatized PTP4A1 antagonist/inhibitor. A particular activity (e.g., antagonist or inhibitory activity) of a PTP4A1 inhibitor may be less than or greater than the activity of a corresponding non-variant or non-derivatized PTP4A1 inhibitor.

Non-limiting examples of activities that can be retained, at least in part, include inhibitory or antagonist activity, binding affinity (e.g., $K_d$), avidity and binding selectivity (specificity) or non-selectivity. The variant or derivatized inhibitor can exhibit an activity (e.g., binding affinity) that is greater or less than a corresponding non-variant or non-derivatized inhibitor, e.g., greater or less inhibitory activity, binding affinity (e.g., $K_d$), avidity or binding selectivity (specificity) or non-selectivity. For example, "at least a part" of an activity of an inhibitor can be when the variant or derivatized agent has less of an inhibitory activity, e.g., 10-25%, 25-50%, 50-60%, 60-70%, 70-75%, 75-80%, 80-85%, 85-90%, 90-95%, 95-99%, 100%, or any percent or numerical value or range or value within such ranges. An activity of an inhibitor can be when the variant or derivatized agent has more inhibitory activity, e.g., 110-125%, 125-150%, 150-175%, 175-200%, 200-250%, 250-300%, 300-400%, 400-500%, 500-1000%, 1000-2000%, 2000-5000%, or more, or any percent or numerical value or range or value within such ranges. At least a part of binding affinity of an inhibitor can be when the variant or derivatized inhibitor has less affinity, e.g., 1-3-fold, 1-5-fold, 2-5 fold, 5-10-fold, 5-15-fold, 10-15-fold, 15-20-fold, 20-25-fold, 25-30-fold, 30-50-fold, 50-100 fold, 100-500-fold 500-1000-fold, 1000-5000-fold, or less (e.g., $K_d$). At least a part of binding affinity of an inhibitor can be when the variant or derivatized inhibitor has more affinity, e.g., 1-3-fold, 1-5-fold, 2-5 fold, 5-10-fold, 5-15-fold, 10-15-fold, 15-20-fold, 20-25-fold, 25-30-fold, 30-50-fold, 50-100 fold, 100-500-fold 500-1000-fold, 1000-5000-fold, or more (e.g., $K_d$).

The term "isolated," when used as a modifier of a composition (e.g., polypeptide, nucleic acid, etc.), means that the composition is made by the hand of man or are separated, completely or at least in part, from their naturally occurring in vivo environment. Generally, an isolated composition is substantially free of one or more materials with which they normally associate with in nature, for example, one or more protein, nucleic acid, lipid, carbohydrate, cell membrane. The term "isolated" does not exclude alternative physical forms of the composition, such as multimers/oligomers, variants, modifications or derivatized forms, or forms expressed in host cells produced by the hand of man. Thus, "isolated" does not exclude forms (e.g., pharmaceutical formulations and combination compositions) in which there are combinations therein, any one of which is produced by the hand of man.

An "isolated" composition can also be "purified" when free of most or all of the materials with which it typically associates with in nature. Thus, an isolated polypeptide that also is substantially pure or purified does not include polypeptides or polynucleotides present among millions of other sequences, such as in a polypeptide library or nucleic acids in a genomic or cDNA library, for example. A "purified" composition can be combined with one or more other molecules.

In accordance with the invention, there are provided methods in solution, in solid phase, in vitro, ex vivo or in vivo (i.e., in a subject). In one embodiment, a method includes contacting or administering to a subject, e.g. a subject in need thereof, an amount of a PTP4A1 antagonist/inhibitor to treat the subject. In one particular aspect, a PTP4A1 antagonist/inhibitor is contacted or administered to the subject to reduce, suppress, decrease or inhibit PTP4A1 expression, function or activity. In another particular aspect, an amount of PTP4A1 antagonist/inhibitor is contacted or administered to the subject to treat a fibrotic disease or disorder such as SSc. In a further aspect, an amount of PTP4A1 antagonist/inhibitor is administered to a subject to treat an organ or skin fibrotic disorder. In a still further aspect, an amount of PTP4A1 antagonist/inhibitor is administered to a subject whom has previously experienced organ or skin fibrosis, or is in need of treatment for or has been diagnosed with SSc or another fibrotic disease or disorder, or organ or skin fibrosis.

As used herein, the term "associated with," when used in reference to the relationship between a symptom and a disorder or disease, means that the symptom is caused by the referenced disorder or disease, or is a secondary effect of the referenced disorder or disease. A symptom that is present in a subject may therefore be the direct result of or caused by the referenced disorder or disease, or may be due at least in part to the subject reacting or responding to the referenced disorder or disease, e.g., a secondary effect. For example, symptoms that occur as a result of SSc or another fibrotic disease or disorder, or skin fibrosis, may be due in part to hypersensitivity or an aberrant response of the afflicted subject.

As used herein, the term "subject" includes animals, typically mammalian animals, such as but not limited to humans, non-human primates (apes, gibbons, chimpanzees, orangutans, macaques), domestic animals (dogs and cats), farm animals (horses, cows, goats, sheep, pigs), and experimental animals (mouse, rat, rabbit, guinea pig). Subjects include animal disease models (e.g., fibrotic disease or disorder, such as Systemic sclerosis (SSc)). Subjects include naturally occurring or non-naturally occurring mutated or non-human genetically engineered (e.g., transgenic or knockout) animals. Subjects further include animals having or at risk of having a chronic or acute fibrotic disorder or disease, such as SSc.

In accordance with the invention, there are provided methods of reducing progression, severity, frequency, duration, susceptibility or probability of fibrosis, skin fibrosis or a fibrotic disease or disorder, such as SSc. In one embodiment, a method includes administering to a subject an amount of PTP4A1 antagonist/inhibitor sufficient to reduce or decrease progression, severity, frequency, duration, susceptibility or probability of one or more adverse symptoms associated with fibrosis, skin fibrosis or a skin fibrotic disease or disorder such as SSc.

In another embodiment, a method includes administering to a subject an amount of PTP4A1 antagonist/inhibitor sufficient to reduce or decrease progression, severity, frequency, duration, susceptibility or probability of one or more adverse symptoms caused by or associated with fibrosis, skin fibrosis or a fibrotic disease or disorder, such as SSc. In one aspect, the adverse symptom is selected from skin hardening or tightening; epidermis or dermis thickening; skin tenderness; sensitivity of skin to cold or hot temperatures, cutaneous pruritus, whitening of hands on exposure to cold, pain in affected digits, difficulty in swallowing foods or liquids, nausea, vomiting, weight loss, abdominal cramps, blotting diarrhea, fecal incontinence, shortness of breath on exertion, palpitations without characteristic pain in thoracic cavity, nonproductive cough, atypical chest pain, fatigue, dyspnea, hypertension, joint pain, limitation of movement, joint swelling, muscle pain, inflammatory myopathy or weakness. In another aspect, the subject has been diagnosed as having fibrosis, skin fibrosis or a fibrotic disease or disorder such as SSc.

A "fibrotic disease or disorder" means a disorder or disease related to undesirable or aberrant fibrosis of organ or tissue such as skin or dermal tissue. Fibrosis, and fibrotic diseases and disorders can be acute, chronic, mild, moderate or severe. Examples include, but are not limited to, SSc.

Subjects having or at risk of having fibrotic disease or disorder such as SSc include subjects with an existing condition or a known or a suspected predisposition towards developing a symptom associated with or caused by a fibrotic disease or disorder, such as SSc. Thus, the subject can have active chronic or acute fibrosis, or a fibrotic disease or disorder such as SSc. Accordingly, at risk subjects include those at risk based upon risk factors, such as genetic predisposition, exposure or prior personal or family history, but which the condition or a symptom associated with the condition may not presently manifest itself in the subject.

At risk subjects also appropriate for treatment in accordance with the invention include subjects susceptible to developing fibrosis, or a fibrotic disease or disorder such as SSc. At risk subjects appropriate for treatment in accordance with the invention include subjects having a predisposition towards fibrosis, or a fibrotic disease or disorder such as SSc due to a genetic or environmental risk factor. Methods of the invention include subjects contacted with or administered PTP4A1 antagonist/inhibitor prophylactically, e.g., prior to manifestation of fibrosis, or a fibrotic disease or disorder such as SSc or a symptom thereof.

In another embodiment, there are provided methods of reducing progression, severity, frequency, duration, susceptibility or probability of excessive deposition of extracellular matrix or a disease or disorder related to excessive deposition of extracellular matrix. Such excessive deposition of extracellular matrix can affect cells, tissues and/or organs. Exemplary tissues and/or organs include skin and internal organs such as liver and pulmonary (respiratory) system (e.g., lungs, larynx, trachea, alveoli, bronchi, bronchioles or diaphragm).

In the methods of the invention in which a detectable result or beneficial effect is desired, such as a therapeutic benefit in a subject treated in accordance with the invention, compositions such as PTP4A1 antagonists/inhibitors can be administered in sufficient or effective amounts. An "amount sufficient" or "amount effective" includes an amount that, in a given subject, can have a desired outcome or effect. The "amount sufficient" or "amount effective" can be an amount that provides, in single or multiple doses, alone or in combination with one or more other (second) compounds or agents (e.g., a drug), treatments or therapeutic regimens, a long or short term detectable response, a desired outcome or beneficial effect in a particular given subject of any measurable or detectable degree or duration (e.g., for minutes, hours, days, months, years, or cured).

An amount sufficient or an amount effective can but need not be provided in a single administration and can but need not be administered alone (i.e., a PTP4A1 antagonist/inhibitor with or without a second drug, agent, treatment or therapeutic regimen), or in combination with another compound, agent, treatment or therapeutic regimen. In addition, an amount sufficient or an amount effective need not be sufficient or effective if given in single or multiple doses without a second compound, agent, treatment or therapeutic regimen, since additional doses, amounts or duration above and beyond such doses, or additional drugs, agents, treatment or therapeutic regimens may be included in order to be effective or sufficient in a given subject. Further, an amount sufficient or an amount effective need not be effective in each and every subject, nor a majority of subjects in a given group or population. Thus, as some subjects may not benefit from such treatments an amount sufficient or an amount effective means sufficiency or effectiveness in a particular subject, not a group or the general population. As is typical for such methods, some subjects will exhibit a greater or less response to a method of the invention, including treatment/therapy.

Reducing, inhibiting decreasing, eliminating, delaying, halting or preventing a progression or worsening or an adverse symptom of the disorder or disease is a satisfactory outcome. The dose amount, frequency or duration may be proportionally increased or reduced, as indicated by the status of the disorder or disease being treated, or any adverse side effects of the treatment or therapy.

Dose amounts, frequencies or duration also considered sufficient and effective are those that result in a reduction of the use of another drug, agent, treatment or therapeutic regimen or protocol. For example, a PTP4A1 antagonist/inhibitor is considered as having a beneficial or therapeutic effect if contact, administration or delivery in vivo results in the use of a lesser amount, frequency or duration of another drug, agent, treatment or therapeutic regimen or protocol to treat the disorder or disease, or an adverse symptom thereof.

An "amount sufficient" or "amount effective" includes reducing, preventing, delaying or inhibiting onset, reducing, inhibiting, delaying, preventing or halting the progression or worsening of, reducing, relieving, alleviating the severity, frequency, duration, susceptibility or probability of one or more adverse or undesirable symptoms associated with the disorder or disease of the subject. In addition, hastening a subject's recovery from one or more adverse or undesirable symptoms associated with the disorder or disease is considered to be an amount sufficient or effective. Various beneficial effects and indicia of therapeutic benefit are as set forth herein and are known to the skilled artisan.

An "amount sufficient" or "amount effective," in the appropriate context, can refer to therapeutic or prophylactic amounts. Therapeutically or prophylactically sufficient or effective amounts mean an amount that, in a given subject, detectably improves the disorder or disease, such as fibrotic disorder or disease, as assessed by one or more objective or subjective clinical endpoints appropriate for the disorder or disease.

In accordance with the invention, there are provided methods which provide a beneficial effect, such as a therapeutic benefit, to a subject. In one embodiment, a method includes administering an amount of PTP4A1 antagonist/inhibitor sufficient to provide a therapeutic benefit or beneficial effect to a subject. In one aspect, a method reduces or inhibits probability, susceptibility, severity, frequency, duration or prevents a fibrotic disease or disorder such as SSc (e.g., organ or skin fibrosis) in the subject. In another aspect, a method reduces the probability, susceptibility, severity, frequency, duration or prevents any symptom of a fibrotic disease or disorder such as SSc (e.g., organ or skin fibrosis) in the subject. In an additional aspect, a method reduces or inhibits probability, susceptibility, severity, frequency, duration or prevents skin hardening or tightening; epidermis or dermis thickening; skin tenderness; sensitivity of skin to cold or hot temperatures, cutaneous pruritus, whitening of hands on exposure to cold, pain in affected digits, difficulty in swallowing foods or liquids, nausea, vomiting, weight loss, abdominal cramps, blotting diarrhea, fecal incontinence, shortness of breath on exertion, palpitations without characteristic pain in thoracic cavity, nonproductive cough, atypical chest pain, fatigue, dyspnea, hypertension, joint pain, limitation of movement, joint swelling, muscle pain, inflammatory myopathy or weakness. In a further aspect, a method is sufficient to reduce progression, severity, frequency, duration, susceptibility, probability, halt, eliminate or prevent one or more adverse symptoms associated with a fibrotic disease or disorder such as SSc (e.g., organ or skin fibrosis).

Sufficiency or effectiveness of a particular treatment can be ascertained by various clinical indicia and endpoints. An "amount sufficient" or "amount effective" is therefore an amount that provides an objective or subjective reduction or improvement in progression, severity, frequency, susceptibility or probability of a fibrotic disease or disorder such as SSc (e.g., organ or skin fibrosis), or a symptom thereof. Thus, a reduction, decrease, inhibition, delay, halt, prevention or elimination of one or more adverse symptoms of a fibrotic disease or disorder such as SSc (e.g., organ or skin fibrosis) can be used as a measure of sufficiency or effectiveness.

An "amount sufficient" or "amount effective" also includes an amount that, when used in combination with another, or treatment or therapeutic regimen, reduces the dosage frequency, dosage amount, or an adverse symptom or side effect of the other drug or treatment or therapeutic regimen, or eliminates the need for the other drug or treatment or therapeutic regimen. For example, an "amount sufficient" or "amount effective" of a PTP4A1 antagonist/inhibitor could result in a reduction in the dosage frequency or dosage amount of a steroid, antihistamine, beta adrenergic agonist, anticholinergic, methylxanthine, anti-IgE, anti-leukotriene, anti-beta2 integrin, anti-CCR3 antagonist, or anti-selectin required to achieve the same clinical endpoint.

The terms "treat," "therapy" and grammatical variations thereof when used in reference to a method means the method provides an objective or subjective (perceived) improvement in the disorder or disease, or an adverse symptom associated with the disorder or disease. Non-limiting examples of an improvement can therefore reduce or decrease the probability, susceptibility or likelihood that the subject so treated will manifest one or more symptoms of the disorder or disease. Additional symptoms and physiological or psychological responses caused by or associated with a fibrotic disease or disorder, such as SSc, are set forth herein and known in the art and, therefore, improvements in these and other adverse symptoms are also included in the methods of the invention.

Methods of the invention therefore include providing a detectable or measurable beneficial effect to a subject, or any objective or subjective transient or temporary, or longer-term improvement (e.g., cure) in a fibrotic disease or disorder such as SSc (e.g., organ or skin fibrosis). Thus, a satisfactory clinical endpoint is achieved when there is an incremental improvement in the subject's condition or a partial reduction in the severity, frequency, duration or progression of one or more associated adverse symptoms or inhibition, reduction, elimination, prevention or reversal of one or more of the physiological, biochemical or cellular manifestations or characteristics of the disorder or disease. A therapeutic benefit or improvement ("ameliorate" is used synonymously) therefore need not be complete ablation of any or all adverse symptoms associated with the disorder or disease but is any measurable or detectable objectively or subjectively meaningful improvement in the disorder or disease. For example, inhibiting a worsening or progression of the disorder or disease, or an associated symptom of a fibrotic disease or disorder such as SSc (e.g., slowing or stabilizing organ or skin fibrosis, or one or more symptoms, complications or physiological or psychological effects or responses), even if only for a few days, weeks or months, even if complete ablation of the disorder or disease, or an associated adverse symptom is not achieved is considered to be beneficial effect.

Prophylactic methods are included. "Prophylaxis" and grammatical variations thereof mean a method in accordance with the invention in which contact, administration or in vivo delivery to a subject is prior to manifestation or onset of a disorder or disease (or an associated symptom or physiological or psychological response), such that it can eliminate, prevent, inhibit, decrease or reduce the probability, susceptibility, onset or frequency of having a disorder or disease, or an associated symptom. Target subjects for prophylaxis can be one of increased risk (probability or susceptibility) of contracting the disorder or disease, or an associated symptom, or recurrence of a previously diagnosed disorder or disease, or an associated symptom, as set forth herein.

Any compound or agent (e.g., drug), therapy or treatment having a beneficial, additive, synergistic or complementary activity or effect (beneficial or therapeutic) can be used in combination with a PTP4A1 antagonist/inhibitor in accordance with the invention. A "second compound" or "second agent" refers to any compound or agent (e.g., drug) that is not the first compound or agent of the recited composition, e.g., if a first drug or agent is a particular PTP4A1 antagonist/inhibitor, then a second drug or agent is different from the first PTP4A1 antagonist/inhibitor.

In accordance with the invention there are provided methods in which a second compound or agent (e.g., drug) is administered to the subject. In one embodiment, a second compound or agent (e.g., drug) is administered to the subject prior to, with or following contacting or administering a PTP4A1 antagonist/inhibitor.

Methods of the invention therefore include combination therapies and treatments. Examples of such combination therapies include separate or pooled compounds or PTP4A1 antagonists/inhibitors (e.g., pooled antagonists, compounds or agents). Accordingly, combination compositions, therapies and treatments are provided, as well as methods of using such combinations, therapies and treatments in conjunction with the methods of the invention. Contact, administration or in vivo delivery of a compound or agent, such as a binding agent, or practice of a therapy or treatment, can occur prior to, in conjunction with or following a method or method step of the invention, e.g., prior to, in conjunction or following administering a PTP4A1 antagonist/inhibitor.

Non-limiting examples of functional classes of compounds and agents useful as a second compound or agent (e.g., drug) include anti-inflammatory, and anti-allergy drugs. Additional non-limiting examples of compounds and agents useful for employing in the invention, for example to treat fibrotic disease or disorder, or organ or skin fibrosis, include hormones, such as steroids (e.g., glucocorticoids); antihistamines; beta adrenergic agonists; anticholinergics; methylxanthines; anti-IgE; anti-leukotrienes; anti-beta2 integrins; anti-alpha-4 integrins; H1-receptor antagonists; anti-CCR3 antagonists; and anti-selectins.

Compositions including PTP4A1 antagonists/inhibitors can be included in a pharmaceutically acceptable carrier (excipient, diluent, vehicle or filling agent) for administration to a subject. The terms "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Supplementary active compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include, antibacterial, antiviral, antifungal and anti-parasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanide, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, valacyclovir, ganciclovir, 1,-D-ribofuranosyl-1,2,4-triazole-3 carboxamide, 9→2-hydroxy-ethoxy methylguanine, adamantanamine, 5-iodo-2'-deoxyuridine, trifluorothymidine, interferon and adenine arabinoside.

Exemplary antifungals include agents such as benzoic acid, undecylenicalkanolamide, ciclopiroxolamine, polyenes, imidazoles, allylamine, thiocarbamates, amphotericin B, butylparaben, clindamycin, econazole, amorolfine, butenafine, naftifine, terbinafine, ketoconazole, elubiol, econazole, econazole, itraconazole, isoconazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, fluconazole, flutrimazole, nystatin, pimaricin, amphotericin B, flucytosine, natamycin, tolnaftate, mafenide, dapsone, caspofungin, actofunicone, griseofulvin, potassium iodide, Gentian Violet, ciclopirox, ciclopiroxolamine, haloprogin, ketoconazole, undecylenate, silver sulfadiazine, undecylenic acid, undecylenicalkanolamide and Carbol-Fuchsin.

The pH can be adjusted by use or addition of pharmacologically acceptable acids or bases. Examples of inorganic acids include: hydrochloric acid, hydrobromic acid, nitric acid, sulfuric acid, and/or phosphoric acid. Examples of organic acids are: ascorbic acid, citric acid, malic acid, tartaric acid, maleic acid, succinic acid, fumaric acid, acetic acid, formic acid and/or propionic acid, etc. Acids which form an acid addition salt with the active ingredient may also be used. Examples of bases include alkali metal hydroxides and alkali metal carbonates. If such bases are used, the resulting salts which are contained in the pharmaceutical formulation, are typically compatible with the acid. If desired, mixtures of acids or bases may also be used.

Pharmaceutical compositions can optionally be formulated to be compatible with a particular route of administration. Thus, pharmaceutical compositions include carriers (excipients, diluents, vehicles or filling agents) suitable for administration by various routes and delivery to targets, topically, locally, regionally or systemically.

Exemplary routes of administration for contact or in vivo delivery which a composition can optionally be formulated include skin, dermis or epidermis, oral, buccal, intrapulmonary, inhalation, intrauterine, intradermal, topical, dermal, parenteral, sublingual, subcutaneous, intravascular, intraarterial, intrathecal, intraarticular, intracavity, transdermal, iontophoretic, intraocular, ophthalmic, optical, intravenous, intramuscular, intraglandular, intraorgan, intralymphatic, intra-colon, intraperitoneal.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Pharmaceutical compositions and delivery systems appropriate for compositions and methods of the invention are known to the skilled artisan (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315)

PTP4A1 antagonists/inhibitors and pharmaceutical compositions thereof can be packaged in unit dosage form (capsules, troches, cachets, lozenges, or tablets) for ease of administration and uniformity of dosage. "Unit dosage form" as used herein refers to physically discrete units suited as dosages for treatment or therapy. Each unit contains a predetermined quantity of agent in association with the pharmaceutical carrier (excipient, diluent, vehicle or filling agent) which, when administered in one or more doses, is calculated to produce a desired beneficial effect. Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compositions for transdermal administration, such as "patches" adapted to remain in contact with the epidermis of the intended recipient for an extended or brief period of time. The individual unit dosage forms can be included in multi-dose kits or containers.

Dose amounts, frequency and duration for compounds or agents, including PTP4A1 antagonists/inhibitors, or prodrugs thereof, can be can be empirically determined in appropriate animal models. Dose amounts, frequency and duration can also be determined and optimized in human clinical trials.

The dosage amount can range from about 0.0001 mg/kg of subject body weight/day to about 1,000.0 mg/kg of subject body weight/day. Of course, doses can be more or less, as appropriate, for example, 0.00001 mg/kg of subject body weight to about 10,000.0 mg/kg of subject body weight, about 0.001 mg/kg, to about 1,000 mg/kg, about 0.01 mg/kg, to about 100 mg/kg, or about 0.1 mg/kg, to about 10 mg/kg of subject body weight over a given time period, e.g., 1, 2, 3, 4, 5 or more hours, days, weeks, months, years, in single bolus or in divided/metered doses.

As a non-limiting example, for treatment of a fibrotic disease or disorder, such as SSc, a subject may be administered in single bolus or in divided/metered doses in the range of about 10 to 50,000 micrograms ("mcg")/day, 10 to 20,000 mcg/day, 10 to 10,000 mcg/day, 25-1,000 mcg/day, 25 to 400 mcg/day, 25-200 mcg/day, 25-100 mcg/day or 25-50 mcg/day, which can be adjusted to be greater or less according to the weight of the subject, e.g., per pound, kilogram, etc.

PTP4A1 antagonists/inhibitors, combinations of such antagonists/inhibitors and other actives and pharmaceutical formulations thereof can be administered to a subject at any frequency, as a single bolus or in divided/metered doses, one, two, three, four or more times over a given time period, e.g., per hour, day, week, month or year. Exemplary dosage frequencies for a fibrotic disease or disorder, such as SSc, can vary, but are typically from 1-7 times, 1-5 times, 1-3 times, 2-times or once, daily, weekly or monthly, to reduce, inhibit, decrease, delay, prevent, halt or eliminate progression, severity, frequency, duration, or probability of one or more adverse symptoms of the disorders or diseases, as set forth herein or that would be apparent to one skilled in the art. Timing of contact, administration or in vivo delivery can be dictated by the disorder or disease to be treated. For example, an amount can be administered to the subject substantially contemporaneously with, or within about 1-60 minutes or hours of the onset of a symptom associated with or caused by the fibrotic disease or disorder.

Dosage amount, frequency or duration can be increased, if necessary, or reduced, for example, once control of the disorder or disease is achieved. Other fibrotic disorders or diseases can be similarly treated, dosing amount, frequency or duration reduced, when adequate control of the disorder or disease is achieved.

Of course, the dosage amount, frequency and duration can vary depending upon the judgment of the skilled artisan which will consider various factors such as whether the treatment is prophylactic or therapeutic, the type or severity of the disorder or disease, the associated symptom to be treated, the clinical endpoint(s) desired such as the type and duration of beneficial or therapeutic effect. Additional non-limiting factors to consider in determining appropriate dosage amounts, frequency, and duration include previous or simultaneous treatments, potential adverse systemic, regional or local side effects, the individual subject (e.g., general health, age, gender, race, bioavailability), condition of the subject such as other disorders or diseases present and other treatments or therapies that the subject has or is undergoing (e.g., medical history). The skilled artisan will appreciate the factors that may influence the dosage, frequency and duration required to provide an amount sufficient to provide a subject with a beneficial effect, such as a therapeutic benefit.

The invention provides kits including PTP4A1 antagonists/inhibitors suitable for practicing the methods, treatment protocols or therapeutic regimes herein, and suitable packing material. In one embodiment, a kit includes a PTP4A1 antagonist/inhibitor, and instructions for administering or using the PTP4A1 antagonist/inhibitor. In another embodiment, a kit includes a PTP4A1 antagonist/inhibitor, an article of manufacture for delivery of the antagonist/inhibitor to the target area, organ, tissue or system (e.g., skin) and instructions for administering the PTP4A1 antagonist/inhibitor.

The term "packing material" refers to a physical structure housing a component of the kit. The material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to a ampule, tube or vial containing a kit component. Labels or inserts can additionally include a computer readable medium, such as a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein (e.g., the binding agent or pharmaceutical composition), dose amounts, clinical pharmacology of the active agent(s) including mechanism of action, pharmacokinetics and pharmacodynamics. Labels or inserts can include information identifying manufacturer information, lot numbers, and location and date of manufacture.

Labels or inserts can include information on a disorder or disease for which a kit component may be used. Labels or inserts can include instructions for the clinician or subject for using one or more of the kit components in a method, or treatment protocol or therapeutic regimen. Instructions can include dosage amounts, frequency or duration, and instructions for practicing any of the methods, treatment protocols or therapeutic regimes described herein.

Labels or inserts can include information on any benefit that a component may provide, such as a therapeutic benefit. Labels or inserts can include information on potential adverse side effects, such as warnings to the subject or clinician regarding situations where it would not be appropriate to use a particular composition (e.g., a PTP4A1 antagonist/inhibitor). For example, adverse side effects are generally more likely to occur at higher dose amounts, frequency or duration of the active agent and, therefore, instructions could include recommendations against higher dose amounts, frequency or duration. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Embodiments herein provide cell-free (e.g., in solution, in solid phase) and cell-based (e.g., in vitro or in vivo) methods of measuring expression, function or activity of PTP4A1, as well as methods of detecting and identifying agents that modulate expression, function or activity of PTP4A1. Embodiments herein also provide cell-free (e.g., in solution, in solid phase) and cell-based (e.g., in vitro or in vivo) methods of screening, detecting and identifying agents for treatment of a fibrotic disease or disorder such as SSc (e.g., organ or skin fibrosis).

Such methods can be performed on any subject, such as a mammal (e.g., human, primate). Such subjects can have or be at risk of having a disease or disorder associated with PTP4A1 activity, function, or expression, for example, a fibrotic disease or disorder such as SSc as set forth herein. For example, a subject can have or be at risk of having a food allergy, allergic reaction, hypersensitivity, inflammatory response or inflammation.

The methods can be performed in solution, in solid phase, in silica, in vitro, in a cell, and in vivo. For example, the methods can be performed in solution, in vitro using a biological material or sample, such as a sample or biopsy of cells, tissue or organ, or a fluid or lavage sample from an animal.

In one embodiment, a method for measuring expression or activity of PTP4A1 includes contacting a sample from a subject with a reagent that binds to PTP4A1 nucleic acid or protein, and determining the amount of PTP4A1 nucleic acid or protein in the sample. In another embodiment, a sample from a subject is contacted with a reagent that detects activity or function of PTP4A1 protein, and the amount of PTP4A1 activity or function in the sample determined.

Diagnostic methods are also provided. Such methods include identifying subjects at risk of having or having systemic sclerosis. In one embodiment, expression or activity of PTP4A1 is measured (e.g., from a sample). Elevated PTP4A1 expression or activity compared to a threshold level of PTP4A1 indicative of systemic sclerosis, or control PTP4A1 expression or activity, identifies the subject as having or at risk of having systemic sclerosis. Controls include PTP4A1 expression or activity in age/gender/ethnic matched subjects and the like.

The presence or amount of PTP4A1 expression or activity can also identify a subject appropriate for a PTP4A1 antagonist/inhibitor treatment, as such subjects will have a greater probability of favorably responding to such a treatment. In addition, monitoring expression or activity of PTP4A1 can be used, for example, to ascertain treatment efficacy with a PTP4A1 antagonist/inhibitor.

The invention moreover provides methods of monitoring subjects treated for a fibrotic disease or disorder such as SSc. In one embodiment, expression or activity of PTP4A1 before treatment is measured; expression or activity of PTP4A1 after treatment is measured; and PTP4A1 expression or activity before and after treatment compared. A reduction of expression or activity of PTP4A1 after treatment compared to before treatment indicates improvement of a fibrotic disease or disorder such as SSc, or the same or an increase in PTP4A1 expression or activity after treatment compared to before treatment indicates no improvement or worsening of a fibrotic disease or disorder such as SSc. In a particular, aspect, the treatment monitored is a PTP4A1 antagonist/inhibitor treatment.

Prognostic methods are further provided. In one embodiment, a method of systemic sclerosis prognosis in a subject includes measuring expression or activity of PTP4A1 prior to or after an initial or subsequent systemic sclerosis treatment (e.g., in a sample from a subject); measuring expression or activity of PTP4A1 after an initial or a further systemic sclerosis treatment (e.g., in a sample from the subject); comparing PTP4A1 expression or activity following the initial or the further systemic sclerosis treatment to PTP4A1 expression or activity prior to or after the initial or the subsequent systemic sclerosis treatment. A reduction of expression or activity of PTP4A1 following the initial or the further systemic sclerosis treatment compared to PTP4A1 expression or activity prior to or after the initial or the subsequent systemic sclerosis treatment indicates improved systemic sclerosis prognosis.

In another embodiment, a method of prognosis includes measuring expression or activity of PTP4A1 prior to or after an initial or subsequent treatment of a subject for fibrosis, or a fibrotic disease or disorder (e.g., in a sample from a subject); measuring expression or activity of PTP4A1 after an initial or a further treatment of the subject for fibrosis, or a fibrotic disease or disorder (e.g., in a sample from the subject); comparing PTP4A1 expression or activity following the initial or the further treatment for fibrosis, or a fibrotic disease or disorder to PTP4A1 expression or activity prior to or after the initial or the subsequent treatment for fibrosis, or a fibrotic disease or disorder. A reduction of expression or activity of PTP4A1 following the initial or the further treatment for fibrosis, or a fibrotic disease or disorder compared to PTP4A1 expression or activity prior to or after the initial or the subsequent treatment for fibrosis, or a fibrotic disease or disorder indicates improved fibrosis, or an improved fibrotic disease or disorder prognosis.

Such monitoring, diagnostic and prognostic methods can be performed over a period of time and/or following a number of treatments. Methods can be performed at a regular or irregular intervals, for example, daily, bi-weekly, weekly, bi-monthly, monthly, quarterly, semi- or bi-annually, annually, etc., as appropriate. In particular aspects, a duration of time is from 1-7 days, 7-14 days, 14 days-month or longer, e.g., 1-2, 2-3, 3-4, 4-5, 5-6, 7-8, 8-9, 9-10, 10-11, 11-12 months or longer. In particular aspects, after a first treatment, measurement occurs after subsequent systemic sclerosis treatment, such as a second, third, fourth, fifth, sixth, seventh, eighth, ninth, tenth, eleventh, or further treatment.

Such detection, monitoring, diagnostic, prognostic methods employ detectable reagents for measuring or determining the PTP4A1 protein or nucleic acid encoding PTP4A1 (RNA, cDNA) in the sample. In particular embodiments, a reagent is a detectable nucleic acid that binds to PTP4A1 nucleic acid or detectable protein (e.g., an antibody) that binds to PTP4A1 protein. Accordingly, in various embodiments, PTP4A1 measuring includes contacting the sample with a reagent (e.g., a detectable agent or tag, such as an antibody, protein or nucleic acid that binds to PTP4A1 protein or nucleic acid encoding PTP4A1) that binds to PTP4A1 protein or nucleic acid encoding PTP4A1 and ascertaining the amount of PTP4A1 protein or nucleic acid encoding PTP4A1, or the amount of reagent bound to the PTP4A1 protein or nucleic acid encoding PTP4A1.

The terms "determining," "assaying" and "measuring" and grammatical variations thereof are used interchangeably herein and refer to either qualitative or quantitative determinations, assays, measurements or both qualitative and quantitative determinations. When the terms are used in reference to measurement or detection, any means of assessing the relative amount, including the various methods set forth herein and known in the art. For example, PTP4A1 can be assayed or measured using an antibody, in ELISA assay, Western blot or immunoprecipitation assay. PTP4A1 also can be assayed or measured using a polynucleotide that binds to PTP4A1 nucleic acid.

The term "correlating" and grammatical variations thereof refers to a relationship or link between two or more entities. For example, as disclosed herein PTP4A1 is associated with, among other things, fibrotic diseases and disorders such as SSc. Thus, because of this relationship between PTP4A1 and fibrotic diseases and disorders such as SSc they correlate with each other. Thus, correlating the presence or quantity of PTP4A1 (e.g., above normal) can indicate susceptibility, the presence and/or extent, severity or prognosis of fibrotic diseases and disorders such as SSc in a subject, for example.

Unless otherwise defined, all technical and scientific terms used herein have the same meaning as commonly understood by one of ordinary skill in the art to which this invention relates. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a PTP4A1 antagonist or inhibitor" includes a plurality of PTP4A1 antagonists/inhibitors; and reference to "a symptom" includes a plurality of symptoms (e.g., adverse or undesirable). Of course, this does not preclude limiting certain embodiments of the invention to specific PTP4A1 antagonists/inhibitors, particular symptoms, particular disorders or diseases, particular subjects, etc., using appropriate language.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 0-72 hours (hrs), includes 1, 2, 3, 4, 5, 6, 7 hrs, etc., as well as 1, 2, 3, 4, 5, 6, 7 minutes, etc., and so forth. Reference to a range of doses, such as 0.1-1 ug/kg, 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, includes 0.11-0.9 ug/kg, 2-9 ug/kg, 11.5-24.5 ug/kg, 26-49 ug/kg, 55-90 ug/kg, 125-400 ug/kg, 750-800 ug/kg, 1.1-4.9 mg/kg, 6-9 mg/kg, 11.5-19.5 mg/kg, 21-49 mg/kg, 55-90 mg/kg, 125-200 mg/kg, 275.5-450.1 mg/kg, etc.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis disclosed herein. As an example, the invention includes embodiments in which specific subject matter disclosed herein is excluded from the embodiments. Thus, even though the invention is generally not expressed herein in terms of what the invention does not include, aspects that are not expressly included in the invention are nevertheless expressly or inherently disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

Materials and Methods

NHDF lines from 18-80 years old females were obtained from NDRI. HEK 293T cells were purchased from ATCC.

Cells were cultured in DMEM complete media with 10% FBS.

Cell permeable morpholino oligonucleotides were designed and purchased by Gene Tools.

NGS was performed at the La Jolla Institute Sequencing Core with a Hiseq 2500 from Illumina.

RNA was extracted with QIAGEN micro RNA kit. cDNA was synthetized with Invitrogen Super Script III. qPCR was performed with QIAGEN SYBER Green master mix in a LightCycler480 from Roche. All primers for qPCR were designed by QIAGEN.

RT-PCR was performed with Crimson Taq DNA Polymerase from NEB.

Antibodies for immunoblotting and ChIP were purchased from Cell Signaling. Anti-PRL-1/2 antibody for immunoblotting and immunofluorescence was from Millipore.

ChIP was performed with the ChIP Chromatin Immunoprecipitation kit from Millipore.

Luciferase Assay for SMAD reporter was carried out with the Cignal SMAD Reporter Assay Kit from Millipore. Lipofectamine 3000 from Invitrogen was used for the transfection in HEK 293T cells.

Bleomycin sulfate for in vivo fibrosis model was from Selleckchem.

C57BL/6J female mice for in vivo fibrosis model were obtained from the Jackson laboratory.

PTP4A1 knockout and PTP4A1 knockout/PTP4A2 Het mice were maintained in the laboratory of professor Zhang at the Indiana University.

Collagen assay was performed with the Sircoll assay kit from Biocolors Life Science.

Histology and Trichrome staining were conducted at the La Jolla Institute Histology facility.

Images for dermal thickness measurements were obtained with an AxioScan Z1 slide scanner from Zeiss and analyzed with ImageJ software.

Statistical analysis was performed using GraphPad Prism software. A nonparametric t test or Mann-Whitney test was used where indicated. A P value <0.05 was considered statistically significant.

Example 2 mRNA Expression Profile of all the PTPs (109 Genes) in Primary Dermal Fibroblasts with Diffuse SSc Compared to Healthy Subjects.

Figure 1:
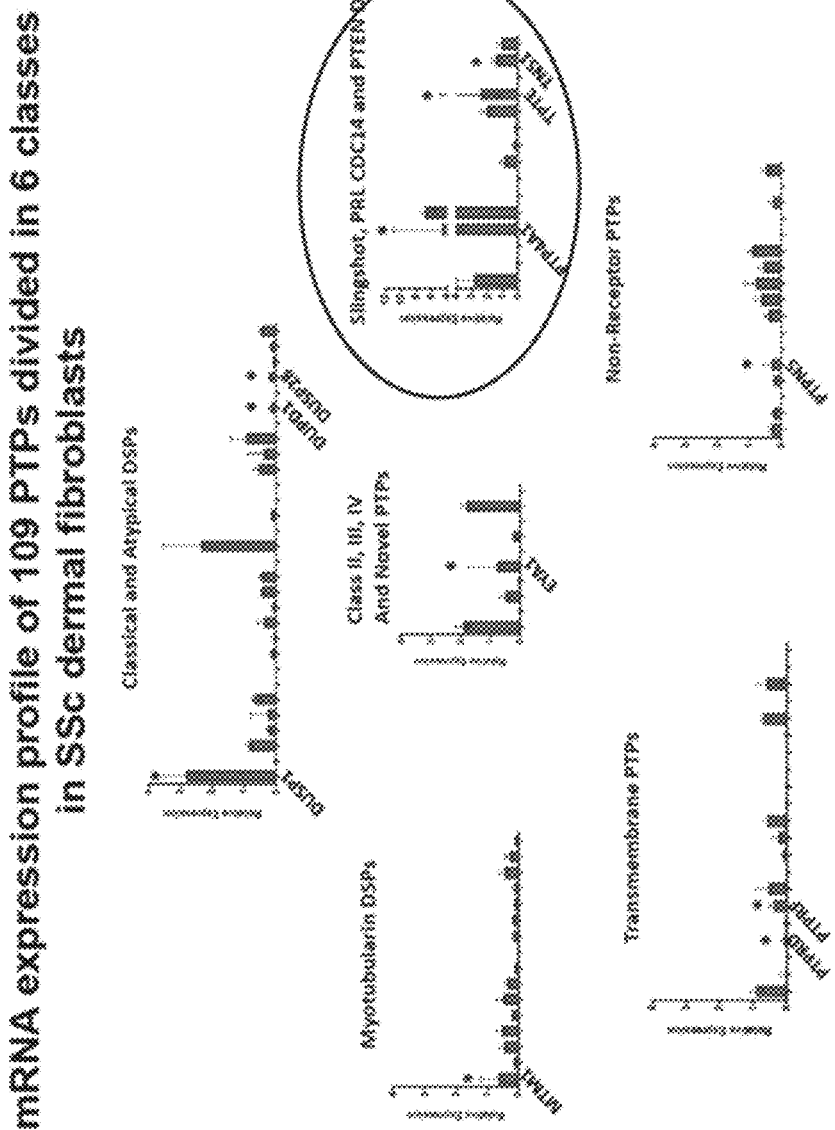
Figure 3:
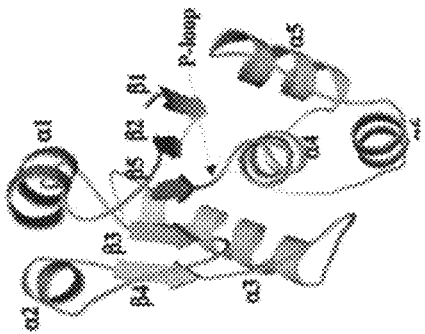
FIG. 3 shows that PTP4A1 belongs to the PRL (phosphatase of regenerating liver) family.
Figure 4:
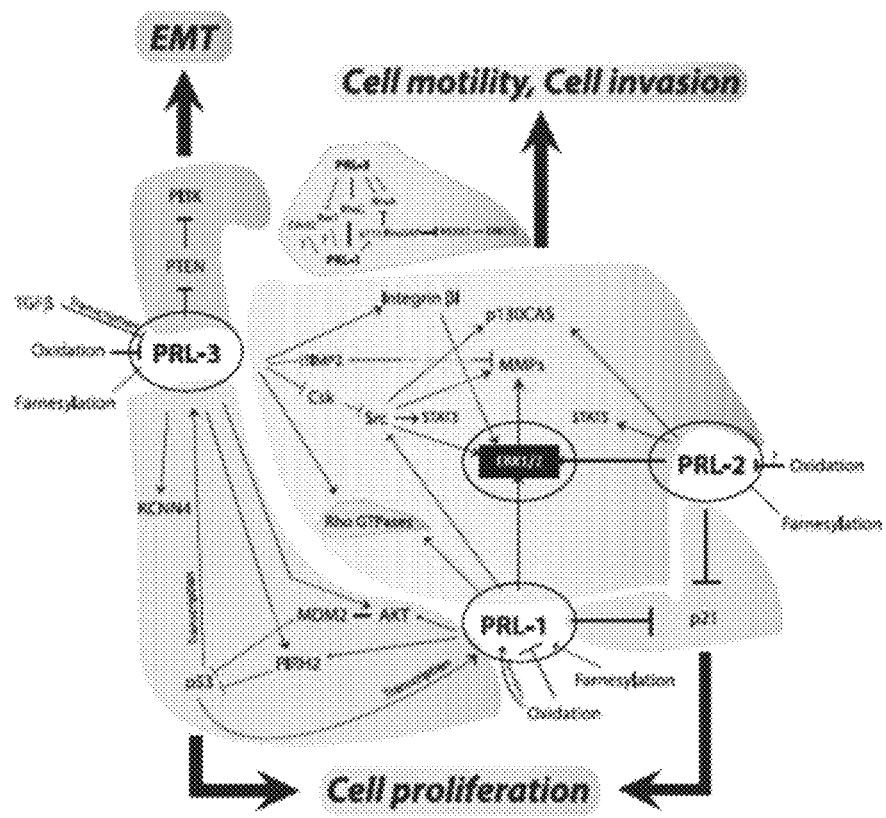
FIG. 4 depicts an overview of current knowledge of the signaling pathways affected by PRL phosphatases and the outcome in cell migration and proliferation. Arrows indicate positive regulation, crossed lines indicate negative regulation and question marks indicate either not studied or not understood.

To identify genes involved in SSc, mRNA was extracted from primary dermal fibroblast cells, converted in cDNA and the 109 PTPs gene expression levels were analyzed by qPCR with the SYBER Green system. A first analysis (FIG. 1) on 5 SSc patients and 5 healthy donors and genes marked with a * showed a significance different expression level from SSc and healthy patients with Mann Whitney test. After analysis of a second cohort of samples (FIG. 2A), only PTP4A1 showed a significance different expression level from SSc and healthy patients with Mann Whitney test. This result was confirmed with a third cohort of patients (FIG. 2B). Immunoblotting with an antibody anti-PTP4A1 was used to detect the protein level in dermal fibroblast protein lysates from 5 SSc patient and 5 healthy donor. As control an antibody anti-Tubulin to calculate the relative protein expression. PTP4A1 showed a significantly increased protein level in SSc fibroblasts compared with healthy patients using Mann Whitney test (C). POLR2A gene expression was used to calculate the relative expression of the PTP genes

Example 3

Gene Expression Knockdown Strategy and Transcriptome Analysis by Next Generation Sequencing.

Figure 5:
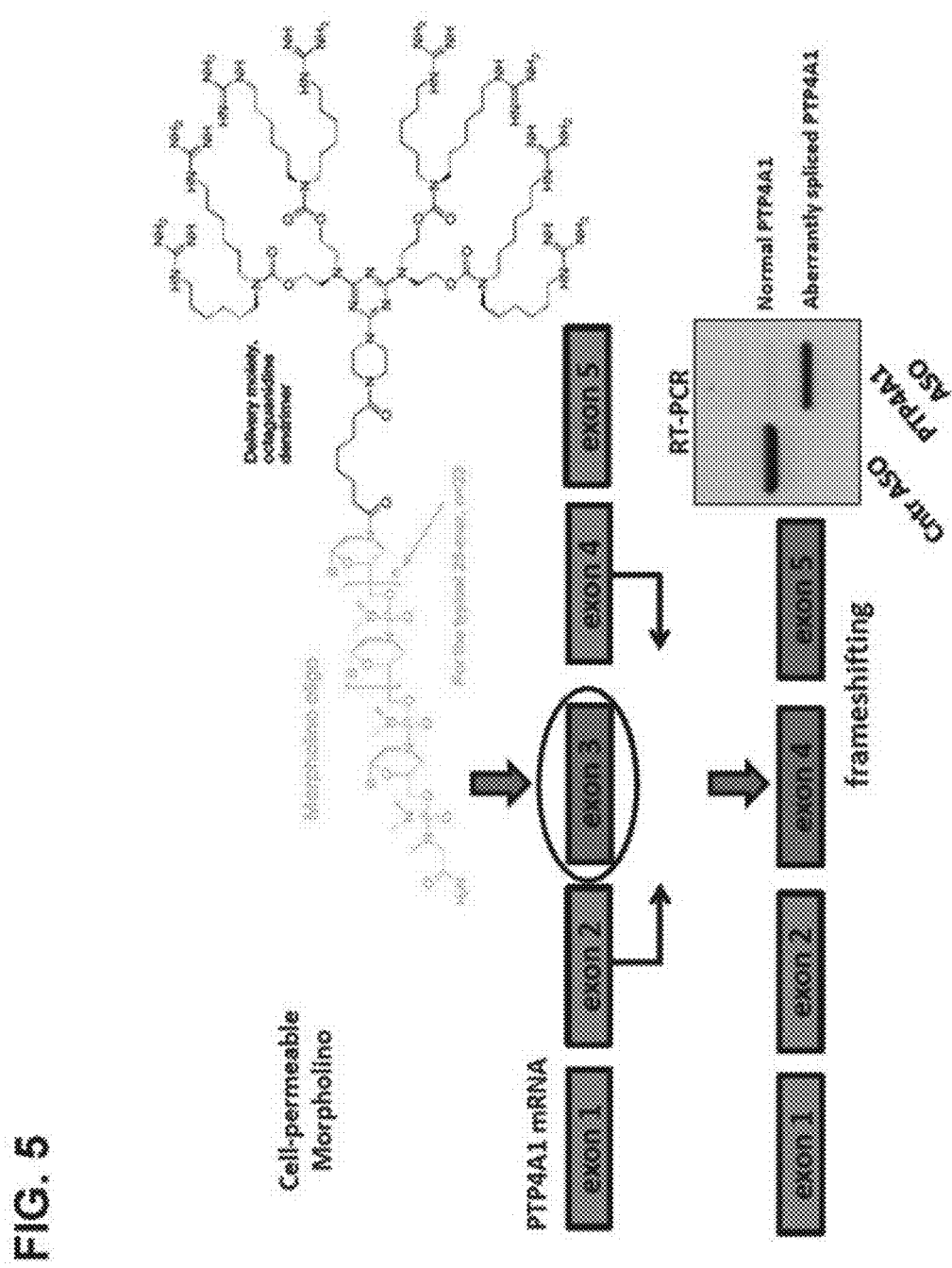
FIG. 5 shows gene expression knockdown in primary fibroblasts with cell permeable morpholino oligonucleotides designed against mRNA splice junctions.

To determine the effect of PTP4A1 gene expression, mRNA knockdown in primary fibroblasts with cell permeable morpholino oligonucleotides were designed against mRNA splice junctions, and carry minimal risk of off-target effects (FIG. 5). The morpholino causes the excision of exon 4 of PTP4A1 mRNA. The efficiency of knockdown was assessed with a RT-PCR with two oligos placed on exon 3 and exon 5. A week incubation with 2.5 microM morpholino routinely enables >90% PTP4A1 gene knockdown.

Whole transcriptome analysis by Next Generation Sequencing was performed on 3 lines of normal human dermal fibroblasts subjected to knockdown of the PTP4A1 gene with cell permeable morpholino oligonucleotides. FIG. 6A shows the differential expression of all genes in cells treated with anti PTP4A1 morpholino vs control morpholino. In red are highlighted the gene with a statistical increased (upper part of the figure) or decreased (lower part of the figure) expression. FIG. 6B shows the gene upregulation (in red) and downregulation (in green) in a more comprehensive way. Knockdown of PTP4A1 gene induced a dramatic inhibition of the expression of numerous genes that are implicated in fibrosis, including collagens (COL1A2, COL3A1) and ACTA2. The genes notably included SMAD3, an important mediator of TGFbeta signaling (FIG. 6C).

Example 4

Attenuation of Pro-Fibrotic TGF-Beta in Human Dermal Fibroblasts Subject to Knock-Down of PTP4A1.

PTP4A1 interrupts the canonical SMAD3-dependent TGFbeta pathway. In a normal situation SMAD3 is phosphorylated under TGFbeta stimulation and is recruited by SMAD4 to translocate to the nucleus to activate the transcription of different genes, like COL1A2. With downregulation of SMAD3, the pathway became less active (FIG. 7A).

Six different lines of normal human dermal fibroblast were treated for 7 days with 2.5 microM control morpholino or anti-PTP4A1 morpholino and then stimulated for 24 h with 20 ng/ml TGFbeta1. The SMAD3 gene was downregulated with PTP4A1 knockdown in TGFbeta1-untreated cells (FIG. 7B). Mean±SEM of densitometric scan shows relative expression plus representative immunoblots of SMAD3 protein (upper bands) and GAPDH protein (lower bands) used as control in TGFbeta1-untreated cells FIG. 7C). Reduced COL1A2 gene expression in presence of anti-PTP4A1 morpholino in TGFbeta1-treated or untreated cells (FIG. 7D)

Example 5

Chromatin Immunoprecipitation (ChIP) to Investigate the Interaction Between Proteins and DNA in the Cell.

Six different lines of normal human dermal fibroblast were treated for 7 days with 2.5 microM control morpholino or anti-PTP4A1 morpholino and then stimulated for 24 h with 20 ng/ml TGFbeta1. DNA and associated proteins on chromatin were crosslinked. The DNA-protein complexes (chromatin-protein) are then sheared into ~500 base pair (bp) DNA fragments by sonication. Cross-linked DNA fragments associated with SMAD3 are selectively immuno-precipitated from the cell debris using an anti-phosphoS-MAD3 antibody. The associated DNA fragments are purified and the amount of COL1A2 promoter is obtained with a qPCR. These results show that PTP4A1 knockdown reduces the amount of SMAD3 that binds the promoter of COL1A2 gene (FIG. 8).

Example 6

Attenuation of α-SMA Pro-Fibrotic Pathway in Human Dermal Fibroblasts Subject to Knock-Down of PTP4A1.

PTP4A1 interrupts the transformation of fibroblasts in myofibroblasts, which are cells involved in the inflammatory response to injury. In a normal situation SMAD3 is phosphorylated under TGFbeta stimulation and is recruited by SMAD4 to translocate in to the nucleus to activate the transcription of different genes, like alphaSMA, the gene that regulates the transition from fibroblast into myofibroblast. With the knockdown of PTP4A1 the myofibroblast pathway became less active (FIG. 9A).

Six different lines of normal human dermal fibroblast were treated for 7 days with 2.5 microM control morpholino or anti-PTP4A1 morpholino and then stimulated for 24 h with 20 ng/ml TGFbeta1. Mean±SEM of densitometric scan relative expression plus representative immunoblots of alphaSMA protein (upper bands) and GAPDH protein (lower bands) used as control in TGFbeta1-untreated cells (FIG. 9B). Reduced alphaSMA gene expression in the presence of anti-PTP4A1 morpholino in TGFbeta1-treated or untreated cells (FIG. 9C).

Example 7

PTP4A1 Over-Expression Enhances Activation of SMAD Reporter after TGFbeta Stimulation.

The SMAD reporter assay is designed to monitor the activity of TGFβ-induced signal transduction pathways in cultured cells. HEK 293T cells were co-transfected with human PTP4A1 or PTPN22-encoding vectors together with a firefly luciferase SMAD reporter and a control luciferase Renilla vector. Cells were stimulated with 20 ng/ml TGF-beta1 for 24 h. Graph shows mean±SEM of relative ratio of Firefly/Renilla luciferase signal of cells transfected with empty, PTP4A1 WT and a PTPN22 vectors in 3 independent experiments. The result shows that the overexpression of PTP4A1 in HEK 293T cells led to enhancement of TGFbeta-induced activation of a SMAD-sensitive reporter (FIG. 10). The empty vector and PTPN22 overexpression didn't induce the reporter activation.

Example 8

Studies with a Mouse Dermal Sclerosis Model.

Dermal sclerosis induced by Bleomycin closely resembles systemic sclerosis both histologically and biochemically (FIG. 11). Skin fibrosis was induced in WT B6 mice by subcutaneous injections of 100 micrograms bleomycin every other day, for 2 weeks. PTP4A1/2 immunofluorescence (red signal) in skin sections of mice treated with PBS or bleomycin. Hoechst nuclear staining (blue signal). Images show the overexpression of PTP4A1 and PTP4A2 (the Ab used is cross-reactive) in the Bleomycin model (FIG. 12A). Masson's trichrome staining of skin slides of bleomycin-treated WT, PTP4A1 KO or PTP4A1 KO/PTP4A2 mice. The blue layer is the dermal collagen, increased in the bleomycin model (FIG. 12B).

Studies with a Dermal sclerosis model in PTP4A1 knockout and PTP4A1 Knockout/Het mice were then undertaken (FIG. 13). Skin fibrosis was induced in WT, PTP4A1 KO and PTP4A1 KO/PTP4A2 Het B6 mice by subcutaneous injections of 100 micrograms bleomycin every other day, for 2 weeks. Dermal thickness, skin collagen concentration and alphaSMA expression of skin samples from 11 WT, 10 PTP4A1 KO and 2 PTP4A1 KO/PTP4A2 Het mice treated with bleomycin were analyzed. The results show that global KO of PTP4A1 led to a mild but significant protection from experimental skin fibrosis induced by injections of bleomycin. Due to high level of identity (86%) between PTP4A1 and PTP4A2, compensation by PTP4A2 might reduce the extent of the phenotype caused by PTP4A1 KO (expression of PTP4A3 in NDHF was not detected). Mean±SEM is shown.

Example 9

Data Implications.

In summary, the data disclosed herein indicate that PTP4A1 inactivation provides significant protection from experimental skin fibrosis. The data herein therefore shows that PTP4A1 is an attractive target for therapy of pathologies characterized by fibrosis of the skin and internal organs, such as Systemic sclerosis (SSc).

REFERENCES

1. Denton, C. P. & Ong, V. H. Targeted therapies for systemic sclerosis. Nat Rev Rheumatol (2013).
2. Bhattacharyya, S., Wei, J. & Varga, J. Understanding fibrosis in systemic sclerosis: shifting paradigms, emerging opportunities. Nat Rev Rheumatol 8, 42-54 (2012).
3. Tashkin, D. P. et al. Effects of 1-year treatment with cyclophosphamide on outcomes at 2 years in scleroderma lung disease. Am J Respir Crit Care Med 176, 1026-34 (2007).
4. Burt, R. K. & Milanetti, F. Hematopoietic stem cell transplantation for systemic sclerosis: history and current status. Curr Opin Rheumatol 23, 519-29 (2011).
5. Beyer, C., Distler, O. & Distler, J. H. Innovative antifibrotic therapies in systemic sclerosis. Curr Opin Rheumatol 24, 274-80 (2012).
6. Pope, J. et al. Imatinib in active diffuse cutaneous systemic sclerosis: Results of a six-month, randomized, double-blind, placebo-controlled, proof-of-concept pilot study at a single center. Arthritis Rheum 63, 3547-51 (2011).
7. Prey, S. et al. Imatinib mesylate in scleroderma-associated diffuse skin fibrosis: a phase II multicentre randomized double-blinded controlled trial. Br J Dermatol 167, 1138-44 (2012).
8. Varga, J. & Pasche, B. Transforming growth factor beta as a therapeutic target in systemic sclerosis. Nat Rev Rheumatol 5, 200-6 (2009).
9. Wei, J. et al. Wnt/beta-catenin signaling is hyperactivated in systemic sclerosis and induces Smad-dependent fibrotic responses in mesenchymal cells. Arthritis Rheum 64, 2734-45 (2012).
10. Beyer, C. et al. Blockade of canonical Wnt signalling ameliorates experimental dermal fibrosis. Ann Rheum Dis (2013).
11. Usategui, A., del Rey, M. J. & Pablos, J. L. Fibroblast abnormalities in the pathogenesis of systemic sclerosis. Expert Rev Clin Immunol 7, 491-8 (2011).

Example 10

Methods of Treatment.

A human subject is diagnosed with systemic sclerosis by a medical care giver and the subject is determined to display symptoms of systemic sclerosis which include fatigue, joint pain, joint swelling, skin thickening, cutaneous pruritus, difficulty swallowing and abdominal cramps. The subject is administered a humanized monoclonal anti-PTP4A1 antibody comprising the heavy chain variable region and light chain variable region of monoclonal antibody 269. The antibody is administered intravenously (i.v.), once every two days at a dose of 10 mg/kg of the subject's body weight. After six weeks the subject's symptoms are reassessed. The subject is determined to have significantly less join pain, less joint swelling, less pruritus, no difficulty swallowing and significantly less abdominal cramping.

The anti-PTP4A1 antibody is then administered i.v. once a week at a dose of 10 mg/kg for a period of six months in conjunction with prednisone, which is administered at 2 mg/kg/day in divided doses, 3 to 4 times/day for 14 consecutive days, at which time the dose of prednisone is reduced to 1 mg/kg/dose given every other day for 4 weeks. Six months later the subject is determined to display a significant improvement in health with minor or no presentation of adverse symptoms of systemic sclerosis.

Example 11

Certain Embodiments.

A1. A method of modulating protein tyrosine phosphatase 4A1 (PTP4A1) expression or activity, comprising administration of an agent which modulates expression or activity of protein tyrosine phosphatase 4A1 (PTP4A1).

A2. A method of modulating a pathology of systemic sclerosis, comprising administration of an effective amount of an antagonist of protein tyrosine phosphatase 4A1 (PTP4A1) sufficient to modulate the pathology of fibrosis or systemic sclerosis.

A3. A method of treating a fibrotic disease or disorder in a subject, comprising administering an effective amount of an antagonist of protein tyrosine phosphatase 4A1 (PTP4A1) to a subject sufficient to treat the fibrotic disease or disorder.

A4. The method of embodiments A3, wherein the fibrotic disease comprises systemic sclerosis.

A5. The method of embodiments A3 or A4, wherein the subject is at risk of or has systemic sclerosis.

A6. The method of any one of embodiments A1 to A5, wherein the antagonist or agent decreases expression or activity of PTP4A1 nucleic acid or PTP4A1 protein.

A7. The method of any one of embodiments A1 to A6, wherein the agent or antagonist comprises an antibody or antibody fragment thereof that binds to the PTP4A1 protein.

A8. The method of any one of embodiments A1 to A6, wherein the agent or antagonist comprises a small molecule that binds to the PTP4A1 protein.

A9. The method of any one of embodiments A1 to A6, wherein the agent or antagonist comprises a dominant negative protein that binds to the PTP4A1 protein.

A10. The method of embodiment A9, wherein the dominant negative protein comprises a PTP4A1 polypeptide, or a fragment of a PTP4A1 polypeptide that binds to PTP4A1 or that binds to a target of PTP4A1.

A11. The method of any one of embodiments A1 to A6, wherein the agent or antagonist comprises an inhibitory nucleic acid that decreases, reduces, suppresses, inhibits, limits or controls expression or activity of PTP4A1.

A12. The method of any one of embodiments A1 to A11, wherein PTP4A1 or the PTP4A1 protein comprises the amino acid sequence set forth as (SEQ ID NO: 1)
MARMNRPAPVEVTYKNMRFLITHNPTNATLNKFIEELKKYGVTTVRVCE

ATYDTKFTWVTDWPFDDGAPPSNQIVDDWLSLVKIKFREEPGCCIAVHC

VAGLGRAPVLVALALIEGGMKYKDAVQFIPQKRRGAENSKQLLYLEKYR

PKMRLRFKDSNGHRNNCCIQ.

A13. The method of embodiment A11, wherein the inhibitory nucleic acid comprises a RNAi, micro-RNA (miRNA), siRNA, shRNA, trans-splicing RNA, anti-sense RNA or triplex forming RNA that binds to PTP4A1 nucleic acid.

A14. The method of any one of embodiments A1 to A11, wherein the PTP4A1 nucleic acid is a cDNA set forth as:

(SEQ ID NO: 2)
ATGGCTCGAATGAACCGCCCAGCTCCTGTGGAAGTCACATACAAGAACA

TGAGATTTCTTATTACACACAATCCAACCAATGCGACCTTAAACAAATT

TATAGAGGAACTTAAGAAGTATGGAGTTACCACAATAGTAAGAGTATGT

GAAGCAACTTATGACACTACTCTTGTGGAGAAAGAAGGTATCCATGTTC

TTGATTGGCCTTTTGATGATGGTGCACCACCATCCAACCAGATTGTTGA

TGACTGGTTAAGTCTTGTGAAAATTAAGTTTCGTGAAGAACCTGGTTGT

TGTATTGCTGTTCATTGCGTTGCAGGCCTTGGGAGAGCTCCAGTACTTG

TTGCCCTAGCATTAATTGAAGGTGGAATGAAATACGAAGATGCAGTACA

ATTCATAAGACAAAAGCGGCGTGGAGCTTTTAACAGCAAGCAACTTCTG

TATTTGGAGAAGTATCGTCCTAAAATGCGGCTGCGTTTCAAAGATTCCA

ACGGTCATAGAAACAACTGTTGCATTCAATAA, or an mRNA corresponding thereto.

A15. The method of embodiment A11, wherein the inhibitory nucleic acid comprises a RNAi, micro-RNA (miRNA), siRNA, shRNA, trans-splicing RNA, anti-sense RNA or triplex forming RNA that binds to PTP4A1 nucleic acid in an expression cassette or vector.

A16. The method of embodiment A15, wherein the vector comprises a viral vector.

A17. The method of embodiment A15, wherein the vector comprises a lentiviral or adeno-associated viral (AAV) vector.

A18. The method of any one of embodiments A15 to A17, wherein the vector comprises a viral vector that infects a cell.

A19. The method of any one of embodiments A15 to A17, wherein the vector comprises a viral vector that infects a fibroblast or dermal cell.

A20. The method of any one of embodiments A15 to A17, wherein the vector comprises a viral vector that infects a dermal fibroblast cell.

A21. The method of any one of embodiments A15 to A17, wherein the vector comprises a viral vector that infects a human cell.

A22. The method of any of embodiments A18 to A20, wherein the cell is a human cell.

A23. The method of any of embodiments A1 to A22, wherein the agent or antagonist comprises a pharmaceutical composition.

A24. The method of any one of embodiments A2 to A23, wherein the method modulates expression or activity of PTP4A1.

A25. The method of any one of embodiments A1 to A24, wherein the method comprises decreasing, reducing, suppressing, inhibiting, limiting or controlling expression or activity of PTP4A1.

A26. The method of any one of embodiments A1 to A25, wherein the method comprises decreasing, reducing, suppressing, inhibiting, limiting or controlling pathology of systemic sclerosis or the fibrotic disease or disorder.

A27. The method of any of embodiments A1 to A26, wherein the method comprises decreasing, reducing, inhibiting, suppressing, limiting or controlling in a subject an undesirable or adverse symptom of systemic sclerosis or the fibrotic disease or disorder.

A28. The method of embodiment A26 or A27, wherein the pathology or symptom of systemic sclerosis or the fibrotic disease or disorder comprises fibrosis, skin thickening, cutaneous pruritus, whitening of hands on exposure to cold, pain in affected digits, difficulty in swallowing foods or liquids, nausea, vomiting, weight loss, abdominal cramps, blotting diarrhea, fecal incontinence, shortness of breath on exertion, palpitations without characteristic pain in thoracic cavity, nonproductive cough, atypical chest pain, fatigue, dyspnea, hypertension, joint pain, limitation of movement, joint swelling, muscle pain, inflammatory myopathy or weakness.

A29. The method of embodiments A3 to A28, wherein the fibrotic disease or disorder affects or is present in liver or pulmonary (respiratory) system.

A30. The method of any of embodiments A1 to A29, further comprising administering a drug, wherein the drug is administered before, after or concurrently with the agent or antagonist, or wherein the drug is administered in combination with the agent or antagonist.

A31. The method of any of embodiments A1 to A30, wherein the agent or antagonist is administered subcutaneously, intravenously, intra-peritoneally, intra-muscularly, intra-arterially, intra-colon, or via ingestion, inhalation, orally, or topically.

A32. The method of any of embodiments A1 to A31, wherein the agent or antagonist is delivered to the surface of the skin.

A33. The method of any of embodiments A1 to A32, wherein the agent or antagonist is delivered to the arms, legs, torso, back, hands, feet, neck, face or head of the subject.

A34. The method of any of embodiments A1 to A33, wherein the agent or antagonist is administered one, two, three, four or more times daily, weekly, monthly, bi-monthly, or annually.

A35. The method of any of embodiments A1 to A34, wherein the amount of the agent or antagonist administered is from about 0.00001 mg/kg to about 10,000 mg/kg, from about 0.0001 mg/kg to about 1000 mg/kg, from about 0.001 mg/kg to about 100 mg/kg, from about 0.01 mg/kg to about 10 mg/kg, or from about 0.1 mg/kg, about 1 mg/kg body weight.

A36. The method of any of embodiments A1 to A35, wherein the agent or antagonist is administered to the subject substantially contemporaneously with, or within about 1-60 minutes, hours, or days of the onset of an undesirable or adverse symptom associated with systemic sclerosis.

A37. The method of any of embodiments A1 to A36, wherein the subject is a mammal.

A38. The method of any of embodiments A1 to A36, wherein the subject is a human. An animal model of human systemic sclerosis, wherein the model has reduced or inactive expression of endogenous gene encoding protein tyrosine phosphatase 4A1, or has a disrupted or knocked-out endogenous gene encoding protein tyrosine phosphatase 4A1.

A39. The animal model of embodiment A39, generated by genetic modification of stem cells.

A40. The animal model of embodiment A39, generated through cross-breeding.

A41. The animal model of embodiment A39, comprising a rodent.

A42. The animal model of embodiment A39, comprising a mouse or rat.

B1. A method of measuring expression or activity of PTP4A1, comprising contacting a sample from a subject with a reagent that binds to PTP4A1 nucleic acid or protein and determining the amount of PTP4A1 nucleic acid or protein in the sample.

C1. A method of identifying a subject at risk of having or having systemic sclerosis, comprising measuring expression or activity of PTP4A1, wherein elevated PTP4A1 expression or activity compared to control PTP4A1 expression or activity identifies the subject as at risk of having or having systemic sclerosis.

D1. A method of monitoring a subject treated for systemic sclerosis, comprising:
  (a) measuring expression or activity of PTP4A1 before treatment;
  (b) measuring expression or activity of PTP4A1 after treatment; and
  (c) comparing PTP4A1 expression or activity before and after treatment,
  wherein reduction of expression or activity of PTP4A1 after treatment compared to before treatment indicates improvement of systemic sclerosis; or
  wherein the same or an increase in PTP4A1 expression or activity after treatment compared to before treatment indicates no improvement or worsening of systemic sclerosis.

E1. A method of systemic sclerosis prognosis in a subject, comprising:
  (a) measuring expression or activity of PTP4A1 prior to or after an initial or subsequent systemic sclerosis treatment;
  (b) measuring expression or activity of PTP4A1 after an initial or a further systemic sclerosis treatment; and
  (c) comparing PTP4A1 expression or activity following the initial or the further systemic sclerosis treatment to PTP4A1 expression or activity prior to or after the initial or the subsequent systemic sclerosis treatment, wherein reduction of expression or activity of PTP4A1 following the initial or the further systemic sclerosis treatment compared to PTP4A1 expression or activity prior to or after the initial or the subsequent systemic sclerosis treatment indicates improved systemic sclerosis prognosis.

E2. The method of embodiment E1, wherein the initial systemic sclerosis treatment is a first treatment, and the subsequent systemic sclerosis treatment is a second, third, fourth, fifth, sixth, seventh, eighth, ninth, tenth or further treatment.

E3. The method of embodiment E1, wherein the further systemic sclerosis treatment follows the subsequent systemic sclerosis treatment.

E4. The method of any one of embodiments B1, C1, D1 and E1 to E3, comprising measuring expression or activity of PTP4A1 in a sample from a subject.

E5. The method of embodiment E4, wherein the sample is contacted with a detectable reagent.

E6. The method of embodiment E5, wherein the reagent comprises a detectable nucleic acid that binds to PTP4A1 nucleic acid or detectable protein that binds to PTP4A1 protein.

E7. The method of embodiment E6, wherein the detectable protein that binds to PTP4A1 protein comprises an antibody.

What is claimed is:

1. A method of decreasing expression, function, or activity of a protein tyrosine phosphatase 4A1 (PTP4A1) protein, comprising administering to a subject having fibrosis or systemic sclerosis a therapeutically effective amount of an agent which decreases expression, function or activity of the PTP4A1 protein, wherein the agent comprises an antisense oligonucleotide (ASO) that specifically binds to a PTP4A1 nucleic acid and inhibits the expression, function or activity of the PTP4A1 protein.

2. The method of claim 1, wherein the therapeutically effective amount of the agent administered to the subject is sufficient to reduce a pathology of fibrosis or systemic sclerosis.

3. The method of claim 2, wherein the method comprises treating the fibrosis or the systemic sclerosis.

4. The method of claim 2, wherein the subject is a human.

5. The method of claim 2, wherein the agent decreases expression of the PTP4A1 nucleic acid or the PTP4A1 protein.

6. The method of claim 2, wherein the agent comprises an ASO that decreases, reduces, suppresses, inhibits, limits or controls expression or activity of the PTP4A1 protein, wherein the acid ASO comprises, micro-RNA (miRNA), trans-splicing RNA, aptamers or triplex forming RNA that binds to the PTP4A1 nucleic acid or protein.

7. The method of claim 5, wherein the PTP4A1 nucleic acid comprises a cDNA set forth as SEQ ID NO:2, or an mRNA corresponding thereto.

8. The method of claim 1, wherein an expression cassette or vector comprises the ASO, and the vector is selected from a viral vector, a lentiviral vector, and an adeno-associated viral (AAV) vector.

9. The method of claim 8, wherein the vector can infect a human fibroblast cell or a human dermal cell.

10. The method of claim 1, wherein a pharmaceutical composition comprises the agent.

11. The method of claim 2, wherein the method comprises: (a) decreasing, reducing, suppressing, inhibiting, limiting or controlling expression or activity of the PTP4A1 protein, (b) decreasing, reducing, suppressing, inhibiting, limiting or controlling the pathology of the fibrosis or systemic sclerosis, or (c) decreasing, reducing, inhibiting, suppressing, limiting or controlling an undesirable or adverse symptom of the fibrosis or systemic sclerosis in the subject.

12. The method of claim 11, wherein the pathology or the symptom of the systemic sclerosis comprises fibrosis, skin thickening, cutaneous pruritus, whitening of hands on exposure to cold, pain in affected digits, difficulty in swallowing foods or liquids, nausea, vomiting, weight loss, abdominal cramps, blotting diarrhea, fecal incontinence, shortness of breath on exertion, palpitations without characteristic pain in thoracic cavity, nonproductive cough, atypical chest pain, fatigue, dyspnea, hypertension, joint pain, limitation of movement, joint swelling, muscle pain, inflammatory myopathy or weakness.

13. The method of claim 3, further comprising administering a drug to the subject, before, after, concurrently or in combination with the administering of the agent or antagonist, wherein the drug is selected from a steroid, antihistamine, a beta adrenergic agonist, an anticholinergic drug, a methylxanthine, an anti-IgE, an anti-leukotriene, an anti-beta2 integrin, an anti-alpha-4 integrin, an H1-receptor antagonist, an anti-CCR3 antagonist and an anti-selectin.

14. The method of claim 1, wherein the agent is administered subcutaneously, intravenously, intra-peritoneally, intra-muscularly, intra-arterially, intra-colon, or via ingestion, inhalation, orally, or topically.

15. The method of claim 1, wherein the amount of the agent is administered in an amount from about 0.01 mg/kg to about 10 mg/kg body weight.

* * * * *

SEQUENCE LISTING

```
<160> NUMBER OF SEQ ID NOS: 7

<210> SEQ ID NO 1
<211> LENGTH: 173
<212> TYPE: PRT
<213> ORGANISM: Homo sapiens

<400> SEQUENCE: 1

Met Ala Arg Met Asn Arg Pro Ala Pro Val Glu Val Thr Tyr Lys Asn
1               5                   10                  15

Met Arg Phe Leu Ile Thr His Asn Pro Thr Asn Ala Thr Leu Asn Lys
            20                  25                  30

Phe Ile Glu Glu Leu Lys Lys Tyr Gly Val Thr Thr Ile Val Arg Val
        35                  40                  45

Cys Glu Ala Thr Tyr Asp Thr Thr Leu Val Glu Lys Glu Gly Ile His
    50                  55                  60

Val Leu Asp Trp Pro Phe Asp Asp Gly Ala Pro Pro Ser Asn Gln Ile
65                  70                  75                  80

Val Asp Asp Trp Leu Ser Leu Val Lys Ile Lys Phe Arg Glu Glu Pro
```

85                  90                  95
Gly Cys Cys Ile Ala Val His Cys Val Ala Gly Leu Gly Arg Ala Pro
                100                 105                 110

Val Leu Val Ala Leu Ala Leu Ile Glu Gly Gly Met Lys Tyr Glu Asp
        115                 120                 125

Ala Val Gln Phe Ile Arg Gln Lys Arg Gly Ala Phe Asn Ser Lys
    130                 135                 140

Gln Leu Leu Tyr Leu Glu Lys Tyr Arg Pro Lys Met Arg Leu Arg Phe
145                 150                 155                 160

Lys Asp Ser Asn Gly His Arg Asn Asn Cys Cys Ile Gln
                165                 170

<210> SEQ ID NO 2
<211> LENGTH: 522
<212> TYPE: DNA
<213> ORGANISM: Homo sapiens

<400> SEQUENCE: 2
atggctcgaa tgaaccgccc agctcctgtg aagtcacat acaagaacat gagatttctt      60
attacacaca atccaaccaa tgcgacctta aacaaattta taggaaact taagaagtat     120 ggagttacca caatagtaag agtatgtgaa gcaacttatg acactactct tgtggagaaa     180
gaaggtatcc atgttcttga ttggcctttt gatgatggtg caccaccatc caaccagatt     240
gttgatgact ggttaagtct tgtgaaaatt aagtttcgtg aagaacctgg ttgttgtatt     300
gctgttcatt gcgttgcagg ccttgggaga gctccagtac ttgttgccct agcattaatt     360
gaaggtggaa tgaaatacga agatgcagta caattcataa gacaaaagcg gcgtggagct     420
tttaacagca gcaacttcct gtatttggag aagtatcgtc ctaaaatgcg gctgcgtttc     480
aaagattcca acggtcatag aaacaactgt tgcattcaat aa                       522

<210> SEQ ID NO 3
<211> LENGTH: 151
<212> TYPE: PRT
<213> ORGANISM: Homo sapiens

<400> SEQUENCE: 3

Glu Phe Met Lys Cys Ser Trp Val Ile Leu Phe Leu Phe Ser Val Thr
1               5                   10                  15

Ala Gly Val His Ser Gln Val Gln Phe Gln Gln Ser Gly Ala Glu Leu
                20                  25                  30

Ala Lys Pro Gly Ala Ser Val Lys Met Ser Cys Lys Ala Ser Gly Tyr
            35                  40                  45

Thr Phe Thr Ser Tyr Arg Met His Trp Val Lys Gln Arg Pro Gly Gln
        50                  55                  60

Gly Leu Glu Trp Ile Gly Tyr Ile Asn Pro Ser Thr Gly Tyr Thr Glu
65                  70                  75                  80

Tyr Asn Gln Lys Phe Lys Asp Lys Ala Thr Leu Thr Ala Asp Lys Ser
                85                  90                  95

Ser Ser Thr Ala Tyr Met Gln Leu Ser Ser Leu Thr Ser Glu Asp Ser
                100                 105                 110

Ala Val Tyr Tyr Cys Ser Ser Tyr Gly Asn Phe Gly Tyr Trp Gly Gln
            115                 120                 125

Gly Thr Thr Leu Thr Val Ser Ser Glu Ser Gln Ser Phe Pro Asn Val
        130                 135                 140

Phe Pro Leu Val Ser Leu Gly

<210> SEQ ID NO 4
<211> LENGTH: 127
<212> TYPE: PRT
<213> ORGANISM: Homo sapiens

<400> SEQUENCE: 4

```
Val Tyr Cys Ser Leu Val Arg Val Ser Leu Thr Cys Arg Ala Ser Gln
1               5                   10                  15

Asp Ile Gly Ser Ser Leu Asn Trp Leu Gln Gln Lys Ala Asp Gly Thr
            20                  25                  30

Ile Lys Arg Leu Ile Tyr Ala Thr Ser Ser Leu Asp Ser Gly Val Pro
        35                  40                  45

Lys Arg Phe Ser Gly Ser Arg Ser Gly Ser Asp Tyr Ser Leu Thr Ile
    50                  55                  60

Ser Ser Leu Glu Ser Glu Asp Phe Val Asp Tyr Tyr Cys Leu Gln Tyr
65                  70                  75                  80

Ala Ser Ser Pro Trp Thr Phe Gly Gly Gly Thr Lys Leu Glu Ile Lys
                85                  90                  95

Arg Ala Asp Ala Ala Pro His Trp Arg Ser Cys Arg Ser Arg Glu Leu
            100                 105                 110

Trp Leu His His Leu Ser Ser Ser Arg His Leu Met Ser Ser
        115                 120                 125
```

<210> SEQ ID NO 5
<211> LENGTH: 157
<212> TYPE: PRT
<213> ORGANISM: Homo sapiens

<400> SEQUENCE: 5

```
Glu Phe Met Glu Trp Ser Trp Val Ile Leu Phe Leu Leu Ser Ile Ile
1               5                   10                  15

Ala Gly Val His Cys Gln Val Gln Leu Gln Gln Ser Gly Pro Glu Leu
            20                  25                  30

Val Lys Pro Gly Ala Ser Val Arg Ile Ser Cys Lys Ala Ser Gly Tyr
        35                  40                  45

Thr Phe Thr Ser Tyr Tyr Ile His Trp Val Lys Gln Arg Pro Gly Gln
    50                  55                  60

Gly Leu Glu Trp Ile Gly Trp Ile Tyr Pro Gly Asn Val Asn Thr Glu
65                  70                  75                  80

Tyr Asn Glu Lys Phe Arg Gly Lys Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Val Tyr Phe Cys Ala Ser Glu Glu Arg Asn Tyr Pro Trp Phe Ala
        115                 120                 125

Tyr Trp Gly Gln Gly Thr Leu Val Thr Val Ser Ala Ala Lys Thr Thr
    130                 135                 140

Pro Pro Pro Val Tyr Pro Leu Val Pro Gly Ser Leu Gly
145                 150                 155
```

<210> SEQ ID NO 6
<211> LENGTH: 152
<212> TYPE: PRT
<213> ORGANISM: Homo sapiens

<400> SEQUENCE: 6

-continued

```
Trp Glu Phe Met Glu Thr Asp Thr Leu Leu Leu Trp Val Leu Leu Leu
1               5                   10                  15

Trp Val Pro Gly Ser Thr Gly Asp Ile Val Leu Thr Gln Ser Pro Ala
                20                  25                  30

Ser Leu Ala Val Ser Leu Gly Gln Arg Ala Thr Ile Ser Cys Lys Ala
            35                  40                  45

Ser Gln Ser Val Glu Asp Asp Gly Glu Asn Tyr Met Asn Trp Tyr Gln
        50                  55                  60

Gln Lys Pro Gly Gln Ser Pro Lys Leu Leu Ile Tyr Ala Ala Ser Asn
65                  70                  75                  80

Leu Glu Ser Gly Ile Pro Ala Arg Phe Ser Gly Ser Gly Ser Gly Thr
                85                  90                  95

Asp Phe Thr Leu Asn Ile His Pro Val Glu Glu Asp Ala Ala Thr
                100                 105                 110

Tyr Tyr Cys Gln Gln Ser Asn Glu Asp Pro Phe Thr Phe Gly Ser Gly
            115                 120                 125

Thr Lys Leu Glu Ile Lys Arg Ala Asp Ala Ala Pro Thr Val Ser Ile
        130                 135                 140

Phe Pro Pro Ser Ser Lys Leu Gly
145                 150

<210> SEQ ID NO 7
<211> LENGTH: 148
<212> TYPE: PRT
<213> ORGANISM: Homo sapiens

<400> SEQUENCE: 7

Met Ala Arg Met Asn Arg Pro Ala Pro Val Glu Val Thr Tyr Lys Asn
1               5                   10                  15

Met Arg Phe Leu Ile Thr His Asn Pro Thr Asn Ala Thr Leu Asn Lys
                20                  25                  30

Phe Ile Glu Glu Leu Arg Lys Lys Tyr Gly Val Thr Thr Ile Val Arg
            35                  40                  45

Val Cys Glu Ala Thr Tyr Asp Thr Thr Leu Val Glu Lys Glu Gly Ile
        50                  55                  60

His Val Leu Asp Trp Pro Phe Asp Asp Gly Ala Pro Pro Ser Asn Gln
65                  70                  75                  80

Ile Val Asp Asp Trp Leu Ser Leu Val Lys Ile Lys Phe Arg Glu Glu
                85                  90                  95

Pro Gly Cys Cys Ile Ala Val His Cys Val Ala Gly Leu Gly Lys Arg
                100                 105                 110

Arg Gly Ala Phe Asn Ser Lys Gln Leu Leu Tyr Leu Glu Lys Tyr Arg
            115                 120                 125

Pro Lys Met Arg Leu Arg Phe Lys Asp Ser Asn Gly His Arg Asn Asn
        130                 135                 140

Cys Cys Ile Gln
145
```